United States Patent
Jones

(10) Patent No.: US 9,040,672 B2
(45) Date of Patent: *May 26, 2015

(54) DEVICES AND METHODS FOR REDUCING MATRIX EFFECTS

(75) Inventor: David C. Jones, Long Beach, CA (US)

(73) Assignee: Agilent Technologies, Inc., Santa Clara, CA (US)

(*) Notice: Subject to any disclaimer, the term of this patent is extended or adjusted under 35 U.S.C. 154(b) by 521 days.

This patent is subject to a terminal disclaimer.

(21) Appl. No.: 13/175,161

(22) Filed: Jul. 1, 2011

(65) Prior Publication Data

US 2011/0263040 A1    Oct. 27, 2011

Related U.S. Application Data

(63) Continuation of application No. 11/803,824, filed on May 16, 2007, now Pat. No. 7,999,084.

(51) Int. Cl.
| | | |
|---|---|---|
| *C07K 14/00* | (2006.01) | |
| *G01N 1/40* | (2006.01) | |
| *B01L 3/02* | (2006.01) | |
| *B01L 3/00* | (2006.01) | |
| *G01N 35/10* | (2006.01) | |

(52) U.S. Cl.
CPC .............. *G01N 1/405* (2013.01); *B01L 3/0275* (2013.01); *B01L 3/5085* (2013.01); *B01L 2300/0681* (2013.01); *G01N 35/1074* (2013.01); *G01N 2035/1053* (2013.01)

(58) Field of Classification Search
None
See application file for complete search history.

(56) References Cited

U.S. PATENT DOCUMENTS

| | | | |
|---|---|---|---|
| 5,759,549 A | 6/1998 | Hiltunen et al. | |
| 5,885,921 A | 3/1999 | Krupey | |
| 6,177,008 B1 | 1/2001 | Treiber et al. | |
| 6,254,780 B1 | 7/2001 | Bouvier | |
| 6,723,236 B2* | 4/2004 | Fisk et al. | 210/198.2 |
| 7,999,084 B2* | 8/2011 | Jones | 530/412 |
| 2003/0178370 A1 | 9/2003 | Fisk et al. | |
| 2005/0045543 A1 | 3/2005 | Gjerde et al. | |
| 2005/0054077 A1 | 3/2005 | Bennett et al. | |
| 2005/0054707 A1 | 3/2005 | Jones | |
| 2006/0194268 A1 | 8/2006 | Hazato et al. | |
| 2007/0003965 A1 | 1/2007 | Ramsay et al. | |
| 2008/0213906 A1 | 9/2008 | Aurand et al. | |

FOREIGN PATENT DOCUMENTS

| | | |
|---|---|---|
| JP | 2002-296258 | 10/2002 |
| JP | 2007503595 A | 2/2004 |
| JP | 2006-023205 | 1/2006 |
| JP | 2006234694 A | 9/2006 |
| WO | 2004/106914 A1 | 12/2004 |
| WO | 2006/069023 A2 | 6/2006 |

OTHER PUBLICATIONS

Martin Ahnoff and Helena Hagelin; "Matrix Effects in Electrospray Ionization: Characterization of Plasma Phospholipids as Suppressors/Enhancers of Ionization Efficiency"; 52nd ASMS Conference (2004).

Patrik Appelblad and Knut Irgum; "Separation and detection of neuroactive steroids from biological matrices"; Journal of Chromatography A, 955 (2002) pp. 151-182.

Patrick K. Bennett et al.; Managing Phospholipid-Based Matrix Effects in Bioanalysis; Tandem Labs available online at WWW. tandemlabs.com; 7 pages accessed Feb. 26, 2007.

Patrick Bennett and Hairui Liang; Overcoming Matrix Effects Resulting from Biological Phospholipids Through Selective Extractions in Quantitative LC/MS/MS; Tandem Labs; 52nd ASMS Conference, (2004).

Ryan Bonfiglio et al; The Effects of Sample Preparation Methods on the Variability of the Electrospray Ionization Response for Model Drug Compounds; (Rapid Communications in Mass Spectrometry), (1999) pp. 1175-1185.

Erin Chambers et al.; "Systematic and comprehensive strategy for reducing matrix effects in LC/MS/MS analyses"; Journal of Chromatography B, 852 (2007) 22-34, pp. 22-34.

Chen et al.; "Using Supercritical Fluid Chromatography to Alleviate the Imprecision in Bionanalysis Resulting from Matrix Effect of Phospholipids"; 54th ASMS Conference, (2006).

Roy A. Johanson et al.; "Phosphatidylcholine removal from brain lipid extracts expands lipid detection and enhances phosphoinositide quantification by matrix-assisted laser desorption/ionization time-of-flight (MALDI-TOF) mass spectrometry"; Analytical Biochemistry 362 No. 2 (2007) pp. 155-167.

Henk Lingeman et al.; "Particle-loaded membranes for sample concentration and/or clean-up in bioanalysis"; Journal of Chromatography B, 689 No. 1 (1997) pp. 221-237.

James L. Little et al.; "Liquid chromatography-mass spectrometry/mass spectrometry method development for drug metabolism studies: Examining lipid matrix ionization effects in plasma"; Journal of Chromatography B, 833 No. 2 (2006) pp. 219-230.

(Continued)

*Primary Examiner* — Anand Desai

(57) ABSTRACT

Devices and methods are provided for reducing matrix effects in protein precipitated bioanalytical samples comprising: a support, and a sorbent associated with the support capable of binding matrix interfering agents present in the bioanalytical sample, wherein the device further comprises filtering means for removing precipitated protein particles. The filtering means is a size exclusion filter or a polymeric or inorganic monolith having a maximum pore size less than or equal to the diameter of the particles to be removed from the sample, and can be integral with the sorbent or associated with the sorbent. The sorbent is characterized by sufficient selectivity between the matrix interfering agents and analytes of interest to provide retention of the matrix interfering agents while providing elution of the analytes of interest (e.g., a reversed phase or a polar modified reversed phase). Typical devices incorporating these features include luer syringe filters, individual filter cartridges, multiwell plates, pipette tips, or inline columns for multiple or single use.

18 Claims, 24 Drawing Sheets

(56) References Cited

OTHER PUBLICATIONS

Min Meng and Patrick Bennett; "A Source for Imprecision Resulting from Ionization Suppression from Strongly Retained Phospholipids and Dioctyl Phthalate"; Tandem Labs; 52nd ASMS Conference; (2004).

Jim X. Shen et al.; Minimization of ion suppression in LC-MS/MS analysis through the application of strong cation exhange solid-phase extraction (SCX-SPE); Journal of Pharmaceutical and Biomedical Anaylsis vol. 37 No. 2 (2005) pp. 359-367.

KC Van Horne et al; "Investigation of Analyte Recoveries from a New Sorbent Designed to Remove Phospholipids and Reduce Associated Matrix Effects"; Tandem Labs, 52nd ASMS Conference, (2004).

KC Van Horne and Patrick K. Bennett; "Preventing Matrix Effects by Using New Sorbents to Remove Phospholipids from Biological Samples" AAPS Conference, (2003).

* cited by examiner

DEVICES AND METHODS FOR REDUCING MATRIX EFFECTS

CROSS REFERENCE TO RELATED APPLICATIONS

This application is a continuation of and claims the benefit of priority to U.S. patent application Ser. No. 11/803,824 filed May 16, 2007 now U.S. Pat. No. 7,999,084, the entire disclosure of which is incorporated herein by reference.

FIELD OF THE INVENTION

This invention relates generally to devices and methods for preparing bioanalytical samples for analytical testing.

BACKGROUND OF THE INVENTION

Bioanalytical testing and quantitation methods suffer from interference from contaminants that can decrease or increase sensitivity to various analytes disproportionately to their abundance in the sample. Liquid chromatography-mass spectrometry/mass spectrometry (LC/MS-MS) is the preferred method for drug metabolism studies; however matrix effects can lead to significant analytical errors and should be investigated to ensure that precision, selectivity and sensitivity are not compromised. (Little, J. L. et al. (2006) *J. Chromatog.* 833, 219). In particular, phospholipids such as phosphatidylcholines interfere with analyte ionization in electrospray MS detection by reducing analyte sensitivity, commonly referred to as ion suppression or matrix effects. See Ahnoff, M. and Hagelin, H. "Matrix Effects in Electrospray Ionization: Characterization of Plasma Phospholipids as Suppressors/Enhancers of Ionization Efficiency," presented at the American Society for Mass Spectrometry, 52$^{nd}$ Conference on Mass Spectrometry (2004)). Further compounding the problem is that differing lipid composition of different samples, such as blood plasmas from varying animal species, can change the response of the analyte and cause problems in quantitation. These matrix effects are further discussed by the following presentations by Bennett, et al., which report the divergent calibration curves and the retention time shifts that can result from phospholipid contamination of bioanalytical samples: "Managing Phospholipid-Based Matrix Effects in Bioanalysis," www.tandemlabs.com/capabilities_publications.html (accessed Feb. 26, 2007); "A Source of Imprecision Resulting from Ionization Suppression from Strongly Retained Phospholipids and Dioctyl Phthalate," presented at the American Society for Mass Spectrometry, 52$^{nd}$ Conference on Mass Spectrometry (2004)).

In addition, the presence of contaminants can result in incomplete solvent extraction and hence underreporting of analyte concentrations, or can build up on analytical instrumentation, destroying sensitivity or resulting in downtime while cleaning procedures are instituted. Contaminants such as phospholipids have a tendency to build up on a typical reverse phase HPLC columns during repeated analyses of precipitated plasma samples. Accumulated phospholipids can bleed off in subsequent injections, causing a drift in analyte sensitivity over the course of multiple injections. See Bennett and Liang, "Overcoming Matrix Effects Resulting from Biological Phospholipids Through Selective Extractions in Quantitative LC/MS/MS," presented at the American Society for Mass Spectrometry, 52$^{nd}$ Conference on Mass Spectrometry (2004). Removing the phospholipids requires extensive solvent washing to regenerate a column to proper condition.

Various approaches have been utilized in an attempt to solve these problems. Current methods for the removal of phospholipids from bioanalytical samples including liquid/liquid extraction (LLE) and solid phase extraction (SPE) are complicated and require a good deal of method development and the potential for analyte losses. For example, use of stronger eluting strength solvents in SPE can paradoxically result in decreased sample detection due to matrix effects, presumably due to contamination of the sample with phospholipids. However, limiting the eluting solvent strength to avoid contamination of samples with phospholipids can result in incomplete recovery of less polar analytes. LLE approaches require excessive amounts of labor and time to remove contaminating phospholipids, such as performing extraction and separation steps, and drying down or freezing samples, in order to remove the contaminants. For example, Bonfiglio et al. discuss the ability of several common extraction procedures to remove endogenous plasma components that cause ion suppression in electrospray ionization tandem mass spectrometry. LLE using methyl-t-butyl ether, SPE with Oasis and Empore, and acetonitrile (ACN) protein precipitation sample preparation methods were compared. These researchers found that ACN protein precipitated samples showed the greatest amount of ion suppression while LLE extracts demonstrated the least. In addition, the ion suppression was found to be analyte dependent, and associated with the most polar analyte. The least ion suppression for all analytes was observed in samples treated with both LLE and SPE. The authors conclude that there were most likely multiple endogenous components involved in ion suppression, and that the effects may persist well after the injection into the HPLC system is made, resulting in the collection of invalid data. A further filtration step was suggested in an effort to provide yet cleaner samples for analysis. (Bonfiglio, R., et al. (1999) *Rapid Comm. Mass. Spectr.* 13, 1175). However, use of multiple sample preparation steps is labor and time intensive, and increases the cost of performing analyses.

More recently, new approaches for removing phospholipids from samples have been attempted. For example, Johanson reported that use of strong cation exchange column to remove cationic lipids including phosphatidylcholines from lipid extracts resulted in the ready detection of peaks that had been completely suppressed in the crude extract. (Johanson, R. A., et al. (2007) *Anal. Biochem.* 362, 155). U.S. Patent Application Publication No. 20050054077 (Bennett, et al.) describes devices and methods for removing phospholipids from biological samples involving the use of a phospholipotropic multivalent cation coupled to a support. Such cations reportedly include transition metals, lanthanides or actinides, preferably cerium. Use of these phospholipotropic multivalent cation sorbents was further described by Van Home, et al., describing the sorbents as possessing high oxophilicity for the phosphate groups on the phospholipid molecules. (Van Home, K. C., et al. "Preventing Matrix Effects By Using New Sorbents to Remove Phospholipids from Biological Samples" (2003) presented at the *Proceedings of the American Association of Pharmaceutical Scientists Conference*). The authors reported a goal of providing facile removal of phospholipids from biological samples and extracts utilizing an extraction chemistry that would not remove desirable pharmaceutical analytes. Many different mechanisms reportedly were evaluated, including reverse-phase (nonpolar) and both anion and cation exchange. Phospholipid extraction was implemented via extraction sorbents used alone or in combination with protein precipitation, liquid liquid extraction (LLE) or solid phase extraction (SPE). In particular, the phospholipid content of extracts reconstituted in methanol was reportedly reduced by as much as 94-96% using the lanthanide sorbent alone. Use of a lanthanide extraction sorbent to remove phospholipid from a protein precipitated sample reconstituted in methanol reportedly resulted in phospholipid removal of about 92%-98% and enhanced detection of spiked analytes. However, the procedure required centrifugation followed by solvent evaporation and reconstitution, which is labor and time consuming and adds to the costs of performing analysis. Use of a lanthanide extraction sorbent to remove phospholipid from a sample after methyl-t-butyl ether LLE reportedly resulted in phospholipid removal of about 95%-97% but without significant enhanced detection of spiked analytes. The authors concluded that immobilized lanthanide metal centers are an essential element for highly selective binding for phospholipid extraction via binding to the phosphate groups.

Shen, et al. describe an evaluation of three different types of ion-exchange solid phase extraction media in an effort to determine the abilities of the media to remove phospholipids from analyte solutions. These authors reported that mixed mode phases fulfill the requirement of retaining both analytes and diverse metabolites, while reverse-phase retention mechanisms were detrimental in eliminating ion suppression caused by late eluting phospholipids, and advised using an ion exchange mechanism alone rather than mixed mode extraction phases. (Shen, J. X., et al. (2005) *J. Pharm. Biomed. Anal.* 37, 359).

U.S. Pat. No. 5,885,921 to Krupey describes the use of hydrophobic silica adsorbents for the removal of lipids in samples, sold under the brand name Cleanascite™ for lipid adsorbent and clarification agent for pretreatment of samples prior to further purification. The adsorbent is added to samples and then the sample is centrifuged to remove the adsorbent containing bound impurities. However, this procedure requires two steps to add the sorbent and then remove it, and risks removal of analytes from samples.

U.S. Pat. No. 5,759,549 to Hiltunen describes the use of supercritical fluid extraction for the isolation of lipids from mixtures of lipids. However, this procedure requires specialized equipment and adds to the expense and cost of removing lipids from samples.

Little et al. describe an "in source multiple reaction monitoring" method for monitoring method development of pharmaceutical analysis in an effort to determine whether there are co-eluting matrix constituents resulting in ion suppression of analytes of interest. However, these procedures do not remove the matrix constituents causing the ion suppression, but merely attempt to work around the problem, and require the elution of the most hydrophobic lipids from the column after each analysis. (Little, J. L. et al. (2006) *J. Chromatog.* 833, 219).

Therefore, numerous methods for removing lipid contaminants in biological samples are available, although the procedures are time and labor intensive. Further, samples also contain contaminating proteins, which must also be removed. However, use of denaturing solvents to effect precipitation results in greater extraction of lipid contaminants and significant ion suppression of analytes present. Therefore, there is a minimum of two steps needed to prepare a bioanalytical sample for analysis, if the researcher hopes to maintain his equipment in good working order, and to achieve reliable and accurate quantitation of bioanalytes. When working with small sample volumes, or when multiple testing is needed, such multiple sample preparation procedures are likely to reduce sample such that an insufficient amount remains for the testing required. In addition, multiple sample preparation steps result in a loss of researcher time and labor and raise the costs for the analytical testing laboratory.

Accordingly, there remains a need for rapid procedures that can remove both phospholipids and other agents causing matrix effects and proteins from a bioanalytical sample prior to performance of analytical procedures.

SUMMARY OF THE INVENTION

Accordingly, it is a primary object of the invention to provide procedures for reducing matrix effects in bioanalytical samples.

It is a further object of the invention to provide procedures that can be performed rapidly to remove phospholipids, surfactants, and proteins from a bioanalytical sample prior to performance of analytical procedures.

It is yet a further object of the invention to provide procedures for reducing matrix effects that can be performed in the ordinary course of sample preparations and that do not require additional steps or expensive equipment.

Accordingly, there is provided a device for reducing matrix effects in a protein precipitated bioanalytical sample comprising: a support, and a sorbent associated with the support capable of binding matrix interfering agents present in the bioanalytical sample, wherein the device further comprises filtering means for removing precipitated protein particles. The filtering means is characterized in having pore sizes between about 0.05 μm and about 0.5 μm in diameter for removing precipitated protein particles present in the sample. In preferred embodiments, the filter means has pore sizes between about 0.1 μm and about 0.2 μm in diameter, and in particular embodiments, the filter means comprises pores of 0.2 and 0.45 μm in diameter. Preferably, the filtering means is selected from a size exclusion filter or a polymeric or inorganic monolith having a maximum pore size less than or equal to the diameter of the particles to be removed from the sample, and can be integral with the sorbent or associated with the sorbent. Preferably, when the filtering means is integral with the sorbent, the filtering means is a porous inorganic monolith having macropores of a diameter sufficiently small so as to exclude particles from the sample, and the sorbent is a reversed phase or polar modified reversed phase bonded to the porous inorganic monolith. Preferably, the filtering means is effective to provide optical clarity to the protein precipitated bioanalytical sample (e.g., % T at 524 nm>95%).

The sorbent is characterized by sufficient selectivity between the matrix interfering agents and analytes of interest to provide retention of the matrix interfering agents while providing elution of the analytes of interest. Preferably, the sorbent is characterized by a selectivity greater than 1 for matrix interfering agents and analytes of interest, and in certain embodiments, the selectivity is at least 1.1, in additional embodiments, the selectivity is at least 1.2, in yet other embodiments, the selectivity is at least 1.3, in additional embodiments, the selectivity is at least 1.4, and in certain especially preferred embodiments, the selectivity is at least 1.5. Preferably, the sorbent comprises a reversed phase or a polar modified reversed phase, and in particular embodiments, the polar modified reversed phase is an amide modified reversed phase. The sorbent selectivity for matrix interfering agents and analytes of interest is such that when the bioanalytical sample comprises at least 50% (v/v) denaturing organic solvent, the sorbent retains matrix interfering agents while not retaining analytes of interest. Preferably, the sorbent binds at least 50% of the matrix interfering agents present in the bioanalytical sample, while providing recovery of at least 75% of the analytes in the solvent output from the device, and more preferably, the sorbent provides for recovery of at least 90% of the analytes. In preferred embodiments, the sorbent binds at least 70%, or more preferably at least 85%, or more preferably at least 90%, and even more preferably at least 95%, and most preferably at least 99% of the matrix interfering agents.

Typical matrix interfering agents include surfactants, lipids, excipients, or dosing agents. Typical implementations of the device are adapted for use as luer syringe filters, individual filter cartridges, multiwell plates, pipette tips, or an inline columns for multiple or single use. In additional embodiments, the support further comprises reservoir means for performing protein precipitation within the device.

The invention further provides methods for preparing a sample comprising matrix interfering agents and proteins for analysis. Typical analyses include chromatographic, spectrophotometric, mass spectrometric, and the like, and combinations thereof. For example, an exemplary analysis method in the bioanalytical arts for determining pharmaceutical analytes is LC/MS-MS. Accordingly, there are provided methods for reducing matrix effects and removing protein precipitates in a bioanalytical sample, said methods comprising: a) providing a device comprising a support, and a sorbent associated with the support, wherein said sorbent is characterized by a selectivity greater than 1 for matrix interfering agents relative to analytes of interest present in the bioanalytical sample, and further comprising filtering means for removing protein precipitates present in the sample; b) contacting the bioanalytical sample with the sorbent; and c) eluting the analytes from the sorbent while retaining the matrix interfering agents and precipitated proteins, wherein the amount of matrix interfering agents and proteins in the resulting treated sample is reduced. In certain embodiments, the method further comprises precipitating the proteins in the bioanalytical sample in the device prior to or simultaneously with the step of contacting the bioanalytical sample with the sorbent. Preferably, step c) is performed using vacuum, centrifugal force or positive pressure to cause the sample to pass through the sorbent and the filtering means, thereby removing matrix interfering agents and precipitated proteins. Preferably, the filtering means is characterized in having pore sizes between about 0.05 $\mu$m and about 0.5 $\mu$m in diameter for removing precipitated protein particles present in the sample, and in certain embodiments, the filtering means comprises pore sizes between about 0.1 $\mu$m and about 0.2 $\mu$m. In particular embodiments, the filtering means comprises pores sizes of 0.1, 0.2 and 0.45 $\mu$m. Preferably, the matrix interfering agents are surfactants, lipids, excipients, or dosing agents, and in preferred embodiments, the lipids are phospholipids, and the surfactants are selected from anionic surfactants or nonionic surfactants. Preferably the surfactants comprise a hydrocarbon chain which can be advantageously retained using the sorbents described herein. Preferably, the sorbent is characterized by sufficient selectivity between the matrix interfering agents and analytes of interest to provide retention of the matrix interfering agents while providing elution of the analytes of interest. In certain embodiments, the sorbent comprises a reversed phase or a polar modified reversed phase. In particular embodiments, there are provided methods for reducing matrix effects and removing precipitated proteins in a protein precipitated bioanalytical sample comprising matrix interfering agents and analytes of interest, the method comprising passing the sample through the devices described herein.

In additional embodiments, methods are provided for reducing matrix effects in a protein precipitated bioanalytical sample comprising matrix interfering agents and analytes of interest, the method comprising: a) providing a device comprising a support, and a sorbent associated with the support, wherein said sorbent is characterized by a selectivity greater than 1 for matrix interfering agents relative to analytes of interest present in the bioanalytical sample; b) contacting the bioanalytical sample with the sorbent; and c) eluting the analytes from the sorbent while retaining the matrix interfering agents, wherein the amount of matrix interfering agents in the resulting treated sample is reduced. The device can further comprise filtering means for removing precipitated protein particles. In preferred embodiments, when the bioanalytical sample comprises at least 50% (v/v) denaturing organic solvent, the sorbent retains matrix interfering agents while not retaining analytes of interest. In additional embodiments, the sorbent retains matrix interfering agents while not retaining analytes of interest even at 66%, 75%, or even 90% (v/v) organic solvent, or in the presence of pH modifiers (e.g., acids, bases). Preferably, the sorbent binds at least 50% of the matrix interfering agents present in the bioanalytical sample, while providing recovery of at least 90% of the analytes in the solvent output from the device, and more preferably, the sorbent binds at least 70%, or more preferably 85%, or more preferably 90%, or even more preferably 95%, and most preferably 99% of the matrix interfering agents present in the sample.

In certain embodiments, the devices can be used in a combination filtration solid phase extraction mode (SPE). For example, the methods can further conprise optionally conditioning the sorbent by washing the sorbent with at least one conditioning solvent or mixture of solvents prior to contacting the bioanalytical sample with the sorbent. The methods can further comprise optionally washing the sorbent with adsorbed analytes and matrix interfering agents with a wash solvent or mixture of solvents to remove unbound components. In accordance with further SPE uses, the methods can further comprise eluting analytes from the sorbent with eluting solvents of sequentially increasing solvent strength to remove more nonpolar analytes without contaminating the analytes with the adsorbed matrix interfering agents.

In an additional embodiment, a method is provided for reducing matrix effects in a bioanalytical sample comprising at least 50% (v/v) protein denaturing organic solvent, the method comprising: a) providing a sorbent capable of binding matrix interfering agents present in the bioanalytical sample; b) contacting the bioanalytical sample with the sorbent for at least 10 seconds; and c) separating the solution from the sorbent, wherein the amount of matrix interfering agents in the resulting treated sample is reduced. Preferably, said contacting is performed for from about 10 seconds to about 10 minutes, and the sorbent binds at least 50% of the matrix interfering agents present in the bioanalytical sample, while providing recovery of at least 90% of the analytes in the solvent output from the device. The method can further comprise contacting the bioanalytical sample with a filtering means for removing precipitated protein particles. Preferably, the contacting with a filtering means and with the sorbent is done in the same step.

In additional embodiments, there is provided a method for preparing a device for reducing matrix effects in a bioanalytical sample, comprising the following steps: a) providing a support capable of containing a quantity of sorbent and a filtering means; and b) providing an amount of sorbent effective to retain matrix interfering agents and a filtering means effective to remove precipitated proteins present in the sample; and c) assembling the filtering means and the sorbent within the support.

Additional objects, advantages and novel features of the invention will be set forth in part in the description which follows, and in part will become apparent to those skilled in the art upon examination of the following, or may be learned by practice of the invention.

DETAILED DESCRIPTION OF THE INVENTION

I. Definitions and Overview

Figure 1:
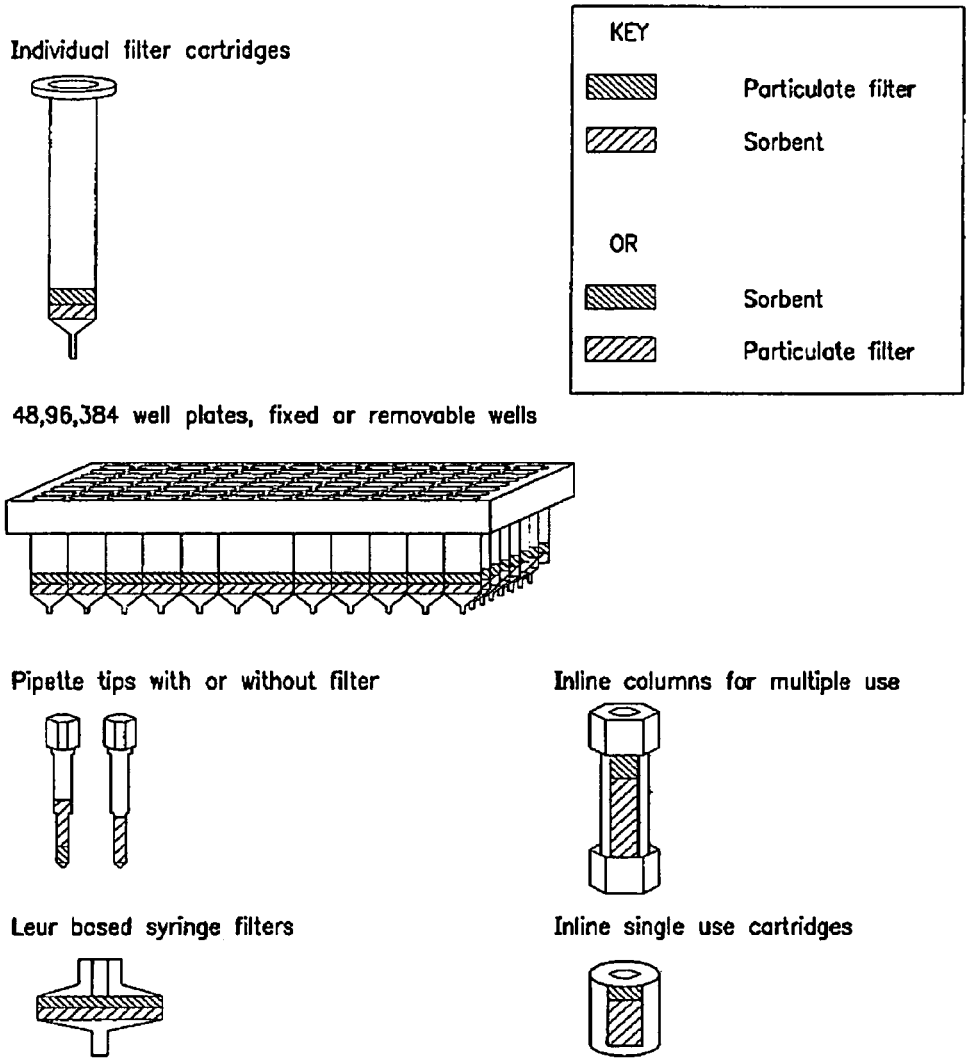
FIG. 1 illustrates several embodiments of the invention.

Before the present invention is described in detail, it is to be understood that unless otherwise indicated this invention is not limited to specific analytes, chromatographic methods, filtration and purification structures, or the like, as such may vary. It is also to be understood that the terminology used herein is for the purpose of describing particular embodiments only and is not intended to limit the scope of the present invention.

It must be noted that as usedherein and in the claims, the singular forms "a," "and" and "the" include plural referents unless the context clearly dictates otherwise. Thus, for example, reference to "an analyte" includes two or more analytes; reference to "a phospholipid" includes two or more phospholipids, and so forth.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

As used herein the term "selectivity" refers to the ratio between corrected retention times ($T_r$) for analytes eluting at different retention times. Corrected $T_r$ is calculated by the following formula: $T_r - T_0$. where $T_0$ is the transit time for unretained species. The sorbents utilized herein provide selectivity between matrix interfering agents and analytes of interest, i.e., the ratio of the corrected $T_r$ for matrix interfering agents relative to the corrected $T_r$ for analytes is greater than 1.

As used herein, the term "analyte" or "analyte of interest" means any molecule to be characterized, identified or quantitated in a sample of biological, organic, synthetic, natural or inorganic origin. For example, a candidate therapeutic compound or metabolite thereof can be an analyte, and can be present in, for example, a blood plasma sample, saliva, urine, drinking water, mixture of synthetic or natural products, or environmental sample. An analyte can exhibit any polarity, from nonpolar to polar.

As used herein, the term "macropores" generally refers to pores with diameters greater than about 0.05 μm; these are considered to be "throughpores" in the sense of allowing fluid flow through a monolithic filter or sorbent. The term "mesopores" refers to pores with diameters between about 2 nm and 50 nm; and the term "micropores" refers to pores with diameters less than about 2.0 nm.

The term "reversed phase" refers to a non-polar stationary phase comprising alkyl or aromatic moeities providing a hydrophobic surface for adsorption of nonpolar compounds. A common reversed phase stationary phase is a silica which has been treated with $RMe_2SiCl$, where R is a straight chain alkyl group such as $C_{18}H_{37}$ or $C_8H_{17}$. Another reversed phase stationary phase is provided by polystyrene-divinylbenzene.

The term "polar modified reversed phase" refers to a non-polar stationary phase comprising alkyl or aromatic moeities providing a hydrophobic surface for adsorption of nonpolar compounds, wherein the stationary phase has been further modified to contain (or further comprises) a polar moiety such as an amide, ether, amino, carboxy, sulfonamide, and the like. Nonlimiting examples of polar modified reversed phase stationary phases are described in U.S. Pat. No. 7,125,488 to Li, U.S. Pat. No. 7,056,858 to Kallury, and U.S. Patent Application Publication Nos. 20060247361 and 20060247362 to Shah.

As used herein, the term "strongly polar" means a molecule that, based on the octanol-water partition coefficient log P, has a log P value of −1.0 to +0.5.

As used herein, the term "moderately polar" means a molecule that, based on the octanol-water partition coefficient log P, has a log P value of 0.5 to 1.5.

As used herein, the term "nonpolar" means a molecule that based on the octanol-water partition coefficient log P, has a log P value greater than or equal to 2.0.

Sorbent polar functionalities as used herein include but are not limited to the following: —NRC(O)— (amide), —C(O)NR— (carbamyl), —OC(O)NR— (carbamate), —OC(O)R (alkyloxy), —NRC(O)O— (urethane), —NRC(O)NR— (carbamide or urea), —NCO (isocyanate), —CHOHCHOH— (diol), $CH_2OCHCH_2O$— (glycidoxy), —$(CH_2CH_2O)_s$— (ethoxy), —$(CH_2CH_2CH_2O)_s$— (propoxy), —C(O)— (carbonyl), —C(O)O— (carboxy), —$CH_2C(O)CH_2$— (acetonyl), —S— (thio), —SS— (dithio), —CHOH—, —O— (ether), —SO— (sulfinyl), —$SO_2$— (sulfonyl), —$SO_3$— (sulfonic acid), —$OSO_3$ (sulfate), —$SO_2NR$— (sulfonamide), —$NR_q$—, (amines), and —$NR_q^+$—, where R is not H (quaternary amines), —CN (nitrile), —NC (isonitrile), —CHOCH— (epoxy), —NHC (NH)NH— (guanidino), —$NO_2$ (nitro), —NO (nitroso), —$OPO_3$— (phosphate), —OH (hydroxy), and s is 1-12.

As used herein, the term "matrix effects" refers to any substance present in a sample that interferes with quantitation of an analyte. Matrix effects can be manifested in traditional chromatographic applications by the co-elution of contaminating matrix constituents with analytes of interest, causing interference with spectrophotometric quantitation methods, for example. Matrix effects are commonly observed in mass spectromertry applications, when ion suppression of an analyte is observed.

As used herein, the term "matrix interfering agent" refers to any substance present in a bioanalytical sample in relatively high concentration (usually at least 1 mg/ml) that causes matrix effects, that is, interferes with quantitation of an analyte. Matrix interfering agents commonly suppress the ionization of a particular analyte present in the sample during electrospray ionization for mass spectrometric analysis. The relative abundance of the analyte can be underrepresented and/or underestimated or overrepresented from its true abundance in the sample due to matrix effects.

The present invention is related to novel sample preparation devices and methods of manufacturing and using them, such as devices for sample preparation for LC/MS, solid phase extraction devices, and the like. The present inventors have surprisingly discovered that a single device can provide the dual functionality of removing precipitated proteins and matrix interferences in one step, resulting in superior analytical capabilities and speeds and performance. Although practitioners have been extensively employing similar devices and methods for sample preparation and the like, the present inventors are the first to discover the combination of filter and sorbent functionality that removes precipitated protein (and other) particulates and that adsorbs matrix interfering agents while selectively eluting analytes of interest, and to utilize these functionalities to produce products having superior performance, time saving, ease of use and manufacture, to the inventors' knowledge to date. The combination of filtering means, sorbents, and solvents allows a one step cleanup procedure for removing precipitated proteins and matrix interfering agents, particularly plasma lipids, which results in not only increased convenience, but cleaner samples for analysis than had heretofore been possible, an unexpected and surprising result.

Accordingly, there are provided devices for reducing matrix effects in a protein precipitated bioanalytical sample comprising: a support, and a sorbent associated with the support capable of binding matrix interfering agents present in the bioanalytical sample, wherein the device further comprises filtering means for removing precipitated protein particles. The invention further provides methods for reducing matrix effects and removing protein precipitates in a bioanalytical sample, said methods comprising: a) providing a device comprising a support, and a sorbent associated with the support, wherein said sorbent is characterized by a selectivity greater than 1 for matrix interfering agents relative to analytes of interest present in the bioanalytical sample, and further comprising filtering means for removing protein precipitates present in the sample; b) contacting the bioanalytical sample with the sorbent; and c) eluting the analytes from the sorbent while retaining the matrix interfering agents and precipitated proteins, wherein the amount of matrix interfering agents and proteins in the resulting treated sample is reduced.

Various aspects and embodiments of the invention will be described in greater detail below.

II. Devices

The devices of the invention comprise a sorbent suitable for the removal of matrix interfering agents (e.g., surfactants, phospholipids, excipients, dosing agents, etc.) from protein precipitated samples in combination with a particulate filter means suitable for the removal of precipitated proteins or other unwanted solid matter. In certain embodiments, the particulate filter functionality and the sorbent are combined into one component. In additional embodiments, the particulate filter is a separate component from the sorbent component. In certain additional embodiments, a particulate filter is not included where protein precipitates or other matter does not interfere with instrument performance or have been removed by other means.

Several different embodiments of the device are shown in FIG. 1. Typical devices include cartridges (e.g., inline cartridges, individual filter cartridges), pipette tips (with or without a protein precipitation filter), multiple well plates of many varieties, syringe filters and inline columns, and the like. An exemplary embodiment is described in Examples 10 and 11, and demonstrates the dramatic improvement in sample preparation procedures possible using the devices of the present invention.

The devices can include particulate porous or nonporous sorbents, monolithic sorbents, sorbent impregnated webs, fibers or filters, or other porous media with the proper selectivity. The sorbents can be polymeric or silica based, as discussed further below. The devices generally include a filtering means, such as size exclusion filters or sorbents providing a dual sorbent and filtering function. The arrangement of filtering means and sorbent is generally unimportant, and can be arranged as desired to suit a particular application. However, where no particles are present or have been removed by other means, the devices can omit the filtering means.

A. Supports

As used herein, the terms "support" mean a porous or non-porous water insoluble material. A support or a supporting format can have any one of a number of configurations or shapes, such as strip, plate, disk, rod, cylinder, well, cone, and the like. A support or supporting format can be hydrophobic, hydrophilic or capable of being rendered hydrophilic, and can comprise inorganic powders such as silica, zirconia, and alumina; natural polymeric materials, synthetic or modified naturally occurring polymers, such as nitrocellulose, cellulose acetate, poly(vinyl chloride), polyacrylamide, polyacrylate, polyethylene, polypropylene, poly(4-methylbutene), polystyrene, polymethacrylate, poly(ethylene terephthalate), nylon, poly(vinyl butyrate), polytetrafluoroethylene (PTFE or Teflon®), etc.; either used by themselves or in combination, and in conjunction with other materials such as glass, ceramics, metals, and the like. The support can be constructed of any material suitable for holding and dispensing liquids, and will generally be a polymeric material such as a polyolefin, fluorinated polymers, polysulfone, polyethersulfone, cellulose acetate, polystyrene, polystyrene/acrylonitrile copolymer, PVDF, and the like. Polyolefinic materials are preferred, for example, polypropylene, polyethylene, poly(tetrafluoroethylene), or copolymers thereof. For nonaqueous liquids, the tube can be constructed of a material that will not dissolve or leach contaminants into the nonaqueous liquid. Preferably, the devices are constructed from ultra-clean polymers, preferably polypropylene.

Support structures can be of any size or shape to suit the need of any specific application. For example, for sample pretreatment applications, the support can be in the form of individual filter cartridges or multiwell plates, luer based syringe filters, pipette tips, as shown in FIG. 1, and the like. In one embodiment, the support can be a multi-well filtration or solid phase extraction apparatus such as described in U.S. Pat. No. 6,491,873 to Roberts. For chromatographic in line use, the support can be in the form of in-line columns for multiple or single use, and the like.

In certain embodiments, the support provides sufficient volume to allow precipitation of proteins directly in the device (e.g., the device includes a reservoir), obviating the need to perform the precipitation in one container and subsequently transfer the sample to the device for removing matrix interfering agents and precipitated proteins. For example, to perform a protein precipitation using a 3:1 or 4:1 dilution of the aqueous bioanalytical sample with a denaturing organic solvent, the device should include a reservoir having up to five times the volume of the original sample volume.

For solid phase extraction applications, the support can be in the form of a syringe cartridge, pipette tip or the like. Theoretically, there is no limitation in size and shape, and the dimensions of the devices can be determined entirely from the constraints of practical applications. For some applications, such as preparative scale applications, much larger devices might be used. Smaller structures may also be contemplated for micro-fabricated devices. The present invention can be applied to make parts in any relevant size range requiring only sufficient material and processing equipment of sufficient size to handle the parts to be processed.

B. Sorbents

The device for reducing matrix effects in a bioanalytical sample comprises a sorbent for selectively retaining matrix interfering agents. Preferably, the sorbent comprises a reversed phase or a polar modified reversed phase. The sorbent is capable of binding analytes and agents contributing to matrix effects present in the bioanalytical sample. The sorbent exhibits selective binding for analytes and matrix interfering agents, meaning that under the solvent conditions utilized herein, the sorbent retains matrix interfering agents while not retaining analytes, even relatively nonpolar analytes such as posaconazole (log P=5.66). Preferably, the sorbent binds at least 50% of the matrix interfering agents present in the bioanalytical sample while providing recovery of at least 75% of the analytes in the solvent output from the device, and preferably at least 90% of the analytes are recovered from the device. In more preferred embodiments, the sorbent binds at least 70%, or more preferably 85%, or more preferably 90%, or even more preferably 95%, or most preferably 99% of the matrix interfering agents.

Typical agents causing matrix effects in test samples include surfactants and lipids, although any agent that causes matrix effects is encompassed in the present invention provided it can be reduced or removed using the devices and methods described herein.

The amount of sorbent needed for a typical plasma sample depends on the binding capacity of the sorbent. A typical plasma sample has a volume between 50 µl and 200 µl and therefore 20-30 mg of Polaris® (10 µm particle size) C18-A is an appropriate amount of sorbent for this sample size. When the sorbent is a glass fiber monolith with embedded particles such as Spec® disks (Varian, Inc., Palo Alto, Calif.), 4 to 8 disks provide an appropriate amount of sorbent. One skilled in the art can readily determine the desired amount of sorbent for a particular application. For example, plasma from different species of animals or from animals fed different diets contains varying amounts of phospholipids. For higher concentrations of phospholipids present in the sample, a relatively larger amount of sorbent would be required for maximal removal of matrix interfering phospholipids.

Preferably, the sorbent is characterized by sufficient selectivity between matrix interfering agents and analytes of interest in the solvent system being utilized in order to provide separation between the interfering agents and analytes. In one embodiment, the sorbent exhibits a selectivity between phosphatidylcholine and an analyte of interest of at least 1.0 Depending on the particular sorbent, solvent conditions, matrix interfering agent and analyte of interest, a selectivity of at least 1.1, more preferably 1.2, more preferably 1.3, more preferably 1.4, or even more preferably 1.5 is provided. As shown in Example 6, use of a polar (amide) modified reversed phase sorbent provides optimal retention of matrix interfering agents and reduction in matrix effects, while allowing maximal recovery of analytes which elute ahead of the matrix interfering agents. Accordingly, a preferred sorbent is an amide modified reversed phase.

Use of pH modifiers provides further control over the selectivity between matrix interfering agents and analytes of interest. Nonpolar basic analytes can be selectively eluted (e.g., are not retained by the sorbent) by acidifying the precipitation solvent solution. Protonation of the base provides a more polar molecule less likely to be retained by the nonpolar stationary phase provided by the sorbent. Similarly, basification of solutions containing acidic analytes leads to less retention, and hence greater separation and enhanced selectivity, between the matrix interfering agents and the acidic analytes of interest. Example 4 and Tables 10 and 11 further illustrate this principle in the operation of the devices and methods of the present invention.

Any sorbent known in the art can in principle be utilized in the devices and methods described herein. Sorbents can include polymeric sorbents, inorganic sorbents, hybrid organic-inorganic sorbents, bonded phases, and combinations thereof.

In one embodiment, the sorbent comprises a monolithic or particulate inorganic substrate that is modified to produce a bonded phase with at least one silane having the formula

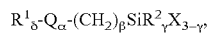

wherein $R^1$ is hydrogen, $C_1$-$C_{100}$ substituted or unsubstituted hydrocarbyl, cycloalkyl, heterocycloalkyl, aryl, or heteroaryl; wherein the substituents are selected from $C_1$-$C_{12}$ hydrocarbyl, hydroxyl, alkoxy, halogen, amino, nitro, sulfo, and carbonyl; $\alpha$ is 0 or 1; $\beta$ is 0-30; $\gamma$ is 0, 1 or 2; $\delta$ is 0-3; $R^2$ is $C_1$-$C_{100}$ substituted or unsubstituted hydrocarbyl, cycloalkyl, heterocycloalkyl, aryl, or heteroaryl; wherein the substituents are selected from $C_1$-$C_{12}$ hydrocarbyl, hydroxyl, alkoxy, halogen, amino, nitro, sulfo, and carbonyl; Q is independently selected from —NHC(O)—, —C(O)NH—, —OC(O)NH—, —NHC(O)O—, —NHC(O)NH—, —NCO, —CHOHCHOH—, CH$_2$OCHCH$_2$O—, —(CH$_2$CH$_2$O)$_n$—, —(CH$_2$CH$_2$CH$_2$O)$_n$—, —C(O)—, —C(O)O—, —OC(O)—, CH$_3$C(O)CH$_2$—, —S—, —SS—, —CHOH—, —O—, —SO—, —SO$_2$—, —SO$_3$—, —OSO$_3$—, —SO$_2$NH—, —SO$_2$NMe-, —NH—, —NMe-, —NMe$_2$$^+$—, —N[(CH$_2$)$_n$]$_2$—, —CN, —NC, —CHOCH—, —NHC(NH)NH—, —NO$_2$, —NO, —OPO$_3$—, where n is 1-30; and X is a leaving group, as described in U.S. Pat. No. 7,125,488 to Li.

Preferably, the inorganic substrate comprises a metal-oxide or metalloid oxide, such as silica, alumina, zeolite, mullite, zirconia, vanadia or titania, or mixtures or composites thereof, having reactive metal oxides capable of reacting with an alkoxysilane, aminosilane, hydroxysilane or halosilane. The inorganic substrate can take the form of beads or regular or irregular particles ranging in size from about 0.001 mm to 10 mm in diameter, preferably 0.005 to 0.04 mm, fibers (hollow or otherwise) of any size, membranes, flat surfaces ranging in thickness, for example, from about 0.1 mm to about 10 mm thick, and sponge-like materials, such as frits or monoliths with pores from 0.05 microns to several mm in diameter. After modification of the inorganic substrate surface with a silane, the silane is covalently attached to the inorganic substrate via an oxygen linkage to produce a bonded phase.

In certain embodiments, the modified inorganic substrate is a bonded alkyl phase such as C8 or C18 (where α is 0), useful in reversed phase adsorption and chromatographic applications. In certain preferred embodiments, α is 1, and the modified inorganic substrate is a bonded polar embedded reversed phase, suitable for enhanced retention of matrix interfering agents without retaining nonpolar analytes under solvent conditions of at least 50% (v/v) organic solvent. In a particularly preferred embodiment, the modified inorganic substrate comprises a C18 bonded phase having a polar embedded amido functionality, such as Polaris® C-18 A (available through Varian, Inc., Palo Alto, Calif.). In another particularly preferred embodiment, the modified inorganic substrate comprises a C18 bonded phase in which remaining silanol groups are further reacted with an amido functionalized endcapping reagent, such as Polaris® C-18 Amide (available through Varian, Inc., Palo Alto, Calif.). In additional embodiments, the modified inorganic substrate comprises a C8 bonded phase, or an ether functionality, such as Polaris® C18-Ether or Polaris® C8-Ether (Varian, Inc., Palo Alto, Calif.). One of ordinary skill will recognize that any of the bonded phases of varying compositions described in U.S. Pat. No. 7,125,488 to Li can be utilized in the inventive devices and methods described herein.

In an additional embodiment, the device comprises a polymeric sorbent described in U.S. Pat. Nos. 7,056,858 and 6,926,823 to Kallury. This sorbent comprises: (i) a polymeric backbone adapted to form at least one of a dipolar interaction and a hydrophobic interaction; and (ii) an amide functionality associated with the backbone and adapted to undergo proton accepting and proton donating interactions. Preferably the amide functionality is associated with the backbone via a covalent bond. A polymeric sorbent of the present invention also comprises an amide functionality associated with the polymeric backbone and adapted to undergo one or more interactions selected from the group consisting of proton accepting, proton donating and dipolar interactions, for example, with the functionalities of an analyte. Representative amide functionalities include acetamide, N-alkylamides, N-aryl-amides and N-heteroaryl amides.

Any polymer adapted to form at least one of a dipolar interaction and a hydrophobic interaction can be employed as a polymeric backbone in this embodiment. A polymeric backbone can comprise, for example, poly(styrene divinylbenzene), copolymers of styrene or divinylbenzene with functionalized styrenes or heterocycles carrying substituents such as halo, alkoxy, ester or nitro; or copolymers such as (but not restricted to) polystyrene-polyacrylamide and polystyrene-polyacrylates. Thus, a representative, but non-limiting, list of polymers that can be employed as a polymeric backbone in a sorbent includes, but is not limited to, poly(styrene divinylbenzene), copolymers comprising styrene or divinylbenzene and methylmethacrylate, halogenated or nitrated or aminated or hydroxylated styrenes, functionalized isocyanurates, urethanes, acrylamides or acrylonitriles and functionalized heterocyclic systems, such as vinyl/allyl pyridines. In one embodiment, a polymeric backbone comprises poly(styrene divinylbenzene). In certain embodiments, it is preferable that the polymeric backbone comprises spherical or non-spherical particles having a diameter of between about 0.001 mm and about 10 mm in diameter, preferably from about 0.005 to about 0.04 mm in diameter.

In other embodiments, a polymeric sorbent can be utilized in a polymer modified porous substrate format, for example, formed on a porous substrate in the form of a monolith, agglomerated particles, or woven or nonwoven fibers, (e.g., glass or polymer fibers). Preferably, the polymer modified porous substrate comprises a porous substrate and a polymeric monolith formed thereon, wherein the polymeric monolith has the formula

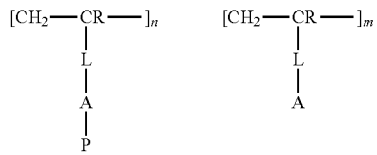

wherein A is selected from C$_{5-10}$ monocyclic or bicyclic aryl or heteroaryl, optionally substituted with -L-Q$_p$-R$_q$; q is 0-3; p is 0-5; Q is —NRC(O)—, —C(O)NR—, —OC(O)NR—, —OC(O)R, —NRC(O)O—, —NRC(O)NR—, —NCO, —CHOHCHOH—, CH$_2$OCHCH$_2$O—, —(CH$_2$CH$_2$O)$_s$— and —(CH$_2$CH$_2$CH$_2$O)$_s$—, —C(O)—, —C(O)O—, —CH$_2$C(O)CH$_2$—, —S—, —SS—, —CHOH—, —O', —SO—, —SO$_2$—, —SO$_3$—, —OSO$_3$, —SO$_2$NR—, —NR$_q$—, and —NR$_q$$^+$—, where R is not H, —CN, —NC, —CHOCH—, —NHC(NH)NH—, —NO$_2$, —NO, 'OPO$_3$—, —OH, where s is 1-12; and R is hydrogen, C$_{5-10}$ monocyclic or bicyclic aryl or heteroaryl, C$_{1-12}$ branched, unbranched, or cyclic hydrocarbyl;

P is

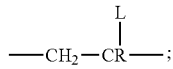

L is a bond or a C$_{1-12}$ branched, unbranched, or cyclic hydrocarbyl; and wherein the order of [—CH$_2$—CR-L-A-P] and [—CH$_2$—CR-L-A] is random, block or a combination thereof, described in U.S. Patent Application Publication No. 20060247352 to Shah.

In yet other embodiments, a polymeric sorbent can be utilized in a polymer modified porous substrate format, for example, formed on a porous substrate in the form of a monolith, agglomerated particles, or woven or nonwoven fibers, (e.g., glass or polymer fibers). Preferably, the polymeric sorbent is a polar functionalized polymer modified porous substrate, comprising a porous substrate and a polar functionalized polymeric monolith formed thereon, wherein the polymeric monolith has the formula

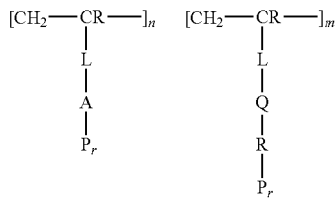

wherein A is selected from $C_{5-10}$ monocyclic or bicyclic aryl or heteroaryl, optionally substituted with $C_{1-12}$ branched or unbranched hydrocarbyl, or halo; wherein n/m is from about 0.001 to about 1000; wherein r is 0 or 1; wherein Q is —NRC(O)—, —C(O)NR—, —OC(O)NR—, —OC(O)R, —NRC(O)O—, —NRC(O)NR—, —NCO, —CHOHCHOH—, $CH_2OCHCH_2O$—, —$(CH_2CH_2O)_n$— and —$(CH_2CH_2O)_s$—, where s is 1-12, —C(O)—, —C(O)O—, —$CH_2C(O)CH_2$—, —S—, —SS—, —CHOH—, —O—, —SO—, —$SO_2$—, —$SO_3$—, —$OSO_3$, —$SO_2NR$—, —$NR_q$—, and —$NR_q^+$—, —CN, —NC, —CHOCH—, —NHC(NH)NH—, —$NO_2$, —NO, —$OPO_3$—, —OH, or combinations thereof; L is a bond, or a $C_{1-12}$ branched, unbranched, or cyclic hydrocarbyl;

R is hydrogen, $C_{5-10}$ monocyclic or bicyclic aryl or heteroaryl, $C_{1-12}$ branched, unbranched, or cyclic hydrocarbyl, optionally substituted with halo, nitro, or alkyl;

P is

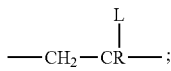

and wherein the order of [—$CH_2$—CR-L-A-$P_r$] and [—$CH_2$—CR-L-Q-R—$P_r$] is random, block or a combination thereof, described in U.S. Patent Application Publication No. 20060247361 to Shah.

In addition, the polymeric sorbents described above can be utilized in the present devices and methods without a porous substrate, for example, formed as beads or fibers. In yet other embodiments, the sorbent can be a polymeric sorbent as described in U.S. Pat. Nos. 6,576,767 and 6,825,269 to Gottschall and available through instrAction GmbH (Ludwigshafen, DE), which describe the preparation of polymeric networks having functional groups on silica. The performance of certain of these sorbents is illustrated in Examples 2 and 4.

In yet other embodiments, the sorbent can be a functionalized monolithic sorbent, comprising a glass fiber matrix embedded with a bonded phase comprising metal oxide or metalloid oxide particles having reactive metal oxides capable of reacting with silanes, such as alkoxysilanes, aminosilanes, hydroxysilanes or halosilanes, such as described in U.S. Patent Application Publication No 20060216206 to Hudson. Suitable metal oxides and metalloid oxides include silica, alumina, zeolite, mullite, zirconia, vanadia or titania, or mixtures or composites thereof, preferably silica. Likewise, the glass fiber matrix is composed of a metal or metalloid oxide. After reaction with a silane, the silane is covalently attached to silica particle via an oxygen linkage, and the metal or metalloid oxides are functionalized by, for example, hydrocarbyl, amido, carbamyl, carbamato, urethane, carbamido, isocyanato, diol, glycidoxy, ethoxy, propoxy, carbonyl, carboxy, acetonyl, thio, dithio, hydroxy, ether, sulfinyl, sulfonyl, sulfonic acid, sulfate, sulfonamido, amino, nitrilo, isonitrilo, epoxy, guanidino, nitro, nitroso, and phosphate.

The silica can be chemically treated (or functionalized) by any method known in the art. In one embodiment, the silica is bonded with alkyl moieties, typically $C_{2-30}$ alkyl groups, to render the silica hydrophobic and provides a reversed phase for adsorption of hydrophobic compounds. In another embodiment, the silica is bonded with a C18 bonded phase with an amide endcapping reagent or a C18 bonded phase having a polar embedded moiety and provides a polar modified reverse phase. Any bonded phase that can be used to modify silica is possible, such as amino, cyano, glycidyl, and the like, as well as anion or cation exchange groups, as discussed above. In a preferred embodiment, the functionalized monolithic sorbent is comprised of glass microfibers impregnated with modified silica, preferably prepared using organosilane chemistries (available from Varian, Inc., Palo Alto, Calif.), which are similar to the SPEC® product. This monolithic bonded silica allows greatly improved flow and much less void volume and less solvent is used in sample processing. The binding capacity of the functionalized monolithic sorbent is generally in the range of about 1 microgram analyte per 0.1 mg sorbent. The glass fiber matrix material typically is constructed from randomly distributed fibers which create a tortuous path of nominally rated size, and has a thickness of from about 0.1 mm to about 2 mm, more typically about 1 mm. In a preferred embodiment, the sorbent is that utilized in Spec® IQe (Varian, Inc., Palo Alto, Calif.).

In additional embodiments, the sorbent can comprise a phospholipotropic multivalent cation coupled to a support, such as described in U.S. Patent Application Publication No. 20050054077 (Bennett, et al.) for removing phospholipids from biological samples. Such sorbents comprise transition metals, lanthanides or actinides, preferably cerium, for adsorbing phosphate containing compounds such as phospholipids.

C. Filtering Means

Particles sizes vary in protein precipitated samples depending on protein concentration and composition, protein precipitation method used, and the like. The use of various denaturing solvents with plasma samples is typical in the analytical laboratory, and particles to be removed from plasma samples likewise vary. In another aspect, the devices and methods described herein provide a filtering means for removing protein precipitated particles from a bioanalytical sample. In especially preferred embodiments, the devices and methods remove protein particulates resulting from precipitation procedures such as the addition of denaturing solvents or salts.

The particle sizes of the protein precipitate can vary depending on composition, method of precipitation and other variables, and thus the filtering means can be chosen to provide the desired particle size removal. For example, when using ACN, precipitated protein particle diameters are generally larger, and therefore, filters having pore sizes of about 0.2 µm to about 0.45 µm are generally sufficient to remove unwanted particulate contaminants; when using MeOH, particle diameters tend to be smaller, and therefore pore sizes in filters of 0.1 µm to 0.2 µm or less are typically sufficient. As shown in Example 7, plasma samples precipitated with 75% (v/v) MeOH/3% formic acid produced smaller particle sizes which could be removed using 0.2 μm pore size Captiva® filters. In contrast, plasma samples precipitated with 75% (v/v) ACN produced larger particle sizes that could be removed using 0.45 μm pore size Captiva® filters.

In certain embodiments, the filtering means is effective to provide optical clarity to the protein precipitated bioanalytical sample (e.g., (% T at 524 nm>95). Preferably, the filtering means is characterized in having pore sizes between about 0.05 μm and about 0.5 μm in diameter for removing precipitated protein particles present in the sample. In certain preferred embodiments, the filtering means is characterized in having pore sizes between about 0.1 μm and about 0.2 μm in diameter. In particularly preferred embodiments, the filtering means is a size exclusion membrane excluding particles greater than 0.2 μm and 0.45 μm in diameter from passage through the filter.

In alternative embodiments, the filtering means is an inorganic monolith having a maximum pore size less than or equal to the diameter of the particles to be removed from the sample, e.g., having pore sizes between about 0.05 μm and about 0.5μm in diameter or more preferably between about 0.1 μm and about 0.2 μm in diameter. In certain other preferred embodiments, the filtering means is integral with the sorbent or associated with the sorbent, for example, a porous inorganic monolith having macropores of a diameter sufficiently small so as to exclude particles from the sample, and comprising a reversed phase or polar modified reversed phase bonded to the porous inorganic monolith.

Preferably, the filtering means is a size exclusion filter such as a Captiva® filter or a Captiva® plate (96 well format). The size exclusion filter can comprise any material known in the art that is stable to the solvent conditions utilized in the protein precipitation and removal of matrix interfering agents. Suitable materials for a size exclusion filter include, without limitation, polyolefinic materials such as polypropylene, polyethylene, poly(4-methylbutene), or copolymers thereof, nylon, PTFE, fluorinated polymers, polysulfone, polyethersulfone, cellulose acetate, polystyrene, polystyrene/acrylonitrile copolymer, PVDF, nitrocellulose, poly(vinyl chloride), polyacrylamide, polyacrylate, polystyrene, polymethacrylate, poly(ethylene terephthalate), poly(vinyl butyrate), etc.; either used by themselves or in combination, and in conjunction with other materials such as glass, ceramics, metals, and the like. The size exclusion filters should be constructed from materials that will not dissolve or leach contaminants into the sample. Preferably, the filters are constructed from ultra-clean polymers, preferably polypropylene, PVDF, or PTFE. In a preferred embodiment, the filtering means is a PTFE filter, which provides the added benefit of retaining the solvent until the user initiates elution of the sample through the filter (e.g., by applying pressure, a vacuum or centrifugal force), providing improved control over timing and providing additional ease of use.

In additional embodiments, the filtering means can be a polymeric or inorganic monolith (as well as a size exclusion filter) having a maximum pore size sufficient to remove the desired size particles. Typically, the maximum pore size that is sufficient to remove the desired size particles is smaller than the diameter of the particles to be removed from the sample. However, in monolithic filter means providing a tortuous path for fluid flow through throughpores (macropores), the maximum pore size that is sufficient to remove the desired size particles may be larger than the diameter of the particles to be removed from the sample. In preferred embodiments, the filtering means is a porous glass monolith, for example, prepared as described in U.S. Patent Application Publication No. 20060131238 to Xu. One skilled in the art can readily determine the size of pores desirable to remove particles of a given size from samples, for example, resulting from protein precipitation in different solvents, salts or acids. One skilled in the art can also readily prepare monolithic filtering means for removing particles of a chosen size.

D. Protein Precipitation Treatments

The skilled artisan will be aware of numerous protein precipitation treatments that can be utilized in the methods of the present invention. Typical treatments that can be utilized to precipitate proteins include acid treatment (e.g., trichloroacetic acid, formic acid, etc.), denaturing solvents (e.g., methanol, acetonitrile, acetone, etc.), heat treatment (resulting in denaturation of the proteins), salt treatments (e.g., ammonium sulfate), and combinations thereof. The devices and methods described herein are preferably utilized with samples wherein the protein precipitation is effected by the addition of denaturing solvents (usually at least 2:1 organic solvent to water). For example, a 2:1 or a 3:1 dilution of an aqueous sample with an organic solvent such as methanol, acetone, or acetonitrile, will result in the precipitation of proteinaceous components found in bioanalytical samples such as plasma, cell culture supernatants, tissue extracts, tissue homogenates, and the like. Thus, precipitated samples typically comprise 50% (v/v) or greater organic phase (e.g., 66% (v/v) for 2:1 dilution with solvent or 75% (v/v) for 3:1 dilution with solvent). In preferred embodiments, the proteins are precipitated using a combination of acid treatment and solvent dilution (e.g., 2:1 methanol, 1% formic acid). The inclusion of acid is advantageous when the analytes of interest are basic analytes, as is typical when performing pharmacokinetic analyses and the like. One skilled in the art will recognize that precipitation conditions will be tailored to the particular analytes of interest and nature of the particular bioanalytical samples. Under certain conditions, it can be advantageous to perform the precipitation in a basic solution, for example, by including a base such as ammonium formate, etc. in the precipitation solution.

E. Matrix Interfering Agents

Matrix interfering agents include a wide variety of substances that can be present in a bioanalytical sample in the relatively high concentration (usually at least 1 mg/ml) necessary to suppress the ionization of an analyte present in the sample during electrospray ionization for mass spectrometric analysis. Matrix interfering agents exert suppression of analyte detection that is very analyte dependent, meaning that detection of one analyte may be affected more adversely than detection of another.

Commonly encountered matrix interfering agents include surfactants and other agents added to samples, lipids present in serum, excipients (dosing agents) added to a drug formulation, and the like. For example, NP 40 can be added to cultured cells to lyse the cells prior to analysis of a sample. Blood plasma from patients or experimental animals is known to contain significant amounts of lipids such as cholesterol, triglycerides, phospholipids, lysophospholipids, lipoproteins, and the like, all of which can be present at sufficiently high concentrations to exert matrix interfering effects, and/or to contaminate analytical instrumentation. Polyethylene glycol (PEG), surfactants, disintegrants, and other excipients can be present in dissolution studies of drug formulations.

Surfactants and plasma lipids are some of the most common matrix interfering agents encountered in bioanalytical testing. Plasma lipids that can be removed using the presently described devices and methods include cholesterol, cholesterol esters, triglycerides, phospholipids, lysophospholipids, lipoproteins, and the like, without limitation, so long as the sorbent exhibits a selectivity for the plasma lipid over analytes of interest that is greater than 1. A preferred plasma lipid is phosphatidylcholine (PC), which can be present as the lyso form (having only one acyl chain), or the diacyl form (having two acyl chains).

Surfactants that can be removed using the presently described devices and methods include a wide variety of surfactants, including nonionic surfactants as well as ionic surfactants, including cationic surfactants, anionic surfactants or zwitterionic surfactants. Nonionic surfactants include, for example, polyoxyl stearates such as polyoxyl 40 stearate, polyoxyl 50 stearate, polyoxyl 100 stearate, polyoxyl 12 distearate, polyoxyl 32 distearate, and polyoxyl 150 distearate, and other Myrj™ series of surfactants, triblock co-polymers of ethylene oxide/propylene oxide/ethylene oxide, also known as poloxamers, having the general formula $HO(C_2H_4O)_a(-C_3H_6O)_b(C_2H_4O)_aH$, available under the tradenames Pluronic and Poloxamer, sugar ester surfactants, sorbitan fatty acid esters such as sorbitan monolaurate, sorbitan monopalmitate, sorbitan monostearate, sorbitan tristearate, and other Span™ series surfactants, glycerol fatty acid esters such as glycerol monostearate, polyoxyethylene derivatives such as polyoxyethylene ethers of high molecular weight aliphatic alcohols (e.g., Brij 30, 35, 58, 78 and 99) polyoxyethylene stearate (self emulsifying), polyoxyethylene 40 sorbitol lanolin derivative, polyoxyethylene 75 sorbitol lanolin derivative, polyoxyethylene 6 sorbitol beeswax derivative, polyoxyethylene 20 sorbitol beeswax derivative, polyoxyethylene 20 sorbitol lanolin derivative, polyoxyethylene 50 sorbitol lanolin derivative, polyoxyethylene 23 lauryl ether, polyoxyethylene 2 cetyl ether with butylated hydroxyanisole, polyoxyethylene 10 cetyl ether, polyoxyethylene 20 cetyl ether, polyoxyethylene 2 stearyl ether, polyoxyethylene 10 stearyl ether, polyoxyethylene 20 stearyl ether, polyoxyethylene 21 stearyl ether, polyoxyethylene 20 oleyl ether, polyoxyethylene 40 stearate, polyoxyethylene 50 stearate, polyoxyethylene 100 stearate, polyoxyethylene derivatives of fatty acid esters of sorbitan such as polyoxyethylene 4 sorbitan monostearate, polyoxyethylene 20 sorbitan tristearate, and other Tween™ series of surfactants, phospholipids and phospholipid fatty acid derivatives such as fatty amine oxides, fatty acid alkanolamides, propylene glycol monoesters and monoglycerides, such as hydrogenated palm oil monoglyceride, hydrogenated soybean oil monoglyceride, hydrogenated palm stearine monoglyceride, hydrogenated vegetable monoglyceride, hydrogenated cottonseed oil monoglyceride, refined palm oil monoglyceride, partially hydrogenated soybean oil monoglyceride, cotton seed oil monoglyceride sunflower oil monoglyceride, sunflower oil monoglyceride, canola oil monoglyceride, succinylated monoglycerides, acetylated monoglyceride, acetylated hydrogenated vegetable oil monoglyceride, acetylated hydrogenated coconut oil monoglyceride, acetylated hydrogenated soybean oil monoglyceride, glycerol monostearate, monoglycerides with hydrogenated soybean oil, monoglycerides with hydrogenated palm oil, succinylated monoglycerides and monoglycerides, monoglycerides and rapeseed oil, monoglycerides and cottonseed oils, monoglycerides with propylene glycol monoester sodium stearoyl lactylate silicon dioxide, diglycerides, triglycerides, polyoxyethylene steroidal esters, Triton-X series of surfactants produced from octylphenol polymerized with ethylene oxide, where the number "100" in the trade name is indirectly related to the number of ethylene oxide units in the structure, (e.g., Triton X-100™ has an average of N=9.5 ethylene oxide units per molecule, with an average molecular weight of 625) and having lower and higher mole adducts present in lesser amounts in commercial products, as well as compounds having a similar structure to Triton X-100™, including Igepal CA-630™ and Nonidet P-40M (NP-40™, N-lauroylsarcosine, Sigma Chemical Co., St. Louis, Mo.), and the like. Any hydrocarbon chains in the surfactant molecules can be saturated or unsaturated, hydrogenated or unhydrogenated.

Sugar ester surfactants include sugar fatty acid monoesters, sugar fatty acid diesters, triesters, tetraesters, or mixtures thereof, although mono- and di-esters are most preferred. Preferably, the sugar fatty acid monoester comprises a fatty acid having from 6 to 24 carbon atoms, which may be linear or branched, or saturated or unsaturated $C_6$ to $C_{24}$ fatty acids. The $C_6$ to $C_{24}$ fatty acids are preferably chosen from stearates, behenates, cocoates, arachidonates, palmitates, myristates, laurates, carprates, oleates, laurates and their mixtures, and can include even or odd numbers of carbons in any subrange or combination. Preferably, the sugar fatty acid monoester comprises at least one saccharide unit, such as sucrose, maltose, glucose, fructose, mannose, galactose, arabinose, xylose, lactose, sorbitol, trehalose or methylglucose. Disaccharide esters such as sucrose esters are most preferable, and include sucrose cocoate, sucrose monooctanoate, sucrose monodecanoate, sucrose mono- or dilaurate, sucrose monomyristate, sucrose mono- or dipalmitate, sucrose mono- or distearate, sucrose mono-, di- or trioleate, sucrose mono- or dilinoleate, sucrose polyesters, such as sucrose pentaoleate, hexaoleate, heptaoleate or octooleate, and mixed esters, such as sucrose palmitate/stearate.

Sugar ester surfactants include those sold by the company Croda Inc of Parsippany, N.J. under the names Crodesta F10, F50, F160, and F110 denoting various mono-, di- and mono/di ester mixtures comprising sucrose stearates, manufactured using a method that controls the degree of esterification, such as described in U.S. Pat. No. 3,480,616, those sold by the company Mitsubishi under the name Ryoto Sugar esters, for example under the reference B370 corresponding to sucrose behenate formed of 20% monoester and 80% di-, tri- and polyester, sucrose mono- and dipalmitate/stearate sold by the company Goldschmidt under the name "Tegosoft PSE", sugar esterspresent in admixture with another compound not derived from sugar; such as the mixture of sorbitan stearate and of sucrose cocoate sold under the name "Arlatone 2121" by the company ICI, other sugar esters such as, for example, glucose trioleate, galactose di-, tri-, tetra- or pentaoleate, arabinose di-, tri- or tetralinoleate or xylose di-, tri- or tetralinoleate, or mixtures thereof. Other sugar esters of fatty acids include esters of methylglucose include the distearate of methylglucose and of polyglycerol-3 sold by the company Goldschmidt under the name of Tegocare 450. Glucose or maltose monoesters can also be included, such as methyl O-hexadecanoyl-6-D-glucoside and O-hexadecanoyl-6-D-maltose. Certain other sugar ester surfactants include oxyethylenated esters of fatty acid and of sugar include oxyethylenated derivatives such as PEG-20 methylglucose sesquistearate, sold under the name "Glucamate SSE20", by the company Amerchol.

III. Methods for Bioanalytical Sample Preparation

The invention further provides methods for preparing a sample comprising matrix interfering agents and proteins for analysis. One skilled in the art will recognize that the devices and methods of the present invention can be implemented in various fashions to remove precipitated proteins and reduce matrix effects. Typical analyses include chromatographic, spectrophotometric, mass spectrometric, and the like, and combinations thereof. For example, an exemplary analysis method in the bioanalytical arts for determining pharmaceutical analytes is LC/MS-MS.

Accordingly, there are provided methods for reducing matrix effects and removing protein precipitates in a bioanalytical sample, said methods comprising: a) providing a device comprising a support, and a sorbent associated with the support, wherein said sorbent is characterized by a selectivity greater than 1 for matrix interfering agents relative to analytes of interest present in the bioanalytical sample, and further comprising filtering means for removing protein precipitates present in the sample; b) contacting the bioanalytical sample with the sorbent; and c) eluting the analytes from the sorbent while retaining the matrix interfering agents and precipitated proteins, wherein the amount of matrix interfering agents and proteins in the resulting treated sample is reduced. In certain embodiments, the method can further comprise precipitating the proteins in the bioanalytical sample in the device prior to or simultaneously with the step of contacting the bioanalytical sample with the sorbent. Preferably, step c) is performed using negative pressure (i.e., applying a vacuum), electrokinetic or centrifugal force, gravity- or capillary-driven or positive pressure to cause the sample to pass through the sorbent and the filtering means, thereby removing matrix interfering agents and precipitated proteins. For example, negative pressure can be used to pull samples through 96 well plates or cartridges using vacuum manifolds commerically available. Positive pressure can be used to push samples through, without limitation, an in line column or single use cartridge, pipette tips, or a luer based syringe filter. Similarly, centrifugal force can be used (a centrifuge) to push samples through filter cartridges or 96 well plates and the like.

Preferably, the filtering means is characterized in having pore sizes between about 0.05 μm and about 0.5 μm in diameter for removing precipitated protein particles present in the sample, and in certain embodiments, the filtering means comprises pore sizes between about 0.1 μm and about 0.2 μm. In particular embodiments, the filtering means comprises pores sizes of 0.1, 0.2 and 0.45 μm. Preferably, the matrix interfering agents are surfactants, lipids, excipients, or dosing agents, and in preferred embodiments, the lipids are phospholipids, and the surfactants are selected from anionic surfactants or nonionic surfactants. Preferably the surfactants comprise a hydrocarbon chain which can be advantageously retained using the sorbents described herein. Preferably, the sorbent is characterized by sufficient selectivity between the matrix interfering agents and analytes of interest to provide retention of the matrix interfering agents while providing elution of the analytes of interest. In certain embodiments, the sorbent comprises a reversed phase or a polar modified reversed phase. In particular embodiments, there are provided methods for reducing matrix effects and removing precipitated proteins in a protein precipitated bioanalytical sample comprising matrix interfering agents and analytes of interest, the method comprising passing the sample through the devices described herein.

In additional embodiments, methods are provided for reducing matrix effects in a protein precipitated bioanalytical sample comprising matrix interfering agents and analytes of interest, the method comprising: a) providing a device comprising a support, and a sorbent associated with the support, wherein said sorbent is characterized by a selectivity greater than 1 for matrix interfering agents relative to analytes of interest present in the bioanalytical sample; b) contacting the bioanalytical sample with the sorbent; and c) eluting the analytes from the sorbent while retaining the matrix interfering agents, wherein the amount of matrix interfering agents in the resulting treated sample is reduced. The device can further comprise filtering means for removing precipitated protein particles. In preferred embodiments, when the bioanalytical sample comprises at least 50% (v/v) denaturing organic solvent, the sorbent retains matrix interfering agents while not retaining analytes of interest. In additional embodiments, the sorbent retains matrix interfering agents while not retaining analytes of interest even at 66%, 75%, or even 90% (v/v) organic solvent, or in the presence of pH modifiers (e.g., acids, bases). Preferably, the sorbent binds at least 50% of the matrix interfering agents present in the bioanalytical sample, while providing recovery of at least 90% of the analytes in the solvent output from the device, and more preferably, the sorbent binds at least 70%, or more preferably 85%, or more preferably 90%, or even more preferably 95%, and most preferably 99% of the matrix interfering agents present in the sample.

In certain embodiments, the devices can be used in a combination filtration and solid phase extraction mode (SPE). For example, the methods can further comprise optionally conditioning the sorbent by washing the sorbent with at least one conditioning solvent or mixture of solvents prior to contacting the bioanalytical sample with the sorbent. The methods can further comprise optionally washing the sorbent with adsorbed analytes and matrix interfering agents with a wash solvent or mixture of solvents to remove unbound components. In accordance with further SPE uses, the methods can further comprise eluting analytes from the sorbent with eluting solvents of sequentially increasing solvent strength to remove more nonpolar analytes without contaminating the analytes with the adsorbed matrix interfering agents.

In an additional embodiment, a method is provided for reducing matrix effects in a bioanalytical sample comprising at least 50% (v/v) protein denaturing organic solvent, the method comprising: a) providing a sorbent capable of binding matrix interfering agents present in the bioanalytical sample; b) contacting the bioanalytical sample with the sorbent for at least 10 seconds; and c) separating the solution from the sorbent, wherein the amount of matrix interfering agents in the resulting treated sample is reduced. Preferably, said contacting is performed for from about 10 seconds to about 10 minutes, and the sorbent binds at least 50% of the matrix interfering agents present in the bioanalytical sample, while providing recovery of at least 90% of the analytes in the solvent output from the device. The method can further comprise contacting the bioanalytical sample with a filtering means for removing precipitated protein particles. Preferably, the contacting with a filtering means and with the sorbent is done in the same step.

In another embodiment, a sample is subjected to a protein precipitation treatment followed by centrifugation, or does not contain sufficient protein to warrant removal prior to analysis, and subsequently is treated with the sorbent with selectivity for matrix interfering agents, e.g., the supernatant is transferred from the protein pellet using a pipette tip loaded with the sorbent. A pipette tip implementation suitable for performing the method is depicted in FIG. 1.

In preferred embodiments, the method is utilized to reduce matrix effects in a sample containing analytes of varying log P, but particularly log P values over 2, the sorbent is a polar modified reversed phase sorbent and is used in high organic solvent strengths (e.g., 50% (v/v) to 95% (v/v)) with or without a pH modifier and with a filter pore size of 0.2 μm. For example, the method can comprise performing a precipitation using 2:1 or 3:1 volume dilutions ACN or 3:1 MeOH for plasma samples containing analytes having log P values≤5.2 and approximately 20 mg-30 mg sorbent such as Polaris® C18-A or C18 Amide to remove particulates of protein and phosphatidylcholines and surfactants. With the higher amount of sorbent, most of the lysophosphatidylcholines can be removed.

In additional preferred embodiments, the method is utilized to reduce matrix effects in a sample containing analytes of varying log P, the sorbent (20-30 mg) is a reversed phase sorbent or a polar modified reversed phase sorbent and is used with 66% (v/v) organic solvent strengths and a filter pore size of 0.1-0.2 µm. For example, the method comprises performing a precipitation using 2:1 MeOH with 3% formic acid for plasma samples containing analytes to remove particulates of protein and substantially all phosphatidylcholines, including lysophosphatidylcholines, and surfactants such as Tween 80 and SDS. This amount of sorbent (20 mg) is sufficient to remove 5 mg/ml surfactants without affecting recovery of analytes from plasma samples (approximately less than 1 ml). Aspects of this embodiment are illustrated in Examples 5, 7 and 11 and FIG. 17.

Very nonpolar analytes such as posaconazole can show inconsistent recovery with some solvents and pH conditions tested (see Example 9). One skilled in the art will recognize that the solvent, sorbent, solvent strength and pH can be optimized for recovery of very nonpolar analytes, while possibly sacrificing removal of certain matrix interfering agents. Similarly, removal of all matrix interfering agents can be achieved to produce a cleaner sample while possibly sacrificing recovery of all analytes. Depending on the analytical objectives, compromising removal of all matrix constituents can be acceptable if on balance, the analyte can be quantitated more reliably. Similarly, compromising analyte recovery can be desirable if on balance, more accurate quantitation is possible having achieved a significantly cleaner sample.

IV. Methods for Preparing a Device for Reducing Matrix Effects in Bioanalytical Samples.

In additional embodiments, methods are provided for preparing devices for reducing matrix effects in a bioanalytical sample. In one embodiment, a method is provided for preparing a device for reducing matrix effects in a bioanalytical sample, comprising the following steps: a) providing a support capable of containing a quantity of sorbent and a filtering means; and b) providing an amount of sorbent effective to retain matrix interfering agents present in the sample, and a filtering means for removing precipitated proteins present in the sample; and c) assembling the filtering means and the sorbent within the support. The method can further comprise providing a retaining means for the sorbent to hold it in place in the support, and/or supporting means for the filtering means to hold it in place in the support. In additional embodiments, the support further comprises a reservoir capable of containing the bioanalytical sample and solvent added to precipitate proteins. In a particular embodiment, a device is prepared for reducing matrix effects in a bioanalytical sample comprising the following steps: a) providing a support capable of supporting a size exclusion filter and capable of containing a quantity of sorbent and a bioanalytical sample; b) assembling a size exclusion filter within the support; c) assembling the sorbent into the support on top of the size exclusion filter; and d) optionally providing a retaining means for the sorbent to hold it in place in the support.

The following devices and method for preparation are non-limiting examples of devices that can be prepared and utilized for reducing matrix effects and precipitated proteins in bioanalytical samples.

1. A device for use in a multiwell format can be prepared comprising the following steps: preparing a slurry of 10 mg/ml Polaris® C18-A (10 µm) in MeOH and adding 2 ml (20 mg) to each well of a Captiva® 96 well plate including a 0.2 µm size exclusion filter (polypropylene); removing the MeOH by suction through the filters, and placing a frit on top of each sorbent bed. The device is then ready for use.

2. A device for use as an individual filter cartridge can be prepared comprising the following steps: providing an individual filter cartridge with a frit for supporting a size exclusion membrane, assembling the filter onto the frit, and further assembling a second frit on top of the membrane to secure it, applying sorbent on top of the second frit as a slurry in MeOH (20 mg from a 10 mg/ml slurry), removing the MeOH, and applying a third frit to the top of the sorbent to secure the sorbent.

3. A device for inline use can be prepared comprising the following steps: providing a column body of metal or PEEK, inserting a frit in one end followed by the filter means, followed optionally by an additional securing frit; sorbent is inserted as a slurry or dry powder, followed by an additional securing means, capped off using hardware with an appropriate outlet and inlet to interface for use with a column. Alternatively, a sol gel monolith can be prepared in a column body, dried, calcinated and modified to provide a desired bonded phase, and equipped with the necessary hardware for inline use.

4. A device for use in a pipette tip format can be prepared comprising the following steps: providing a pipette tip and inserting a filter means into the small opening (the tip) of the pipette tip or by forming a monolithic filter means directly in the pipette tip by in situ polymerization, followed by assembling a plug of glass fiber monolithic sorbent prepared as described in U.S. Patent Application Publication No. 20060216206 to Hudson or alternatively by providing a quantity of particulate or monolithic sorbent into the pipette tip adjacent to the filter means. Pipette tips can also be utilized for reducing matrix effects without utilizing filter means if protein precipitates are not present in the sample, in which case the pipette tips can be prepared as described in U.S. Patent Application Publication No. 20060216206, such as Omix IQe Tomtec tips (Varian, Inc., Palo Alto, Calif.).

5. A device for use as a luer based syringe filter can be prepared in a manner similar to that utilized to prepare a 96 well plate. A luer device can be fitted with a filter means and sorbent of desired selectivity and pore size. For example, the filtering means can be a Captiva® or Millipore filter 0.2 µm pore size and the sorbent can be a Spec® disk (available from Varian, Inc. Palo Alto, Calif.), or a plurality of Spec® disks or a particulate sorbent. The order of the sorbent and filtering means is not important, i.e., the sorbent or the filter can be placed at the female or male end of the device However, it would be conventional to filter out particulates prior to contacting the sample with the sorbent.

The devices can also be prepared by pouring or placing dry sorbent particles or monolithic sorbents (e.g., a functionalized monolithic sorbent comprising a glass fiber matrix embedded with a bonded phase, or a sol gel monolith that is modified to produce a bonded phase, or polymer modified porous substrates, etc.) on top of the filter and/or frit or polymerizing polymer based monolithic sorbents (e.g., polymeric sorbents comprising polar functionalities such as amide functionality) on top of the filter and/or frit.

One skilled in the art will be able to practice and assemble these other similar devices, understanding that the order of contact of the bioanalytical sample with sorbent and filtering means is generally not important. In addition, the devices can include reservoirs for preparing the protein precipitates directly in the device, followed by adsorption and filtration, all in one step, as demonstrated in Example 11. It is preferred that the protein precipitation be performed prior to allowing the sample contact with the sorbent, as protein adsorption could adversely affect the ability of the sorbent to retain matrix interfering agents. However, this is not a necessary condition for use, and one skilled in the art can vary the procedures to determine if it is preferable to perform the precipitation prior to contacting the sample with the sorbent.

One skilled in the art will further be able to substitute similar materials to provide devices having slightly different attributes. For example, any filtering means can be utilized, such as filters from Millipore, Porex, Advantec, and the like, so long as the pore size utilized is appropriate for the application. Similarly, filters of polypropylene, PVDF, PTFE, nitrocellulose, etc., can be utilized, as desired for particular applications. Reversed phase sorbents lacking polar modification can be appropriate when analytes of interest are relatively polar (e.g., log P<2) and are not well retained under the solvent conditions associated with precipitated protein solutions (>50% (v/v) organic solvent).

It is also generally preferred that the device provide for unidirectional flow, that is, that the device have an inlet and outlet side, and the sample is applied to one surface or inlet of the device and the treated sample exit from the outlet or other side of the device, having passed through the sorbent and the filtering means in a unidirectional fashion. However, in certain embodiments, the filtering means can be placed at the entrance to exclude particles from entering the device (e.g., a pipette tip implementation) while the sorbent is placed adjacent the filtering means such that the protein precipitates are filtered out of the sample as they enter the device and then the sample contacts the sorbent and afterwards is ejected back through the filtering means.

In additional embodiments, the sorbent and filtering means are integral with one another, for example, as where the filtering means is a monolithic inorganic substrate (e.g., a sol gel monolith) having macropores of the desired size for excluding precipitated protein particles and is surface modified to produce a reversed or polar modified reversed bonded phase for selectively adsorbing matrix interfering agents from the sample.

V. Applications and Methods of Use

The articles and methods of the present invention can be advantageously used in the preparation of samples for chromatographic and analytical separations applications, where the cleaner sample lacking protein and lipid/surfactant contaminants, for example, does not contaminate chromatographic media and instrumentation, which results in significant down time for cleaning and maintenance, instrument drift and inconsistencies, and even effects on sorbent selectivity and analyte retention times.

The devices can be utilized in conjunction with capillary columns, cartridge systems, or conventional HPLC systems, as well as microfluidics applications. The devices and methods are particularly advantageously applied in the preparation of samples for high throughput screening of plasma analytes (or other protein containing solutions) with mass spectrometric detection of analytes, where the reduction in matrix interfering agents and precipitated proteins performed in a single quick step provides extraordinary convenience and ease of use for the busy laboratory worker. The devices can also be utilized in SPE.

VI. Advantages of the Invention

The inventive combination device comprising protein precipitation filter and a sorbent to remove lipids, surfactants and other matrix interfering agents allows the user to process the sample in a manner similar to that used in a typical protein precipitation/filtration procedure but provides the added benefit of reducing matrix effects as well as removing proteins in one step. Use of the device dramatically simplifies the process of preparing clean bioanalytical samples prior to analysis. A separate sample treatment step utilizing SPE is not necessary. Therefore, use of the combination device provides much more efficient sample preparation, decreases labor and cost and time required for sample analysis.

An exemplary embodiment is described in Examples 10 and 11, and demonstrates the dramatic improvement in sample preparation procedures possible using the devices of the present invention. As described in Example 11, the sample could be subjected to both protein precipitation procedures and stripped of matrix interfering agents (in this case, surfactants and phospholipids) in a single step using a single device and a pipetter. Overall, sample preparation required only a few minutes of time to measure and mix samples plus solvents, then a few seconds to recover the treated samples now ready for immediate analysis.

Accordingly, some advantages and characteristics of the present articles and methods include: ease of use, convenience, one step protein/lipid/surfactant stripping is possible; saving time, solvents, materials, labor and cost.

In the following examples, efforts have been made to ensure accuracy with respect to numbers used (e.g., amounts, temperature, etc.) but some experimental error and deviation should be accounted for. Unless indicated otherwise, temperature is in degrees ° C. and pressure is at or near atmospheric. All solvents were purchased as HPLC grade, and all reactions were routinely conducted in the air unless otherwise indicated.

Abbreviations:
ACN Acetonitrile
LC/MS-MS Liquid chromatography-mass spectrometry/mass spectrometry
SDS Sodium dodecyl sulfate

EXAMPLE 1

Phospholipid Build Up on a Chromatography Column

Dilute porcine plasma was injected into a polar modified C18-A HPLC column (40 mm×4.0 mm), and plasma constituents were eluted using a gradient program of ACN and 0.1% formic acid ramping from 10% to 90% ACN in 1 min after a 40 second hold. High organic elution was held for 40 seconds before returning to 10% to re-equilibrate the column (see Table 13).

Figure 2:
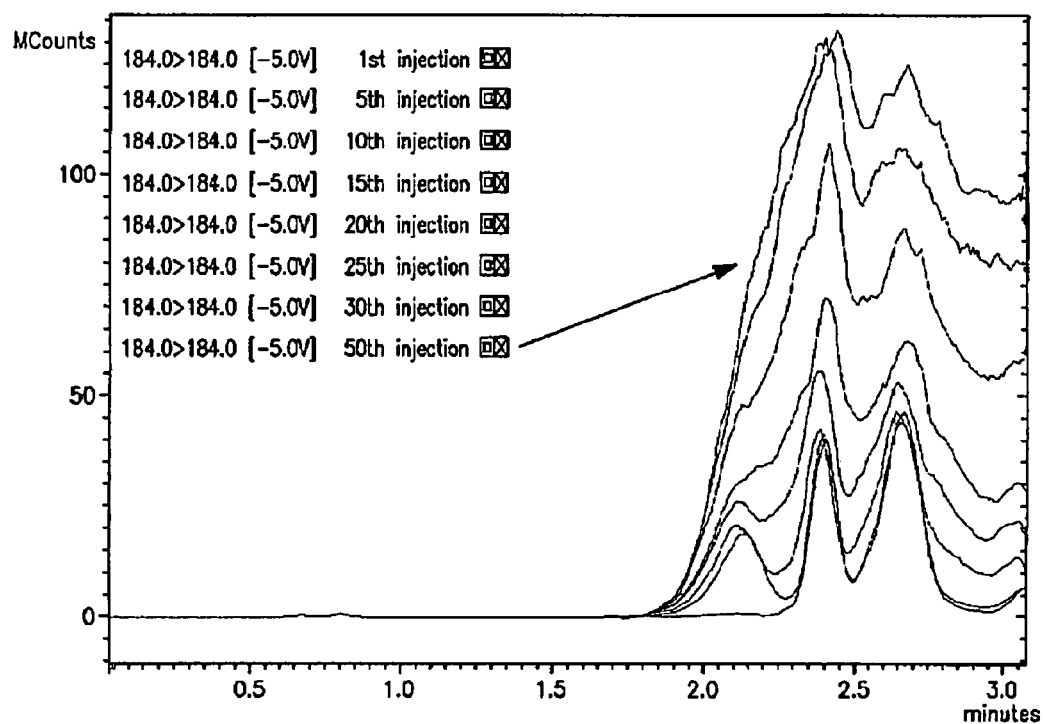
FIG. 2 shows LC-MS/MS traces showing the gradual buildup of phospholipids (phosphatidylcholine) on a HPLC column over the course of 50 injections of dilute plasma.
Figure 3:
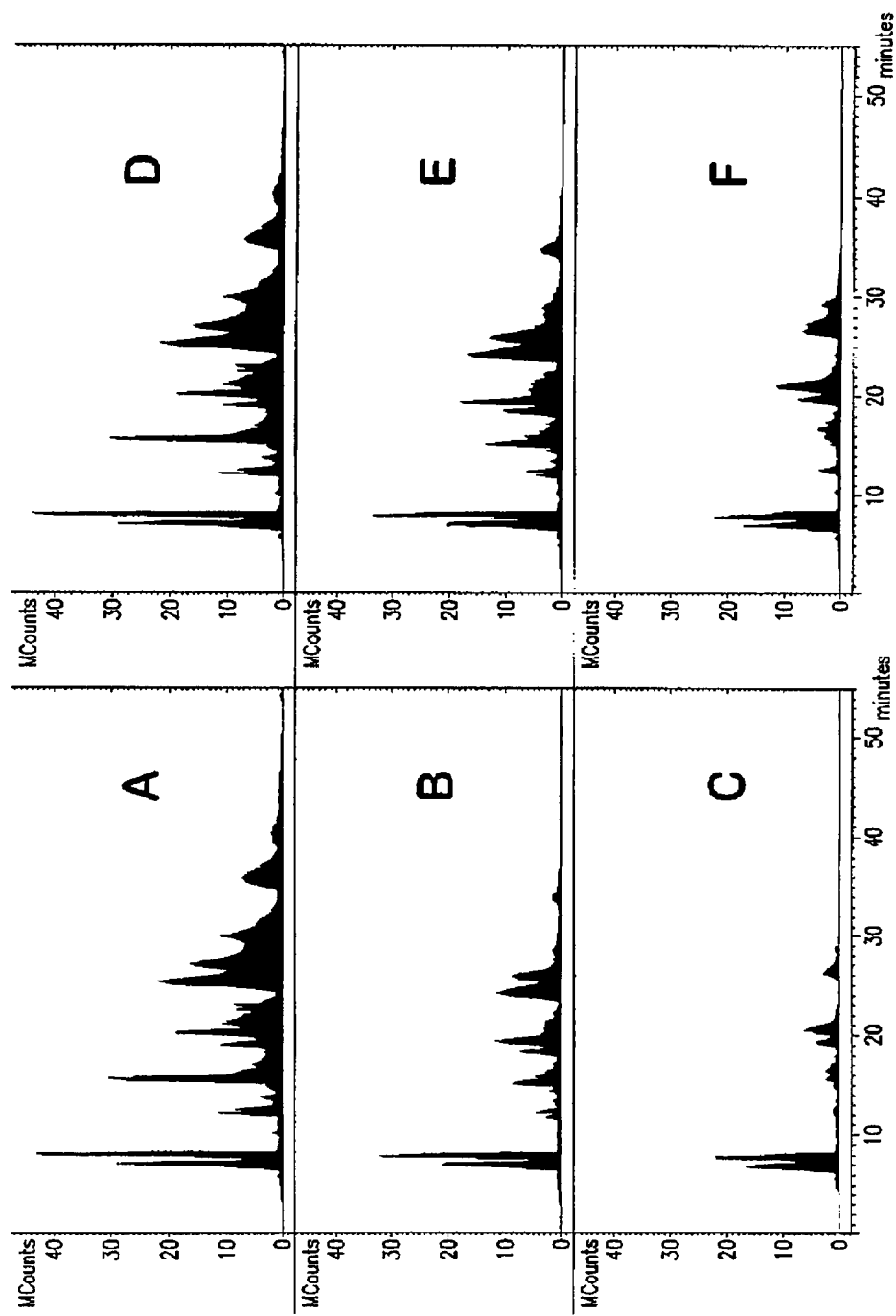
FIG. 3 shows chromatograms of samples subjected to treatment with sorbent relative to untreated samples.

The results are shown in FIG. 2, which demonstrates that the phospholipids (phosphatidylcholine) gradually accumulate on the column over the course of 50 injections. LC-MS/MS traces are shown with detection of the phosphatidylcholine elution at m/z 184.0→184.0 according to the method described by Little (2006)J. Chromatog. 833, 219.

EXAMPLE 2

Correlation of Analyte Detection with Phosphatidylcholine and Tween 80 Removal by Various Sorbents A comparison of the abilities of various sorbents to remove phospholipids and the surfactant Tween 80 was performed. Porcine plasma samples (0.2 ml) were treated to precipitate proteins by the addition of either acetonitrile (ACN) or 1.0% formic acid in ACN (0.6 ml), then centrifuged to remove precipitated proteins (Sorvall 50 ml rotor 5000 rpm 20 min). The supernatants were removed and spiked with the following pharmaceutical analytes: zolpidem, warfarin, quinidine, sulindac, loratadine, loperamide and Tween 80 (5 mg/ml). The spiked plasma samples were then filtered through a test sorbent: either ND 06262, ND 06265, ND 06267 (instrAction GmbH, Ludwigshafen, DE), or Polaris® C18-Amide (Varian, Inc., Palo Alto, Calif.) 10 µm silica beads. Sorbents were assembled on top of a Captiva® 0.45 µm membrane into a collection plate (10 mg or 20 mg sorbents). Ten µl aliquots were analyzed by HPLC using a Varian Polaris® C18-A column (3 µm particle diameter (50 mm×2.0 mm) with a gradient of A: 0.1% formic acid and B: acetonitrile according to Table 1 using a Varian 1200L LC/MS-MS system.

TABLE 1

HPLC Elution Program

| Time | % B | Flow rate (µl/min) |
|---|---|---|
| 0.00 | 10 | 350 |
| 1.00 | 10 | 350 |
| 8:00 | 90 | 350 |
| 53:00 | 90 | 350 |
| 53:01 | 10 | 350 |
| 55:00 | 10 | 350 |

Pharmaceutical analytes, phosphatidylcholine and Tween 80 MS/MS responses were determined for 10 mg or 20 mg sorbent relative to treatment with the filtering membrane alone (control). Quantitation ions were detected by their mass spectrometry transitions as shown in Table 2.

TABLE 2

Analyte molecular ions

| Analytes | MS transition | Collision Energy (V) |
|---|---|---|
| Zolpidem | 308.1 → 235.0 | −28 |
| Warfarin | 309.0 → 163.0 | −11 |
| Quinidine | 325.1 → 160.0 | −21 |
| Sulindac | 357.1 → 233.0 | −41 |
| Loratadine | 383.0 → 337.0 | −22.5 |
| Loperamide | 477.1 → 266.0 | −22 |
| Tween 80 | 309.0 → 309.0 | −5 |
| Phosphatidylcholines | 184.0 → 184.0 | −5 |

Figure 4:
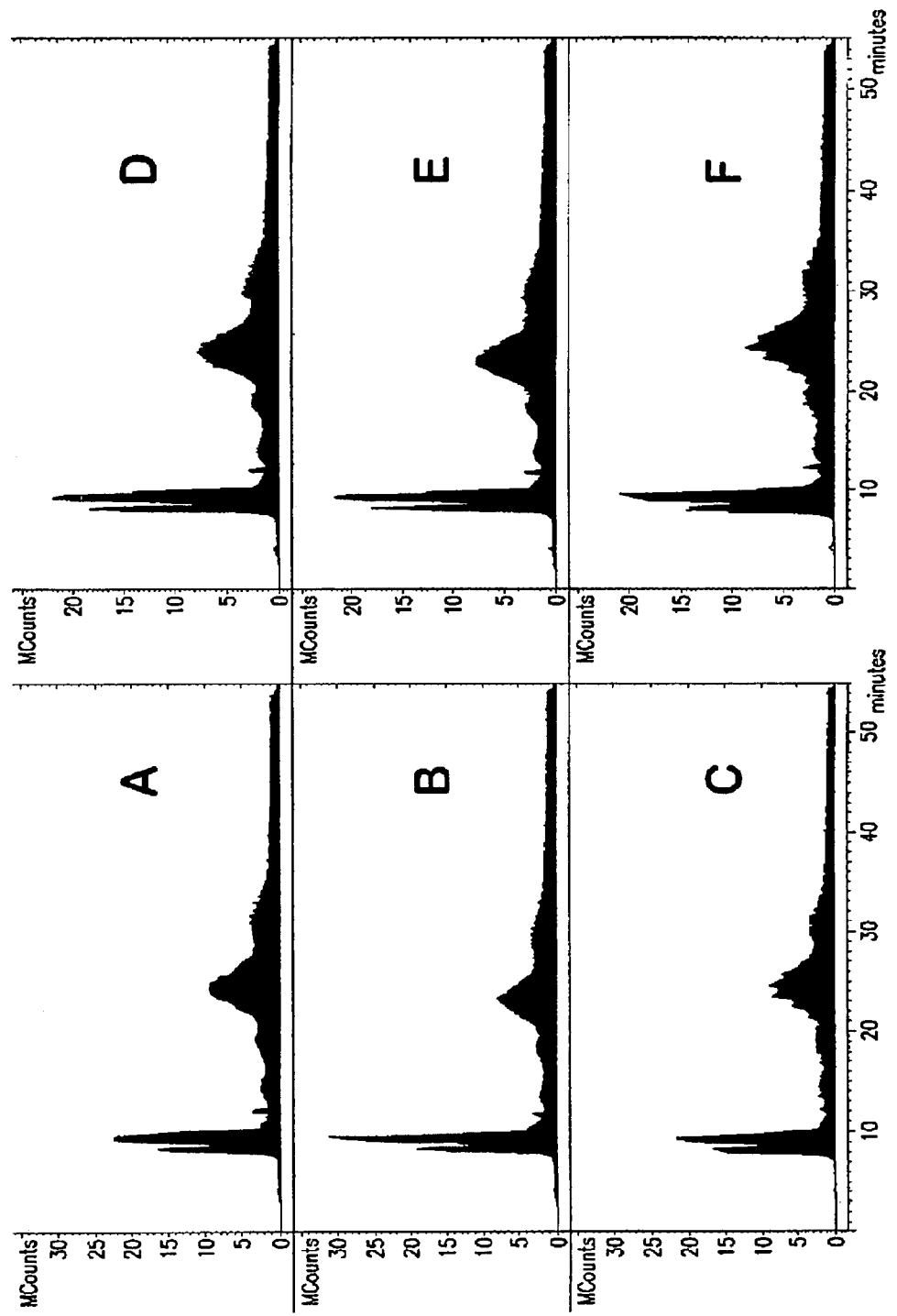
FIG. 4 shows chromatograms of samples subjected to treatment with sorbent relative to untreated samples.
Figure 5:
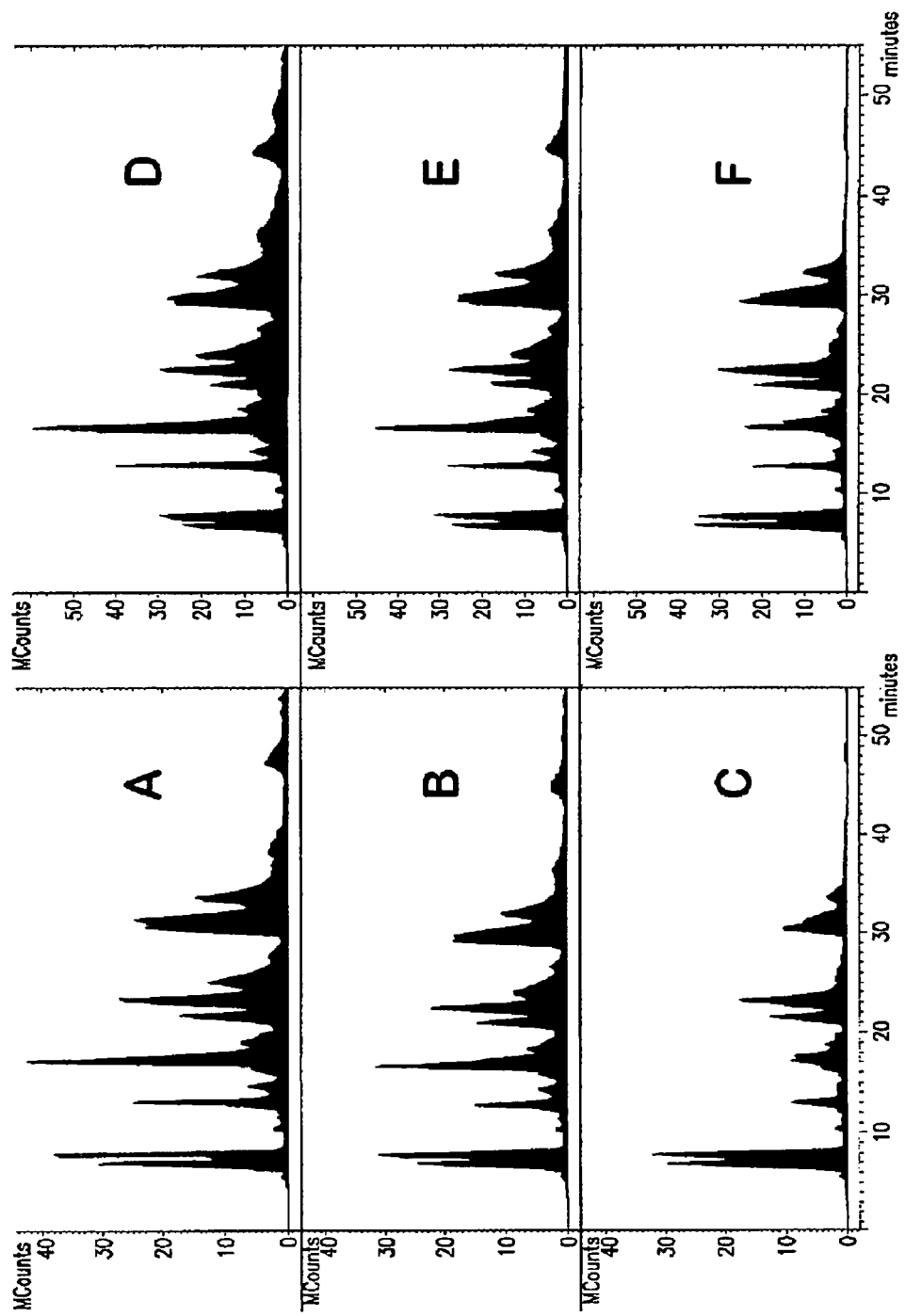
FIG. 5 shows chromatograms of samples subjected to treatment with sorbent relative to untreated samples.
Figure 6:
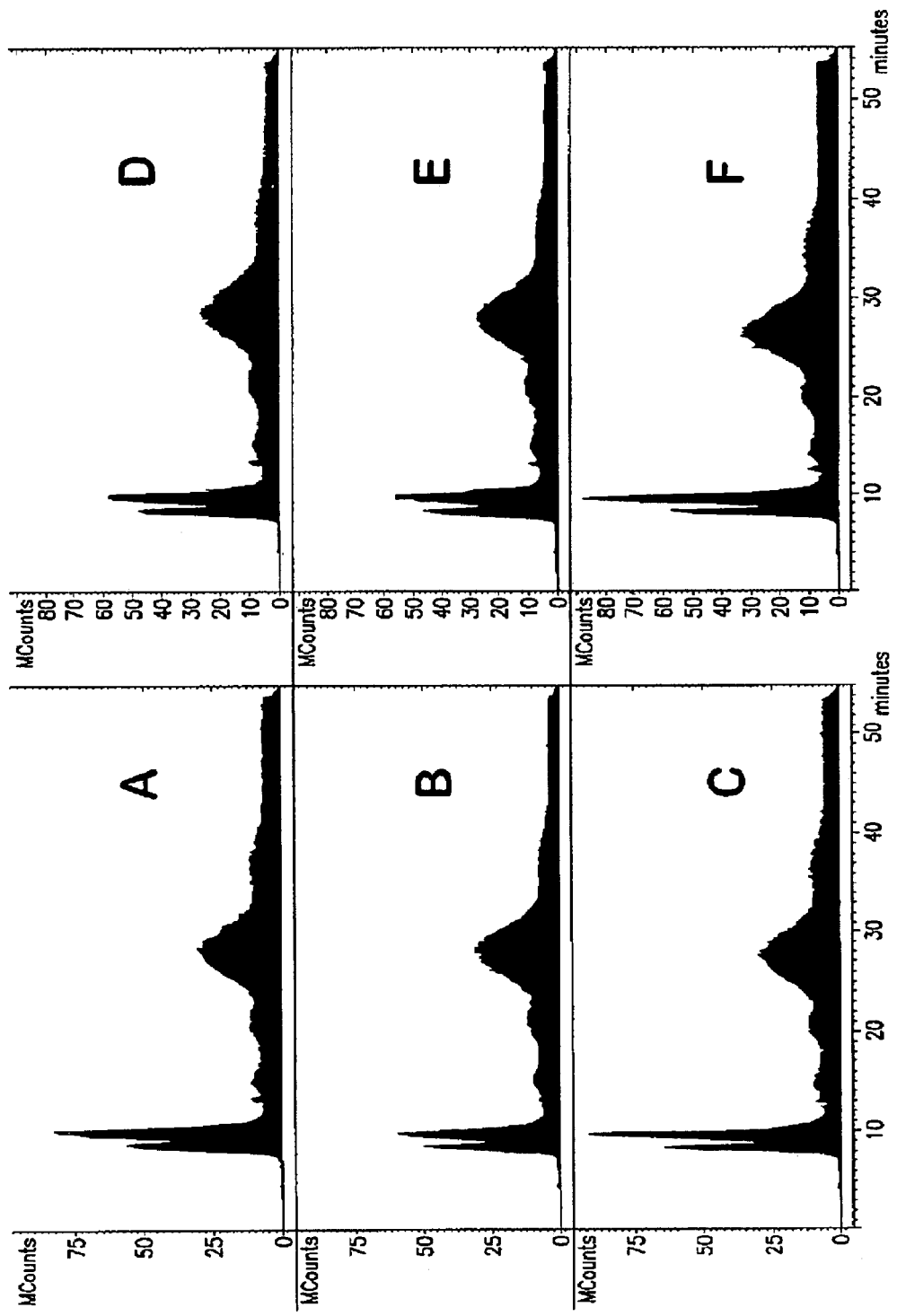
FIG. 6 shows chromatograms of samples subjected to treatment with sorbent relative to untreated samples.
Figure 7:
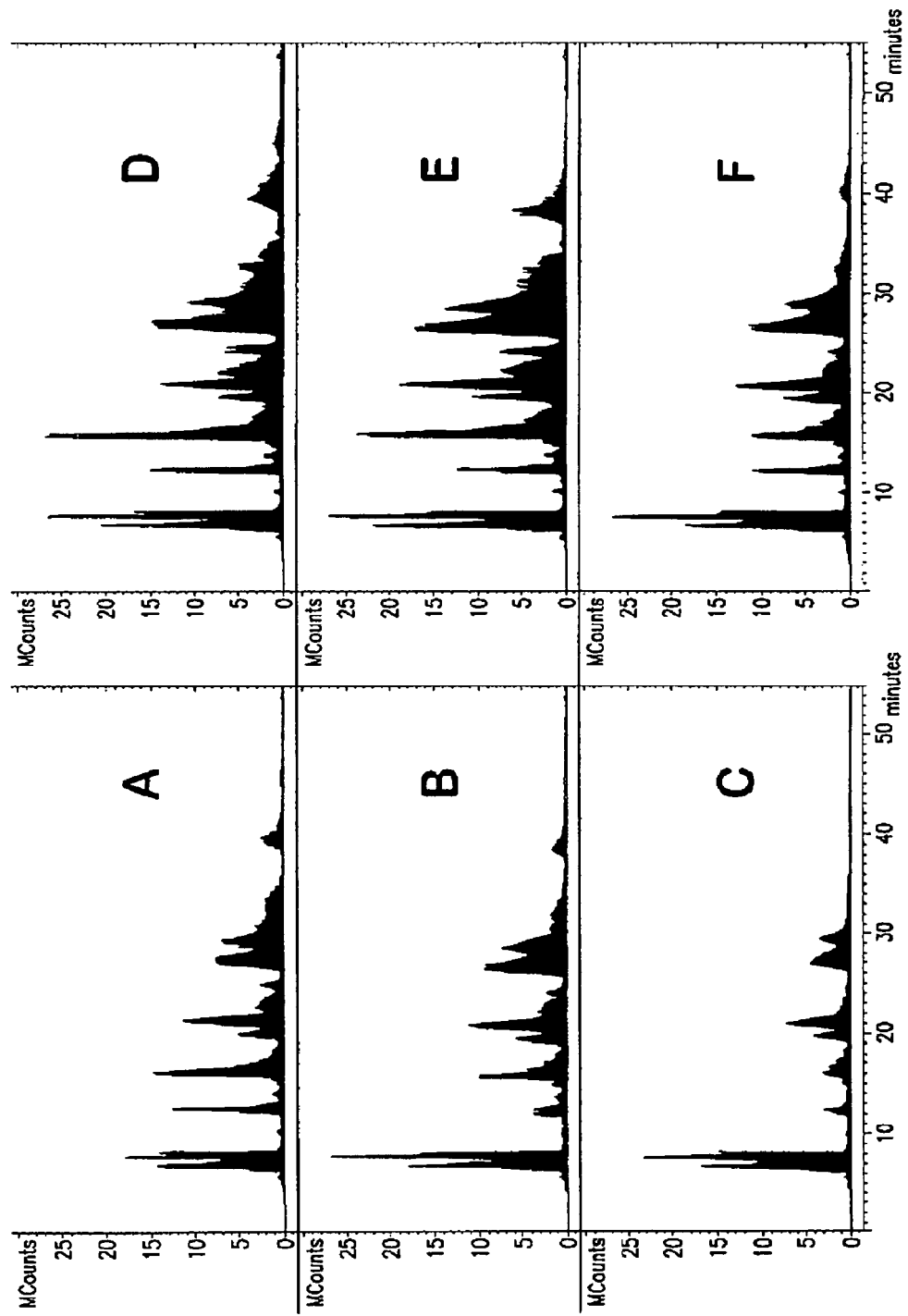
FIG. 7 shows chromatograms of samples subjected to treatment with sorbent relative to untreated samples.
Figure 8:
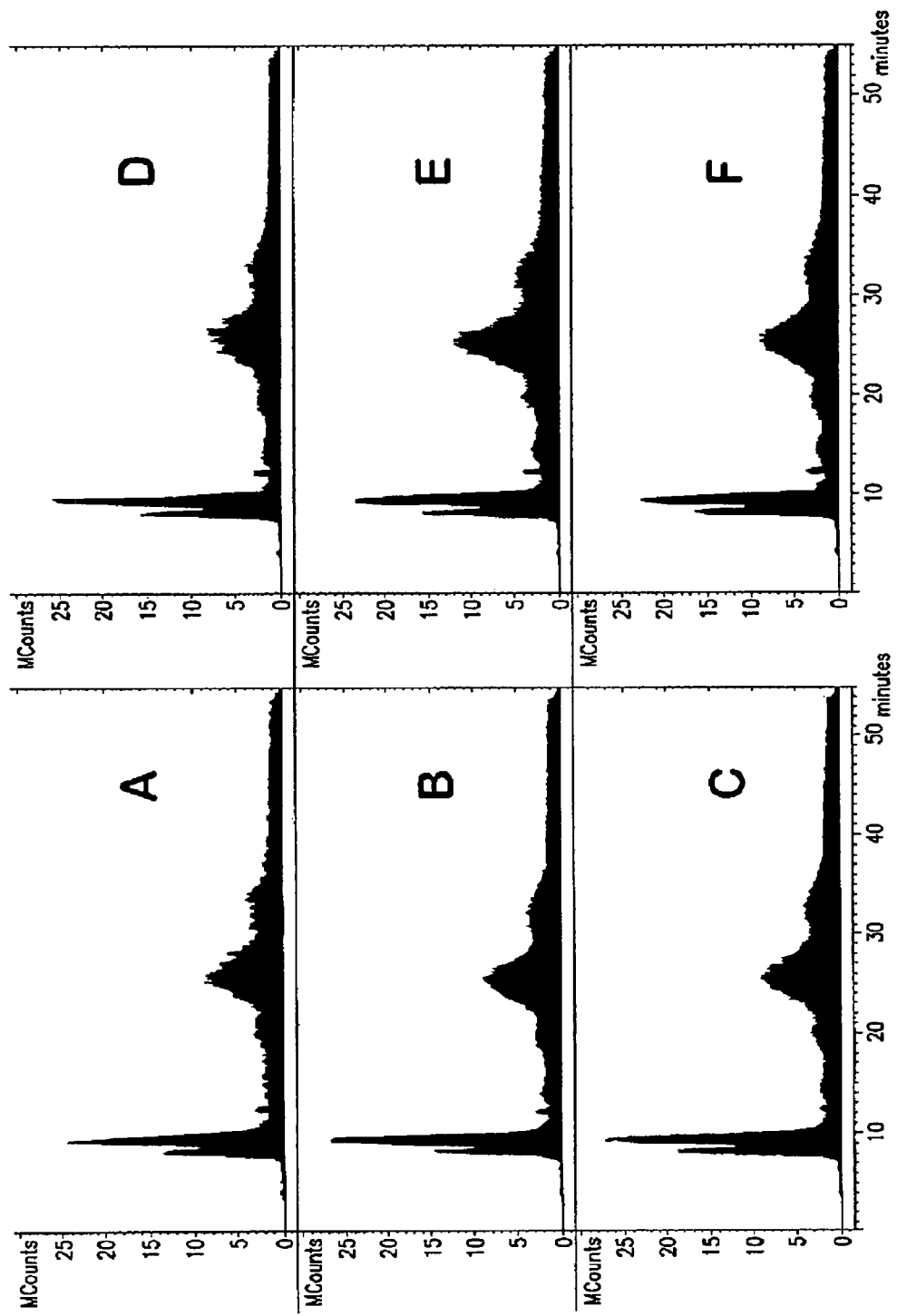
FIG. 8 shows chromatograms of samples subjected to treatment with sorbent relative to untreated samples.
Figure 9:
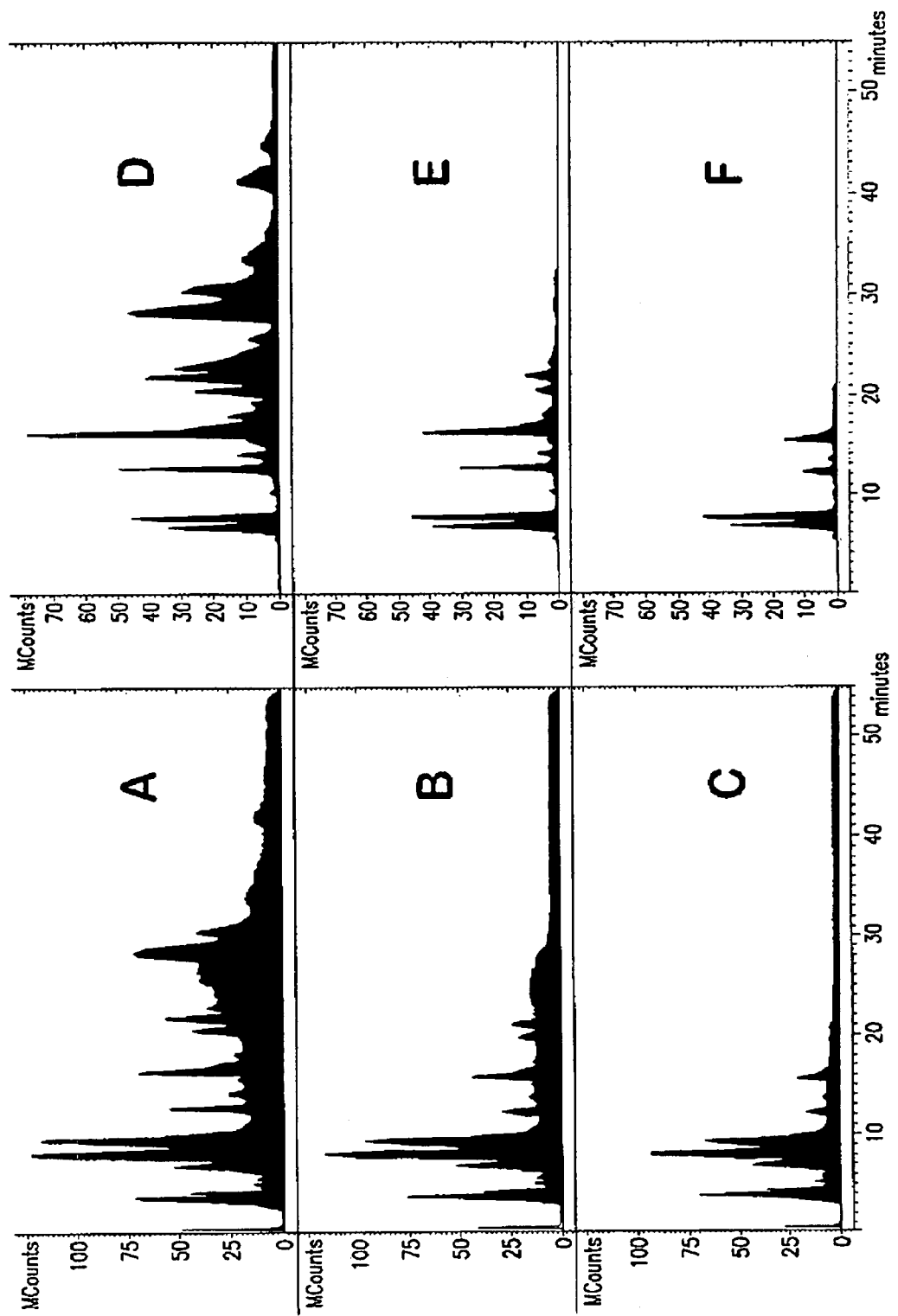
FIG. 9 shows chromatograms of samples subjected to treatment with sorbent relative to untreated samples.
Figure 10:
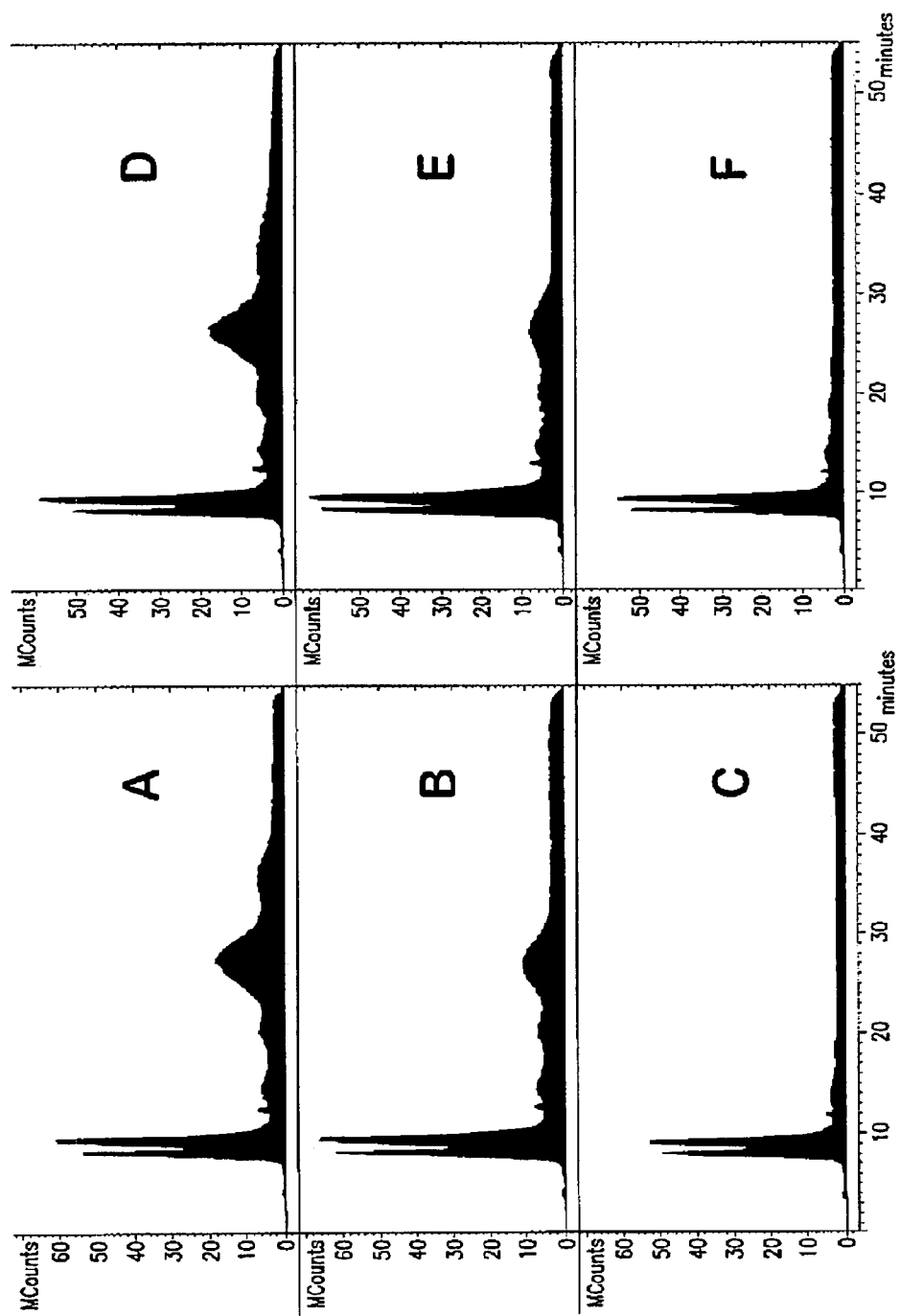
FIG. 10 shows chromatograms of samples subjected to treatment with sorbent relative to untreated samples.

The results are shown in FIGS. 3 through 10, and Tables 3-6 below. FIGS. 3, 5, 7 and 9 demonstrate the reduction of phospholipids by treatment with 10 and 20 mg sorbents ND 06262, ND 06265, ND 06267, and Polaris® C18-Amide, respectively, when treated with 3:1 ACN precipitated supernatants with or without 1% formic acid. FIGS. 4, 6, and 8 show relatively little reduction for Tween 80, however, FIG. 10 demonstrates more significant removal of Tween 80 by Polaris® C18 Amide. These results are presented in tabular form below.

TABLE 3

Results with ND 06262

|  | 10 mg sorbent | | 20 mg sorbent | |
|---|---|---|---|---|
|  | 3:1 ACN | 3:1 ACN + 1% formic acid | 3:1 ACN | 3:1 ACN + 1% formic acid |
| Analyte Detection vs. Captiva ® alone | | | | |
| Zolpidem | 99% | 99% | 150% | 142% |
| Warfarin | 111% | 129% | 95% | 115% |

TABLE 3-continued

Results with ND 06262

|  | 10 mg sorbent | | 20 mg sorbent | |
|---|---|---|---|---|
|  | 3:1 ACN | 3:1 ACN + 1% formic acid | 3:1 ACN | 3:1 ACN + 1% formic acid |
| Quinidine | — | — | — | — |
| Sulindac | 105% | 125% | 116% | 142% |
| Loratadine | 88% | 113% | 122% | 144% |
| Loperamide | 84% | 111% | 114% | 138% |
| Removal vs. Captiva ® alone | | | | |
| Tween 80 | 21% | 15% | 11% | 15% |
| Phosphatidylcholines | 40% | 45% | 72% | 70% |

TABLE 4

Results with ND 06265

|  | 10 mg sorbent | | 20 mg sorbent | |
|---|---|---|---|---|
|  | 3:1 ACN | 3:1 ACN + 1% formic acid | 3:1 ACN | 3:1 ACN + 1% formic acid |
| Analyte Detection vs. Captiva ® alone | | | | |
| Zolpidem | 109% | 108% | 110% | 109% |
| Warfarin | 112% | 106% | 110% | 108% |
| Quinidine | 116% | 108% | 117% | — |
| Sulindac | 137% | 110% | 114% | 107% |
| Loratadine | 117% | 110% | 113% | 109% |
| Loperamide | 126% | 116% | 119% | 121% |
| Removal vs. Captiva ® alone | | | | |
| Tween 80 | 1% | 4% | −2% | −5% |
| Phosphatidylcholines | 14% | 27% | 61% | 57% |

TABLE 5

Results with ND 06267

|  | 10 mg sorbent | | 20 mg sorbent | |
|---|---|---|---|---|
|  | 3:1 ACN | 3:1 ACN + 1% formic acid | 3:1 ACN | 3:1 ACN + 1% formic acid |
| Analyte Detection vs. Captiva ® alone | | | | |
| Zolpidem | 87% | 98% | 92% | 120% |
| Warfarin | 94% | 96% | 84% | 122% |
| Quinidine | 98% | 105% | — | 146% |
| Sulindac | 94% | 92% | 120% | 131% |
| Loratadine | 85% | 86% | 98% | 181% |
| Loperamide | 73% | 85% | 77% | 126% |
| Removal vs. Captiva ® alone | | | | |
| Tween 80 | 3% | −13% | 8% | −2.6% |
| Phosphatidylcholines | 28% | 19% | 54% | 48% |

TABLE 6

Results with Polaris ® C18-Amide

|  | 10 mg sorbent | | 20 mg sorbent | |
| --- | --- | --- | --- | --- |
|  | 3:1 ACN | 3:1 ACN + 1% formic acid | 3:1 ACN | 3:1 ACN + 1% formic acid |
| Analyte Detection vs. Captiva ® alone | | | | |
| Zolpidem | 97% | 106% | 94% | 99% |
| Warfarin | 103% | 112% | 96% | 97% |
| Quinidine | 118% | 89% | 94% | 97% |
| Sulindac | 104% | 106% | 105% | 97% |
| Loratadine | 106% | 106% | 95% | 99% |
| Loperamide | 118% | 118% | 102% | 107% |
| Removal vs. Captiva ® alone | | | | |
| Tween 80 | 25% | 27% | 42% | 41% |
| Phosphatidylcholines | 53% | 70% | 68% | 81% |

More surfactant and phospholipids were removed when using the larger amount of sorbent, indicating that there is a positive correlation between the amount of sorbent used and the amount of Tween 80 and phosphatidylcholines removed. However, sensitivity to analytes was not sacrificed in this bed mass range. Generally, removal of phospholipids and Tween 80 resulted in enhancement of analyte detection, which is consistent with removal of matrix interfering agents which results in reduction in ion suppression.

EXAMPLE 3

Surfactant Removal from Protein Precipitated Samples

Porcine plasma samples were spiked with analytes (Zolpidem, Warfarin, Sulindac, Loratadine, Vardenafil) to 1 ppm, together with surfactants (Triton X 100, Tween 80, and Sodium dodecyl sulfate (SDS)) to a concentration of 1 mg/mL. Samples (200 µL) were precipitated using one of four treatments:

400 µL 3% formic acid in acetonitrile (2:1)
600 µL 3% formic acid in acetonitrile (3:1)
400 µL 3% formic acid in methanol (2:1)
600 µL 3% formic acid in methanol (3:1)

Samples were centrifuged at 14,000 rpm for 12 min in a mini-centrifuge. The supernatant was extracted as described in Example 2 using 20 mg Polaris® C 18-A sorbent assembled on top of a Captiva® 0.45 µm membrane. Ten µl aliquots were analyzed by HPLC as described in Example 2 and Table 7 as shown below.

TABLE 7

HPLC Elution Program

| Time | % B | Flow rate (µl/min) |
| --- | --- | --- |
| 0.00 | 5 | 350 |
| 1.00 | 5 | 350 |
| 8:00 | 90 | 350 |
| 53:00 | 90 | 350 |
| 53:01 | 5 | 350 |
| 55:00 | 5 | 350 |

Analytes were detected using the molecular ions shown in Table 8.

TABLE 8

Analyte molecular ions

| Analytes | MS transition | Collision Energy (V) |
| --- | --- | --- |
| Zolpidem | 308.1 → 235.0 | −28 |
| Warfarin | 309.0 → 163.0 | −11 |
| Sulindac | 357.1 → 233.0 | −41 |
| Loratadine | 383.0 → 337.0 | −22.5 |
| Vardenafil | 489.2 → 151.0 | −35.5 |
| Triton X-100 | 625.4 → 625.4 | −16.5 |
| Tween 80 | 309.0 → 309.0 | −5 |
| Phosphatidylcholines | 184.0 → 184.0 | −5 |

Figure 11:
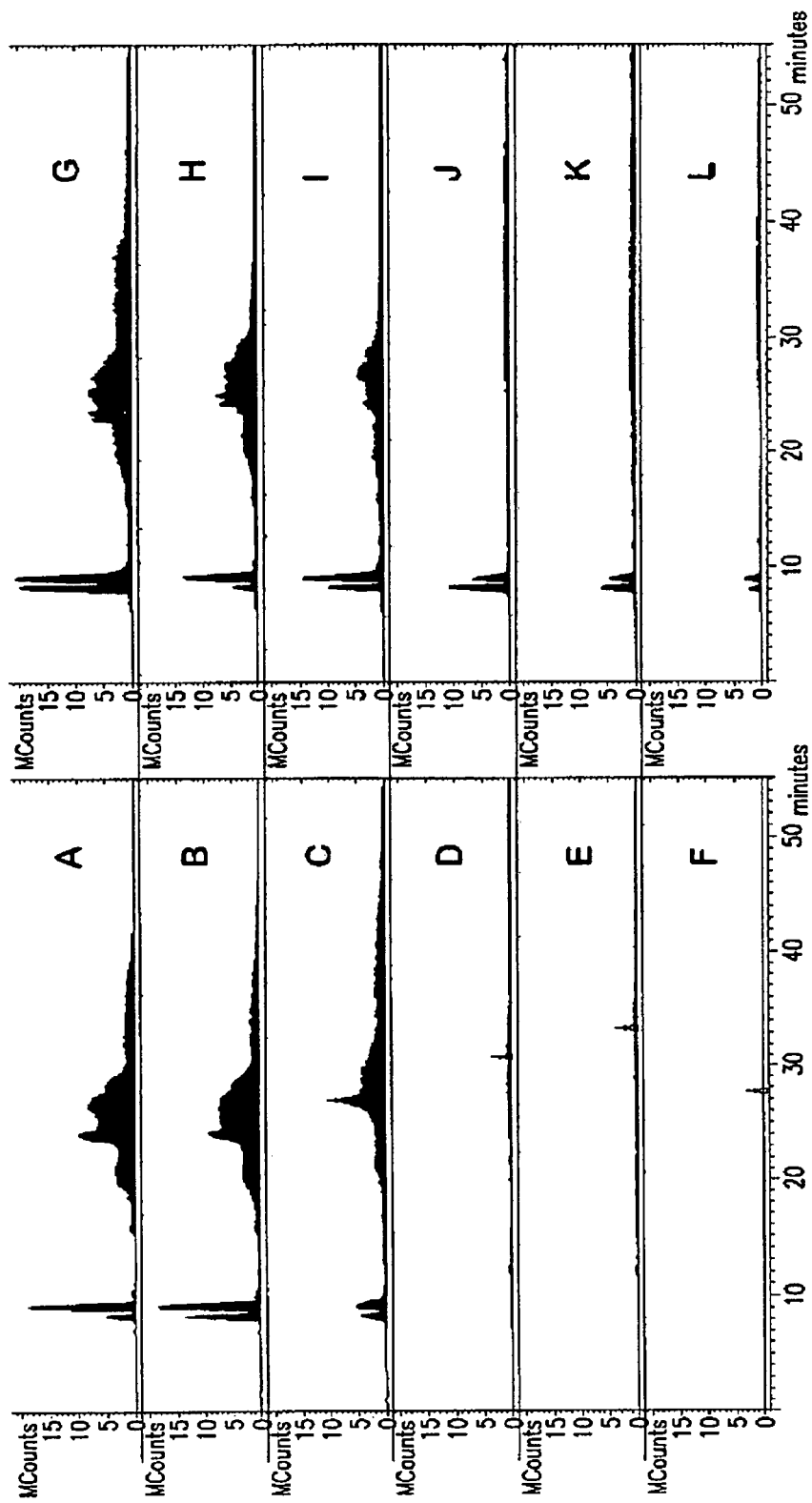
FIG. 11 shows chromatograms of samples subjected to treatment with sorbent relative to untreated samples.

The results are summarized in Table 9. Chromatographic results are shown in FIGS. 11-14. FIG. 11 illustrates three chromatograms each of plasma protein precipitated using 2:1 MeOH (A-F) or 2:1 ACN (G-L) with 3% formic acid in both solutions; i.e., each chromatogram was performed in triplicate. FIG. 11A-C illustrate chromatograms obtained for protein precipitated plasma untreated with sorbent, while FIG. 11D-F illustrate the effect of treatment with 20 mg Polaris® C 18-A (the reduction in Tween 80 in the treated sample). Similarly, FIG. 11G-I illustrate chromatograms obtained for protein precipitated plasma untreated with sorbent, while FIG. 11J-L illustrate the effect of treatment with 20 mg Polaris® C18-A (the reduction in Tween 80 in the treated sample).

Figure 12:
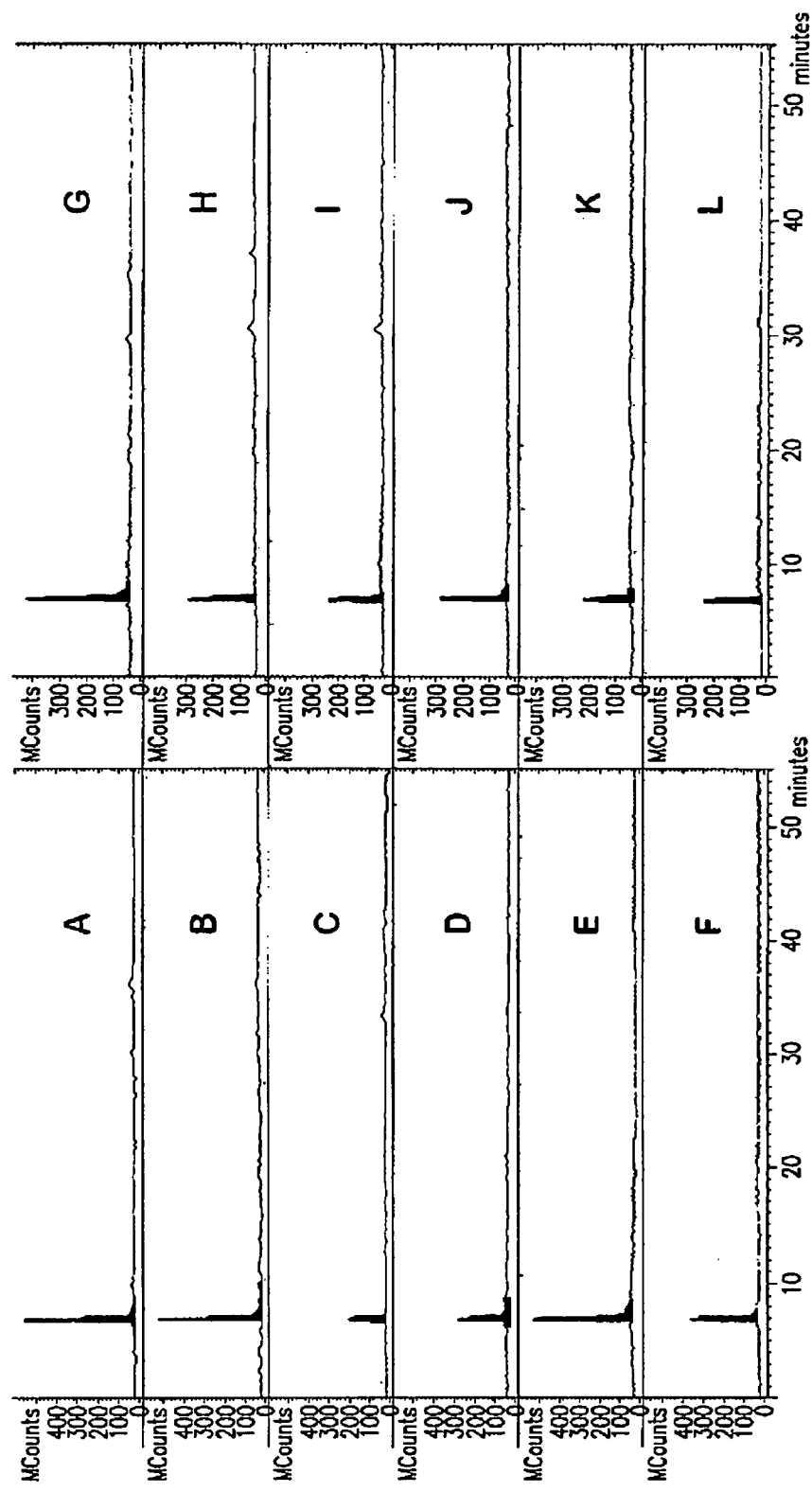
FIG. 12 shows chromatograms of samples subjected to treatment with sorbent relative to untreated samples.

FIG. 12 illustrates three chromatograms each of plasma protein precipitated using 2:1 MeOH (A-F) or 2:1 ACN (G-L) with 3% formic acid in both solutions; i.e., each chromatogram was performed in triplicate. FIG. 12A-C illustrate chromatograms obtained for protein precipitated plasma untreated with sorbent, while FIG. 12D-F illustrate the effect of treatment with 20 mg Polaris® C 18-A (the reduction in Triton X-100 in the treated sample). Similarly, FIG. 12G-I illustrate chromatograms obtained for protein precipitated plasma untreated with sorbent, while FIG. 12J-L illustrate the effect of treatment with 20 mg Polaris® C18-A (the reduction in Triton X-100 in the treated sample).

Figure 13:
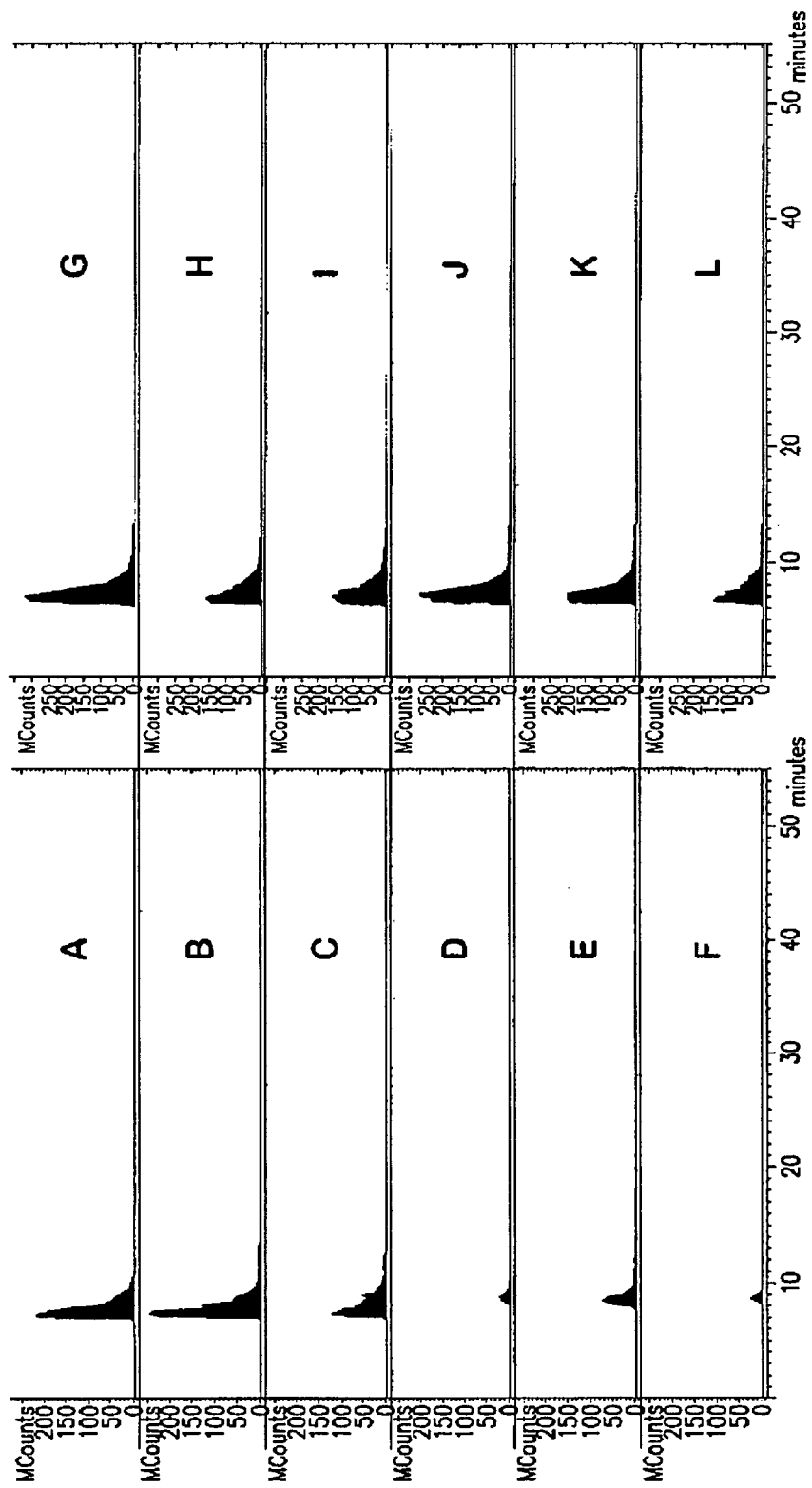
FIG. 13 shows chromatograms of samples subjected to treatment with sorbent relative to untreated samples.

FIG. 13 illustrates three chromatograms each of plasma protein precipitated using 2:1 MeOH (A-F) or 2:1 ACN (G-L) with 3% formic acid in both solutions; i.e., each chromatogram was performed in triplicate. FIG. 13A-C illustrate chromatograms obtained for protein precipitated plasma untreated with sorbent, while FIG. 13D-F illustrate the effect of treatment with 20 mg Polaris® C 18-A (the reduction in SDS in the treated sample). Similarly, FIG. 13G-I illustrate chromatograms obtained for protein precipitated plasma untreated with sorbent, while FIG. 13J-L illustrate the effect of treatment with 20 mg Polaris® C18-A (the reduction in SDS in the treated sample).

Figure 14:
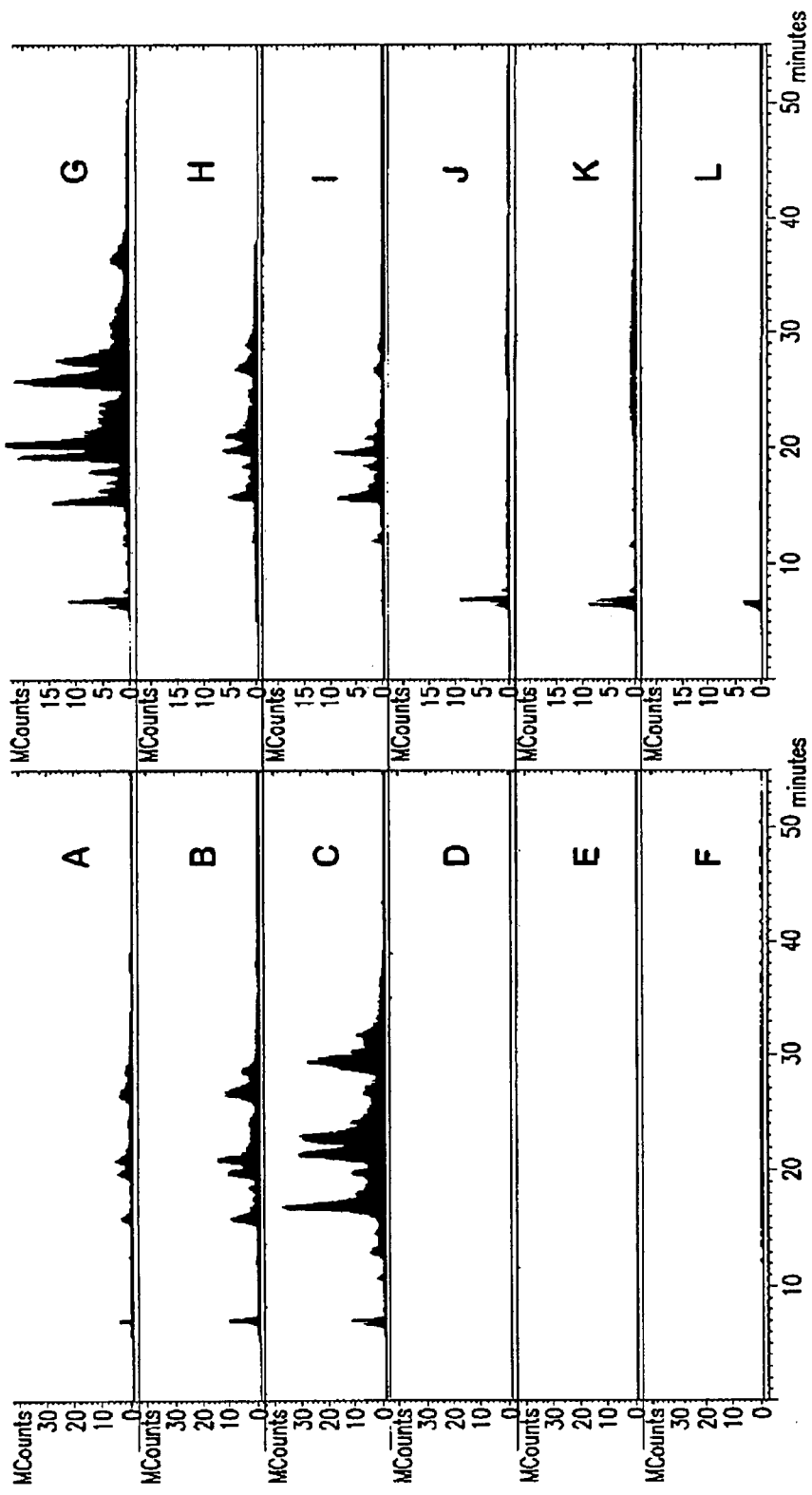
FIG. 14 shows chromatograms of samples subjected to treatment with sorbent relative to untreated samples.

FIG. 14 illustrates three chromatograms each of plasma protein precipitated using 2:1 MeOH (A-F) or 2:1 ACN (G-L) with 3% formic acid in both solutions; i.e., each chromatogram was performed in triplicate. FIG. 14A-C illustrate chromatograms obtained for protein precipitated plasma untreated with sorbent, while FIG. 14D-F illustrate the effect of treatment with 20 mg Polaris® C18-A (the reduction in phosphatidylcholines in the treated sample). Similarly, FIG. 14G-I illustrate chromatograms obtained for protein precipitated plasma untreated with sorbent, while FIG. 14J-L illustrate the effect of treatment with 20 mg Polaris® C18-A (the reduction in phosphatidylcholines in the treated sample).

TABLE 9

| Surfactant removal with sorbent relative to filtration alone | 2:1 methanol + 3% formic acid | 3:1 methanol + 3% formic acid | 2:1 ACN + 3% formic acid | 3:1 ACN + 3% formic acid |
|---|---|---|---|---|
| Tween 80 | 90% | 91% | 76% | 70% |
| Triton X 100 | −10% | −0.4% | 32% | 20% |
| SDS | 85% | 40% | 6% | 6% |
| Phosphatidylcholines | 99% | 99% | 84% | 91% |

As shown in FIGS. 11-14, and Table 9, surfactants and lipids could be substantially removed from the protein precipitated samples using one or more of the protocols tested. For example, use of MeOH at either 2:1 or 3:1 dilution of plasma with 3% formic acid showed substantially complete removal of phosphatidylcholines and Tween 80 from samples. Use of ACN at either 2:1 or 3:1 dilution of plasma with 3% formic acid showed substantially complete removal of phosphatidylcholines and significant removal of Tween 80 from samples. Removal of SDS was more dependent on strength of the eluting solvent, as 85% of SDS could be removed with 2:1 MeOH, while only 40% could be removed with 3:1 MeOH. Using Polaris C18-A as the sorbent, ACN was not effective to remove SDS from samples. Removal of Triton X-100 was less effective under these conditions, with significant removal using ACN but not with MeOH.

EXAMPLE 4

Effect of Acid Concentration on Lipid Removal

Ten mL porcine plasma samples were spiked with analytes (Zolpidem, Warfarin, Sulindac, Loratadine, Loperamide, Vardenafil) to 1 ppm, together with 5 mg/mL Tween 80. Samples were precipitated by using 30 mL of one of three treatments:

Acetonitrile

1% formic acid in acetonitrile

2% formic acid in acetonitrile

Samples were centrifuged at 8,000 rpm for 30 min at 15 C using a Sorvall 50 ml rotor. Samples of supernatant (800 μL) were filtered as in Example 2 using 20 mg of ND 06262 or Polaris® C18-Amide sorbent assembled on top of a Captiva® 0.45 μm membrane into a collection plate under full vacuum.

Figure 15:
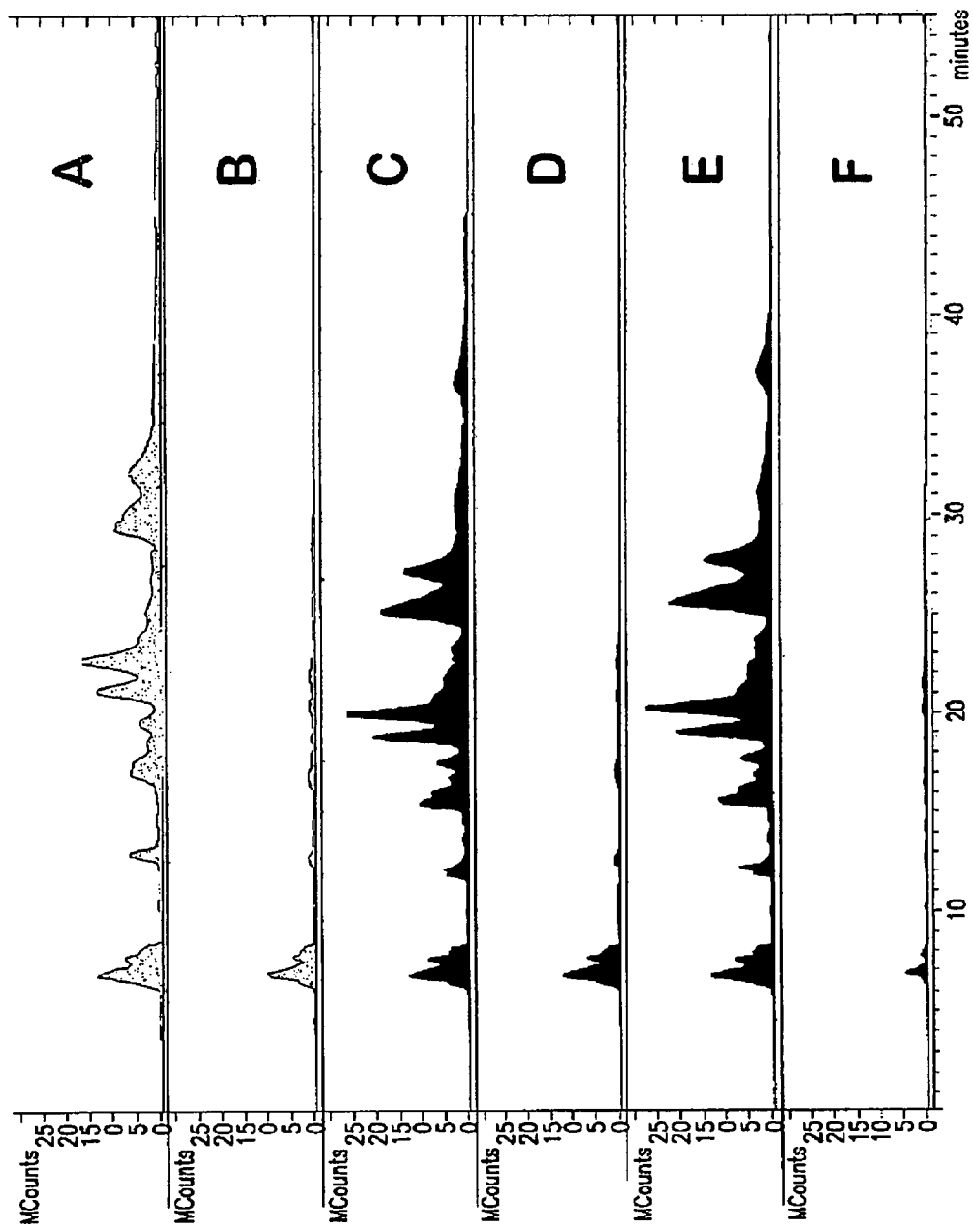
FIG. 15 shows chromatograms of samples subjected to treatment with sorbent relative to untreated samples.
Figure 16:
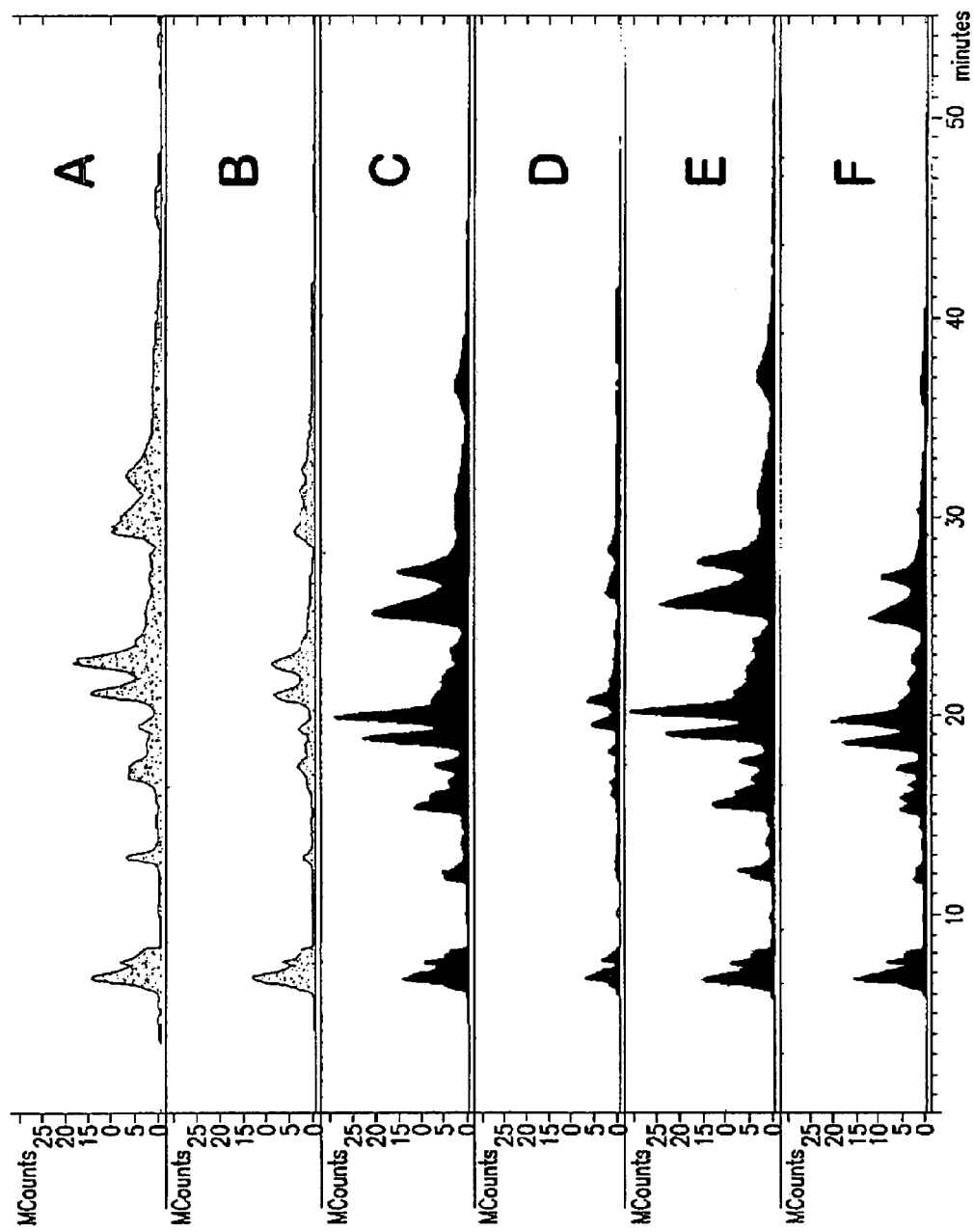
FIG. 16 shows chromatograms of samples subjected to treatment with sorbent relative to untreated samples.

Ten μl aliquots were analyzed by HPLC as described, and analytes were detected by their mass spectrometric transitions, as described in Example 3. The results are summarized in Tables 10 and 11. Chromatographic results are shown in FIGS. 15 and 16. FIG. 15 illustrates chromatograms generated using untreated samples (A, C, E) and samples treated with 20 mg Polaris® C18-Amide sorbent (B, D, F). Treatment of samples with 3:1 ACN without pH modifier is shown in FIGS. 15A and B, illustrating the reduction in phosphatidylcholines in the sample. Treatment of samples with 3:1 ACN with 1% formic acid is shown in FIGS. 15C and D, illustrating the reduction in phosphatidylcholines in the sample. Treatment of samples with 3:1 ACN with 2% formic acid is shown in FIGS. 15E and F, illustrating the reduction in phosphatidylcholines in the sample.

TABLE 10

Analyte detection using Polaris C18 Amide sorbent to remove matrix interfering agents

| | 3:1 ACN | 3:1 ACN + 1% formic acid | 3:1 ACN + 2% formic acid |
|---|---|---|---|
| Recovery vs. Captiva ® filter alone | | | |
| Zolpidem | 100.3% | 106.1% | 189.3% |
| Warfarin | 118.0% | 112.1% | 107.9% |
| Sulindac | 117.5% | 110.1% | 114.0% |
| Loratadine | 114.9% | 99.9% | 99.4% |
| Loperamide | 116.6% | 107.6% | 117.1% |
| Vardenafil | 116.0% | 93.3% | 120.0% |
| Removal vs. Captiva ® filter alone | | | |
| Tween 80 | 54% | 48% | 37% |
| Phosphatidylcholine | 76% | 86% | 95% |

These results demonstrate a marked relationship between phosphatidylcholine removal and acid concentration with Polaris® C18 Amide, such that 2% formic acid resulted in the especially enhanced detection of Zolpidem. At this highest acid concentration tested and in ACN, nearly complete removal of phosphatidylcholine was achieved, even for lyso-phosphatidylcholine, which is notably difficult to remove, and possibly resulting in greater enhancement in analyte detection. Tween 80 removal was also significant. Removal of these matrix interfering agents results in analyte dependent enhancement of signal, due to the variable effects of these ion suppression agents on individual analyte signals.

TABLE 11

Analyte detection using ND06262 sorbent to remove matrix interfering agents

| | 3:1 ACN | 3:1 ACN + 1% formic acid | 3:1 ACN + 2% formic acid |
|---|---|---|---|
| Recovery vs. Captiva ® filter alone | | | |
| Zolpidem | 88.8% | 108.8% | 101.2% |
| Warfarin | 113.1% | 97.5% | 103.8% |
| Sulindac | 103.7% | 93.0% | 97.8% |
| Loratadine | 100.0% | 87.6% | 90.5% |
| Loperamide | 96.5% | 90.7% | 98.2% |
| Vardenafil | 88.8% | 79.0% | 84.9% |
| Removal vs. Captiva ® filter alone | | | |
| Tween 80 | 6% | −8% | −18% |
| Phosphatidylcholine | 26% | 58% | 53% |

ND06262 also demonstrates significant removal of phosphatidylcholine, however, under these solvent conditions, this sorbent demonstrates little efficacy in removing Tween 80 from the plasma samples. FIG. 16 illustrates chromatograms generated using untreated samples (A, C, E) and samples treated with 20 mg ND06262 sorbent (B, D, F). Treatment of samples with 3:1 ACN without pH modifier is shown in FIGS. 16A and B, illustrating the reduction in phosphatidylcholines in the sample. Treatment of samples with 3:1 ACN with 1% formic acid is shown in FIGS. 16C and D, illustrating the reduction in phosphatidylcholines in the sample. Treatment of samples with 3:1 ACN with 2% formic acid is shown in FIGS. 16E and F, illustrating the reduction in phosphatidylcholines in the sample.

EXAMPLE 5

Methanol Testing

Porcine plasma samples (100 μL) were spiked with analytes (Zolpidem, Warfarin, Sulindac, Loratadine, Loperamide, Vardenafil) to 1 ppm, together with Tween 80 at 5 mg/mL. Samples were precipitated by diluting plasma samples with 200 μL of methanol/3.0% formic acid. Samples were centrifuged at 14,000 rpm for 15 min at room temperature in a microcentrifuge. Samples of supernatant were filtered as in Example 2 using 20 mg of Polaris® C18-A sorbent or simply transferred directly to a collection plate.

Figure 17:
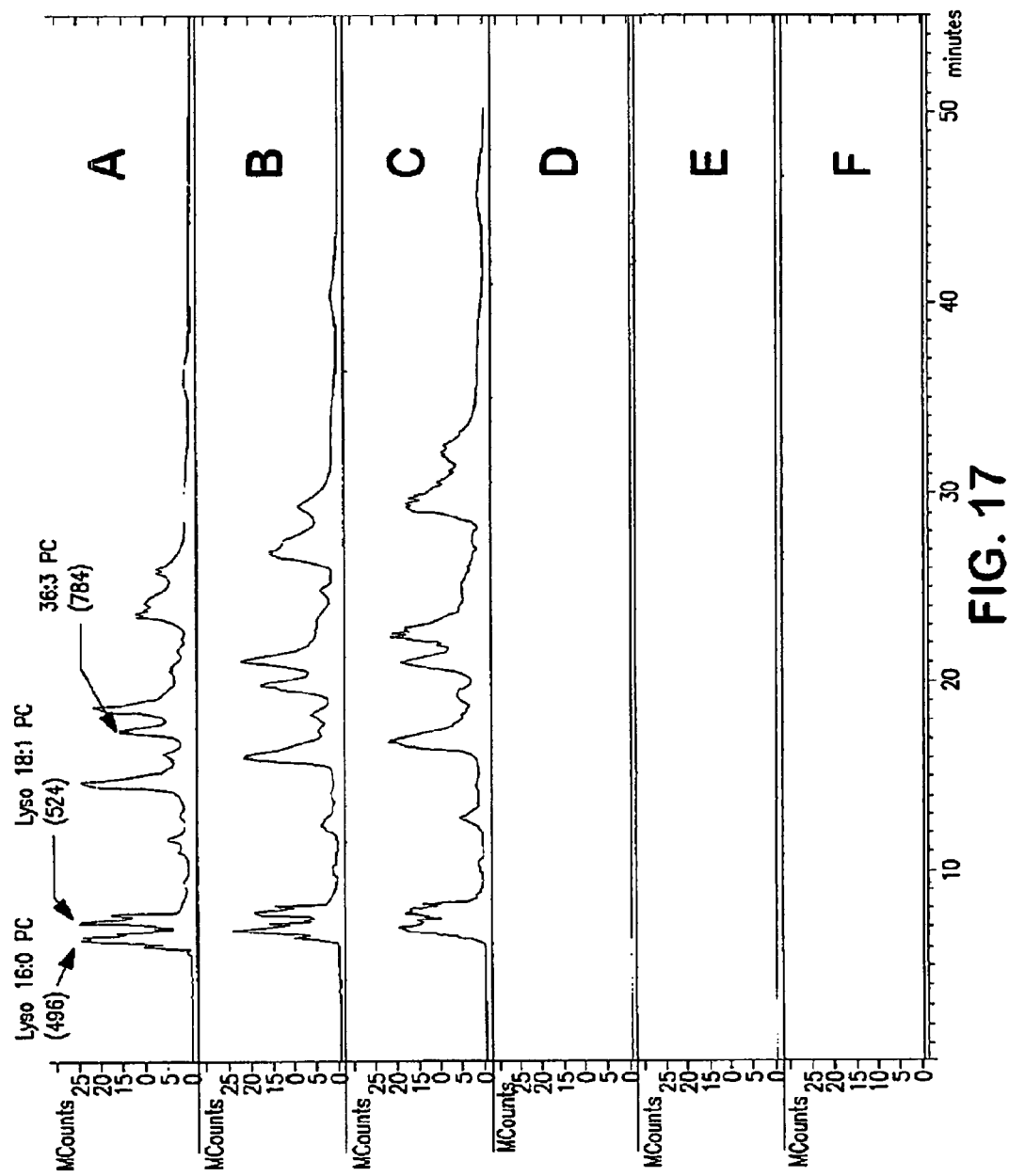
FIG. 17 shows chromatograms of samples subjected to treatment with sorbent relative to untreated samples.

Ten μl aliquots were analyzed by HPLC as described in Example 3. The results are summarized in Table 12. Chromatographic results are shown in FIG. 17, pointing out particular species of phosphatidylcholines observed. FIG. 17A-C illustrate three chromatograms of protein precipitated plasma untreated with sorbent (the experiment was performed in triplicate). FIG. 17D-F illustrate three chromatograms of protein precipitated plasma treated with 20 mg of Polaris® C18-A sorbent assembled on top of a Captiva® 0.45 μm membrane (the experiment was performed in triplicate).

TABLE 12

Analyte detection and removal of matrix interfering agents

| Recovery vs. precip. only | |
|---|---|
| Zolpidem | 109.6% |
| Warfarin | 100.5% |
| Sulindac | 136.7% |
| Loratadine | 103.4% |
| Loperamide | 106.7% |
| Vardenafil | 106.5% |
| Removal vs. precip. only | |
| Tween 80 | 81.8% |
| Phosphatidylcholine | 97.3% |

These results demonstrate the nearly complete removal of both Tween 80 and phospholipids present in the samples and complete recovery of analytes when using the Polaris® C18-A sorbent under these solvent conditions. This combination of sorbent and protein precipitation conditions results in the surprisingly complete removal of matrix interfering agents with no loss of analytes in a simple precipitation/extraction procedure.

EXAMPLE 6

Sorbent Selectivity Testing

Porcine plasma was protein precipitated using a 3:1 ACN dilution, and proteins were removed by centrifugation as described in Example 4. Samples of the plasma were spiked with the following analytes: Amitriptyline, Sumatriptan, Lamotrigine, Loratadine, Clozapine, and Quetiapine to 10 ppm, together with Tween 80 at 5 mg/mL. Ten μl aliquots of supernatant, analytes and Tween 80 were analyzed by HPLC using a various sorbents (40 mm×4.0 mm) with a gradient of A: 0.1% formic acid and B: acetonitrile according to Table 13 using a Varian 1200L LC/MS-MS system. The following sorbents were tested: Polaris® C18, Polaris® C18-A, and Focus® (Varian, Inc., Palo Alto, Calif.) and ND 06047 (instrAction GmbH, Ludwigshafen, DE).

TABLE 13

HPLC Elution Program

| Time | % B | Flow rate (μl/min) |
|---|---|---|
| 0.00 | 10 | 500 |
| 0.66 | 10 | 500 |
| 1.66 | 90 | 500 |
| 2.33 | 90 | 500 |
| 2.34 | 10 | 500 |
| 3.00 | 10 | 500 |

The quantitation of the specific analytes and matrix interfering agents were determined using the mass spectrometric transitions shown in Table 12.

TABLE 14

Analyte molecular ions

| Figure designation | Analytes | MS transition | Collision Energy |
|---|---|---|---|
| A | Phosphatidylcholines | 184.0 → 184.0 | −5 |
| B | Tween 80 | 309.0 → 309.0 | −5 |
| C | Lamotrigine | 256.0 → 256.0 | −4 |
| D | Amitriptyline | 278.1 → 233.0 | −15 |
| E | Sumatriptan | 296.0 → 58.0 | −13 |
| F | Clozapine | 327.0 → 270.0 | −21 |
| G | Loratadine | 383.0 → 337.0 | −22.5 |
| H | Quetiapine | 384.0 → 309.2 | −5 |

Figure 18:
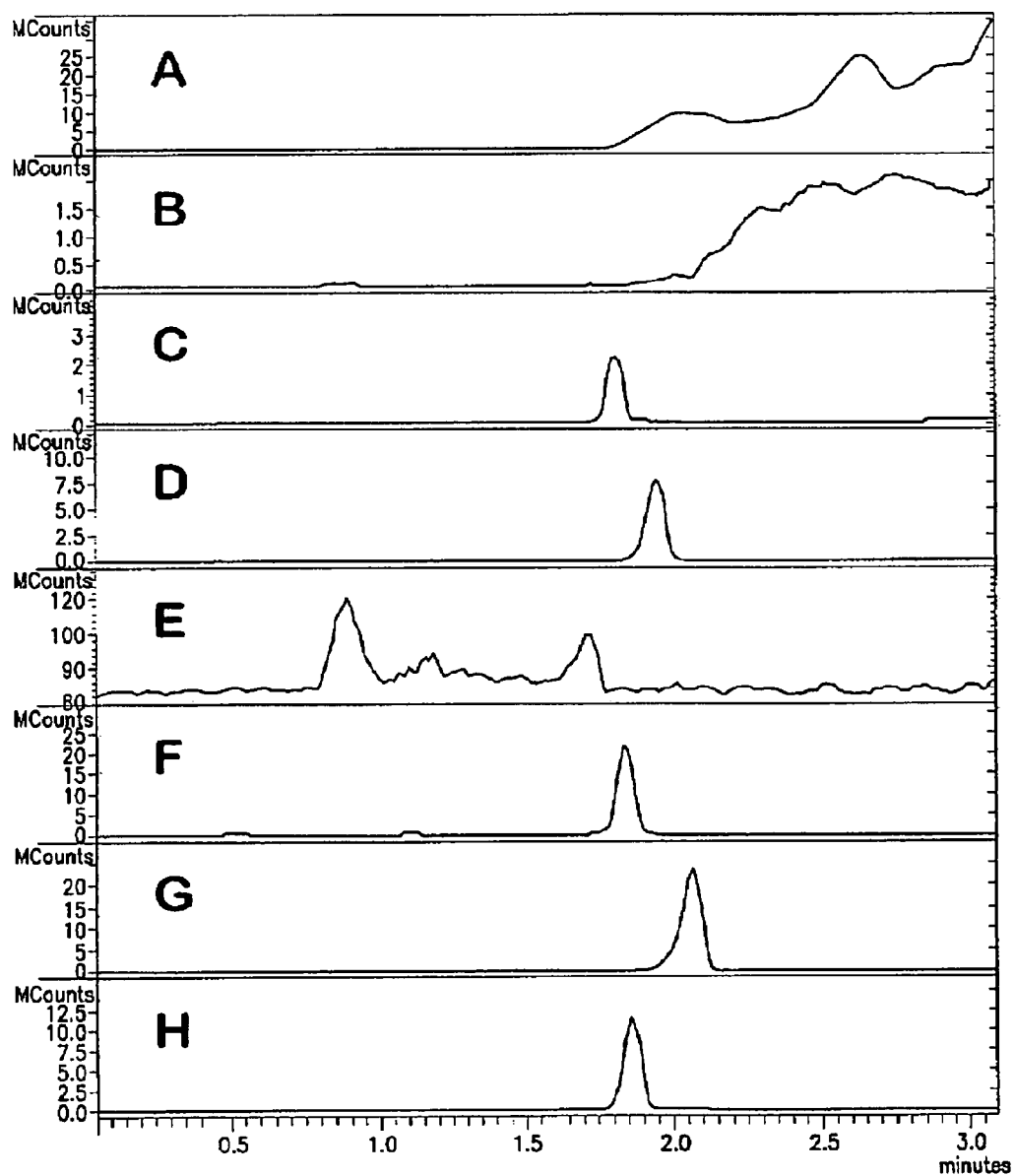
FIG. 18 shows chromatograms of analytes and matrix interfering agents on a reversed phase sorbent.

The results are shown in FIGS. 18-21, with A-H indicating analyte tracings as shown in Table 14. FIG. 18 shows the elution of analytes and matrix interfering agents on a pure reversed phase sorbent, C-18 modified silica (Polaris® C18), and demonstrates that there is some overlap in retention times for some of the later eluting analytes with the matrix interfering agents phosphatidylcholines and Tween 80 due to the strong retention of nonpolar analytes on this sorbent. The calculated selectivity between Loratadine (the least polar analyte, log P=3.65) and the leading edge of phosphatidylcholines or Tween 80 peaks is about 1.

Figure 19:
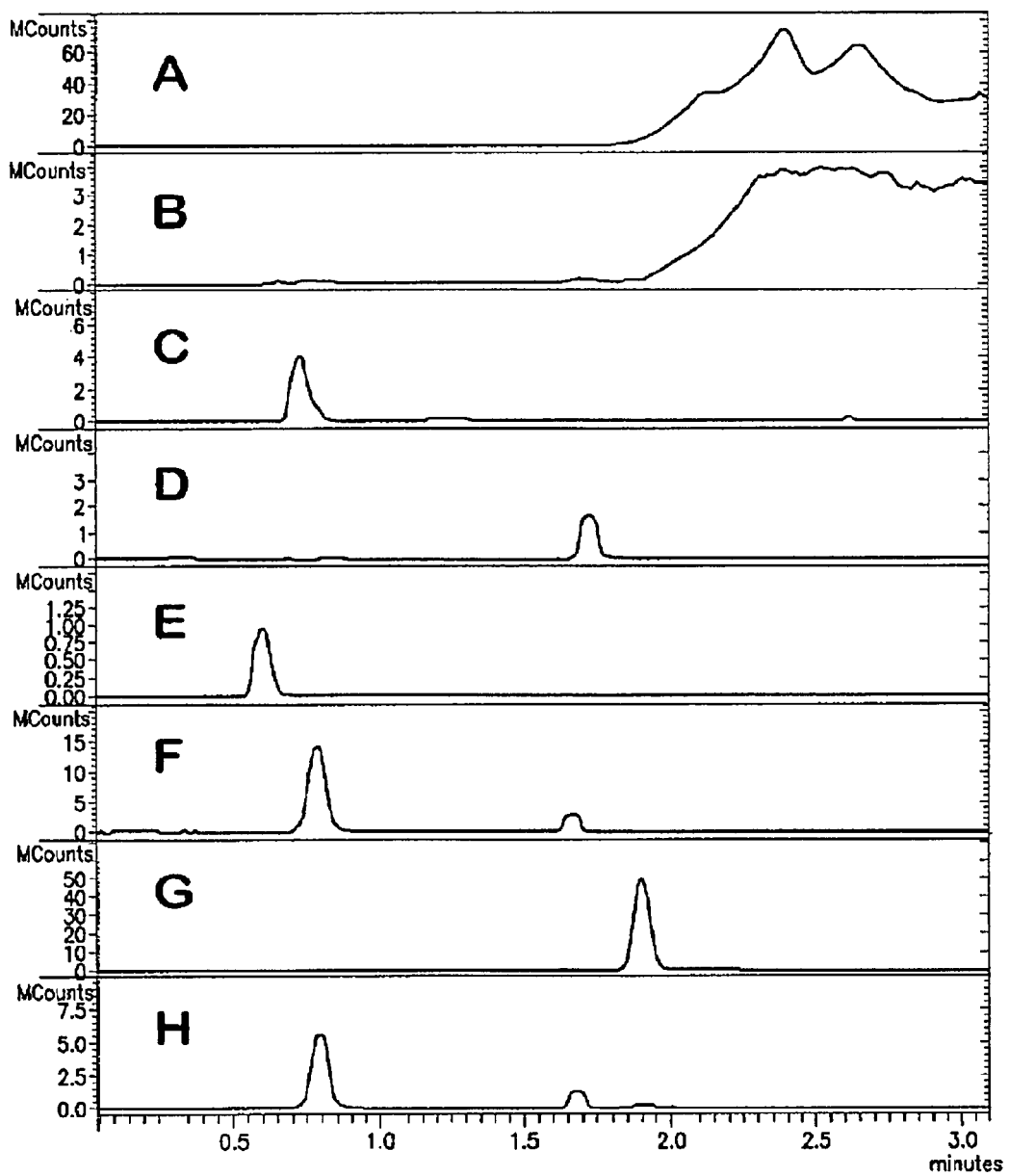
FIG. 19 shows chromatograms of analytes and matrix interfering agents on a polar modified reversed phase sorbent.

FIG. 19 shows the elution of analytes and matrix interfering agents on a polar modified reversed phase sorbent, Polaris® C18-A, and demonstrates that there is very little overlap in retention times for the later eluting analytes with the matrix interfering agents phosphatidylcholines and Tween 80 due to the less strong retention of nonpolar analytes on this sorbent in acidic solvent elution conditions (basic analytes are less retained by the polar modified sorbent.).

Figure 20:
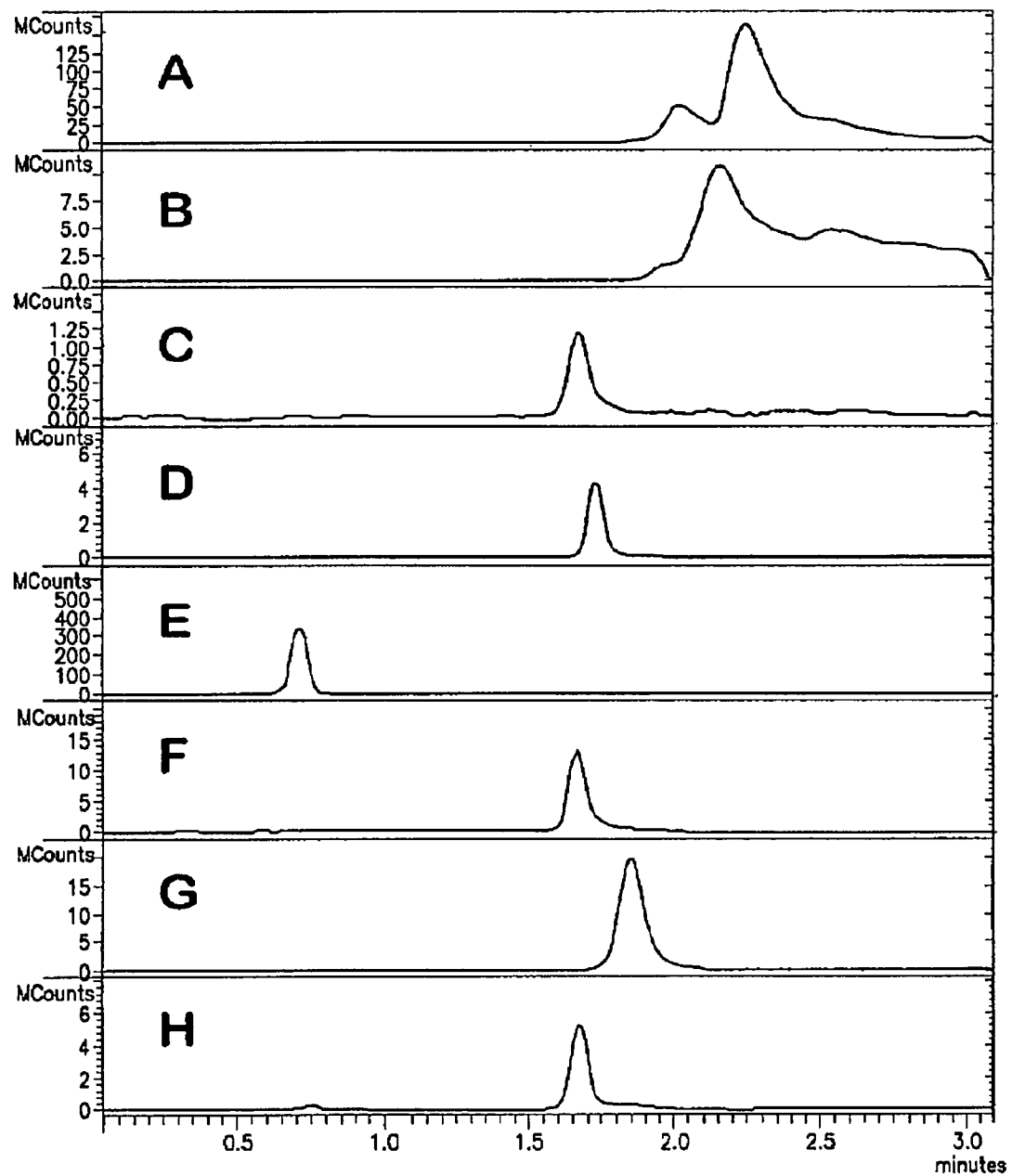
FIG. 20 shows chromatograms of analytes and matrix interfering agents on a polar modified reversed phase sorbent.

FIG. 20 shows the elution of analytes and matrix interfering agents on a polar modified reversed phase sorbent, Focus (a reversed phase amide modified aromatic polymer), and demonstrates that there is very little overlap in retention times for some of the later eluting analytes with the matrix interfering agents phosphatidylcholines and Tween 80 due to the less strong retention of nonpolar analytes on this sorbent.

Figure 21:
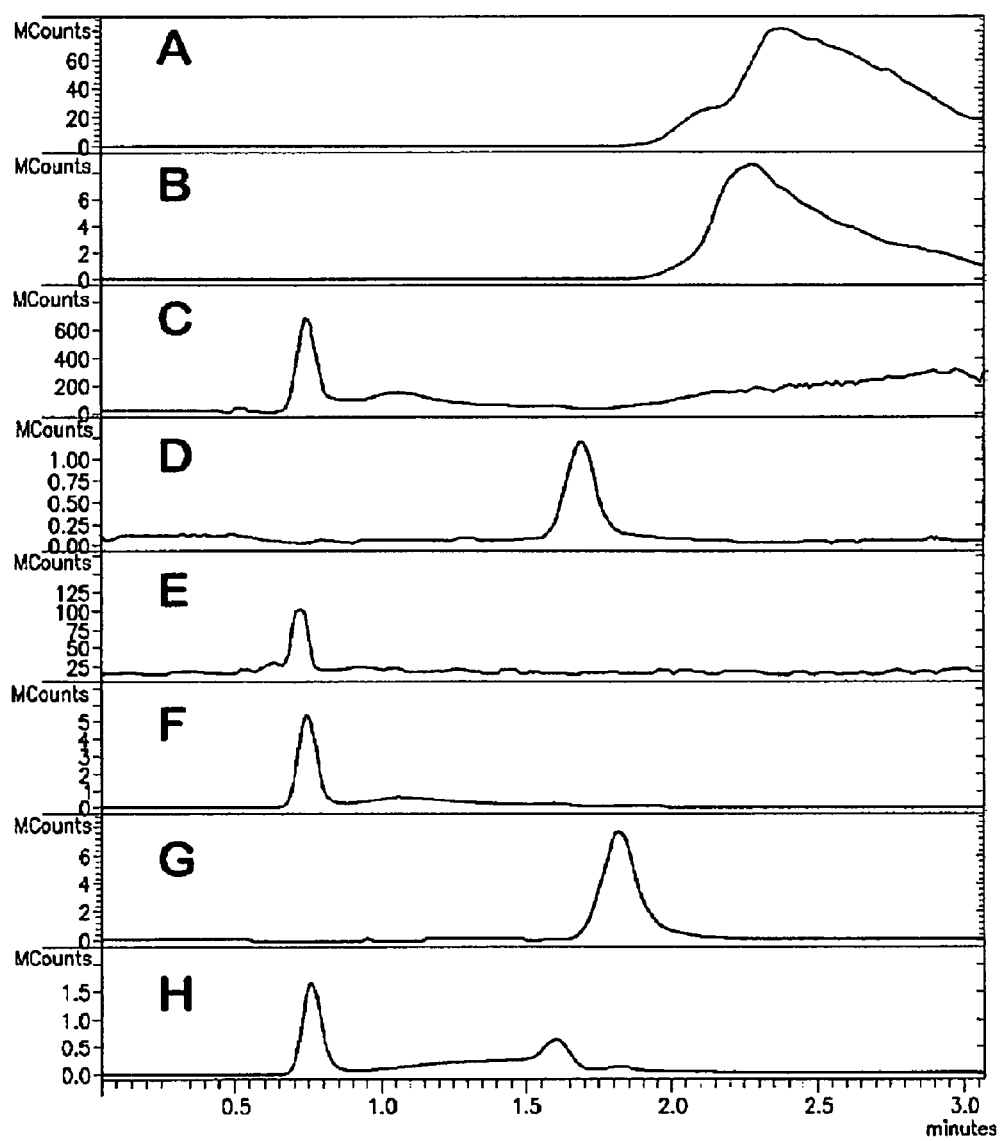
FIG. 21 shows chromatograms of analytes and matrix interfering agents on a polar modified reversed phase sorbent.

Finally, FIG. 21 shows the elution of analytes and matrix interfering agents on instrAction ND06047 (a polymer network formed on silica beads), and demonstrates that there is very little overlap in retention times for some of the later eluting analytes with the matrix interfering agents phosphatidylcholines and Tween 80 due to the less strong retention of nonpolar analytes on this sorbent. There is very little resolution between certain of the analytes as well under these elution conditions, but resolution between analytes is not intended for these sorbents.

These chromatograms demonstrate the selectivity of the sorbents tested over a broad range of analyte and matrix interfering agent retention times. The calculated selectivity between Loratadine (the least polar analyte, log P=3.65) and the leading edge of phosphatidylcholines or Tween 80 peaks is greater than 1 for all polar modified reversed phase sorbents, allowing the selective separation of even strongly nonpolar analytes from the matrix interfering agents phosphatidylcholines and Tween 80.

EXAMPLE 7

Particulate Size and Method of Protein Precipitation

Porcine plasma samples (0.2 ml) were protein precipitated using one of the following four treatments to yield either 66% (v/v) or 75% (v/v) organic solvent solutions:
addition of 0.4 ml MeOH with 3% formic acid
addition of 0.6 ml MeOH with 3% formic acid
addition of 0.4 ml ACN with 1% formic acid
addition of 0.6 ml ACN with 1% formic acid.

The protein precipitated samples were passed through a Captiva® plate using 0.45 μm or 0.2 μm pore size filters or a Captiva® plate containing sorbent (20 mg 10 μm C18-A) using 0.45 μm or 0.2 μm pore size filters. Transmittance (% T, 1 cm path, relative to MeOH blank) was measured at 524 nm to determine turbidity, as a measure of protein particulates produced by the different protein precipitation procedures and the ability of the Captiva® filter plate with or without sorbent to remove the particulates. The results are shown in FIG. 22.

Figure 22:
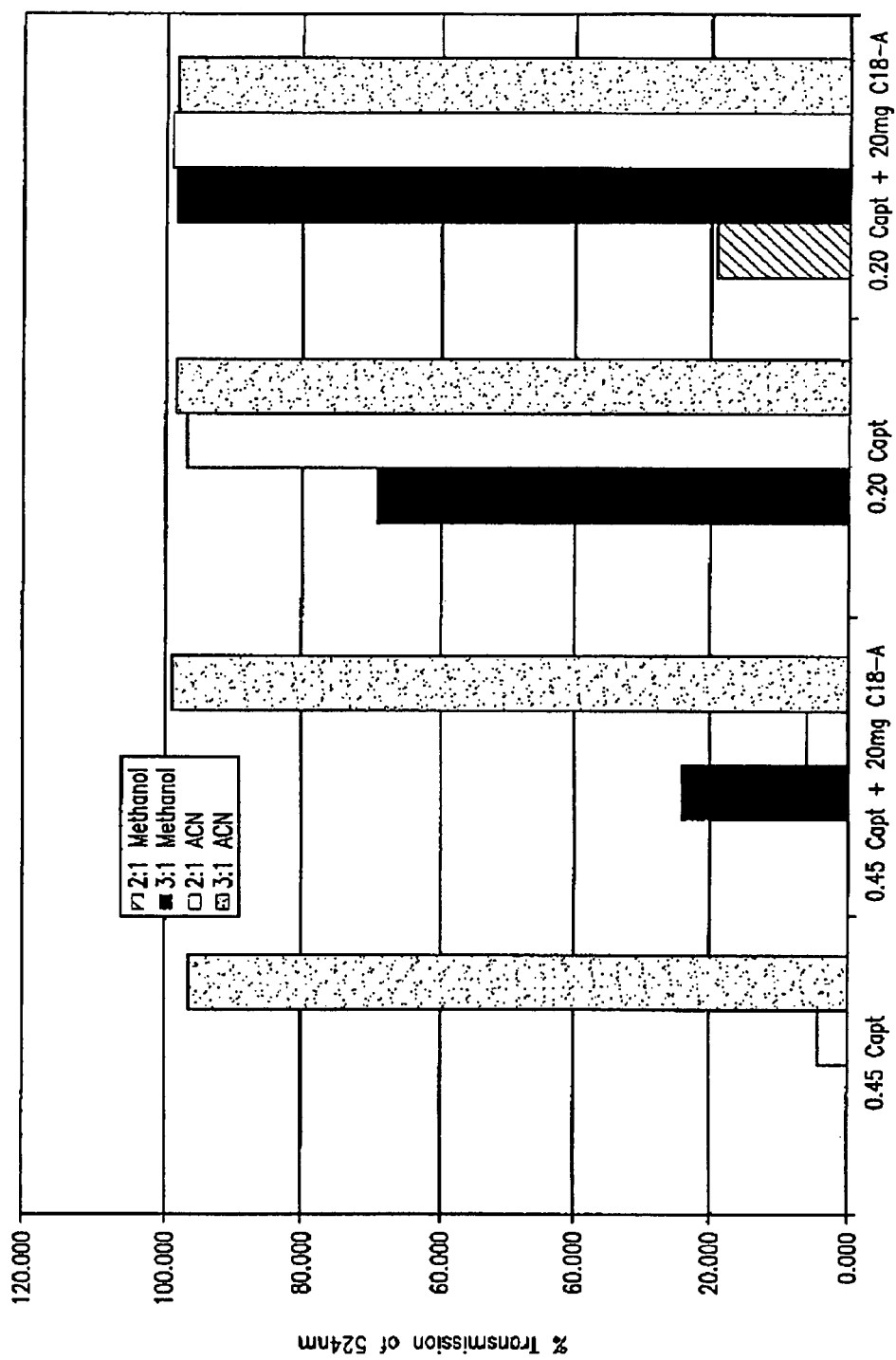
FIG. 22 shows a bar chart illustrating turbidity of protein precipitated samples subjected to filtration through filters with varying pore sizes.

As shown in FIG. 22, protein precipitation using MeOH dilution produces the smallest particulates, which could not be removed by filtration through 0.45 μm pore size Captiva® filters alone (% T was zero). The addition of 20 mg sorbent removed a small amount of the protein precipitates (% T was ~25%). Use of 0.2 μm pore size filters provided better results for 60% (v/v) MeOH precipitated samples (~50% T was achieved); however, % T was still zero for 66% (v/v) MeOH precipitated samples. Addition of 20 mg sorbent provided better particulate removal, with ~20% T for 66% (v/v) MeOH precipitated plasma, and ~100% T for 75% (v/v) MeOH precipitated plasma.

Protein precipitation using ACN dilution produced larger particulates that could be partially removed by filtration through 0.45 μm pore size Captiva® filters alone: % T was ~5% for 66% (v/v) precipitation and ~95% for 75% (v/v) precipitation. The addition of 20 mg sorbent removed slightly more of the protein precipitates: % T was ~7% for 66% (v/v) precipitation and ~98% for 75% (v/v) precipitation. Use of 0.2 μm pore size Captiva® filters alone provided maximal removal of particulates: % T was ~97% for 66% (v/v) precipitation and ~98% for 75% (v/v) precipitation. The addition of 20 mg sorbent removed slightly more of the protein precipitates: % T was ~99% for 66% (v/v) precipitation and ~98% for 75% (v/v) precipitation.

Thus, the method of protein precipitation produces variable particulate sizes, which can be removed using an appropriate filtration method possessing the requisite particle size filtration capabilities. Acceptable protein particulate removal for 75% (v/v) MeOH precipitated samples was only achieved using 0.2 μm pore size Captiva® filters with 20 mg sorbent. Acceptable protein particulate removal for 75% (v/v) ACN precipitated samples was achieved using 0.45 μm pore size Captiva® filters with or without 20 mg sorbent or using 0.2 μm pore size Captiva® filters with or without sorbent; while for 66% (v/v) ACN, acceptable particulate removal was achieved only with 0.2 μm pore size filters, and was equivalent with and without sorbent.

EXAMPLE 8

Rate of Removal of Matrix Interfering Agents

Porcine plasma samples (0.2 ml) were protein precipitated by the addition of 0.6 ml 1.0% formic acid in ACN. Protein precipitates were removed by centrifugation (5000 rpm for 20 minutes in a Sorvall 50 ml rotor). Samples were spiked with analytes (Zolpidem, Warfarin, Sulindac, Loratadine, Vardenafil) to 1 ppm and with Tween 80 to 5 mg/ml. Samples were contacted with the sorbents (20 mg Polaris® C18-Amide (10 μm) or ND 06262) for the following time periods in a 96 well plate with a 0.45 μm Captiva® filter and then separated from the sorbents by vacuum filtration through a collection plate: approximately 10, 20, 50, 120 seconds or 5, 10, 15, 60, 150 seconds. The contact time with sorbent was controlled by varying the flow rate by applying variable vacuum: −15 inches Hg resulted in 10 seconds of contact with sorbent. Additional applied vacuum of −10, −5, −2.5, −2 inches of Hg gave the contact times shown. Filtrates were then analyzed by HPLC as described in Example 2 to determine the recovery of analytes and the amount of phosphatidylcholine and Tween 80 removed. The results are shown in FIGS. 23 and 24.

Figure 23:
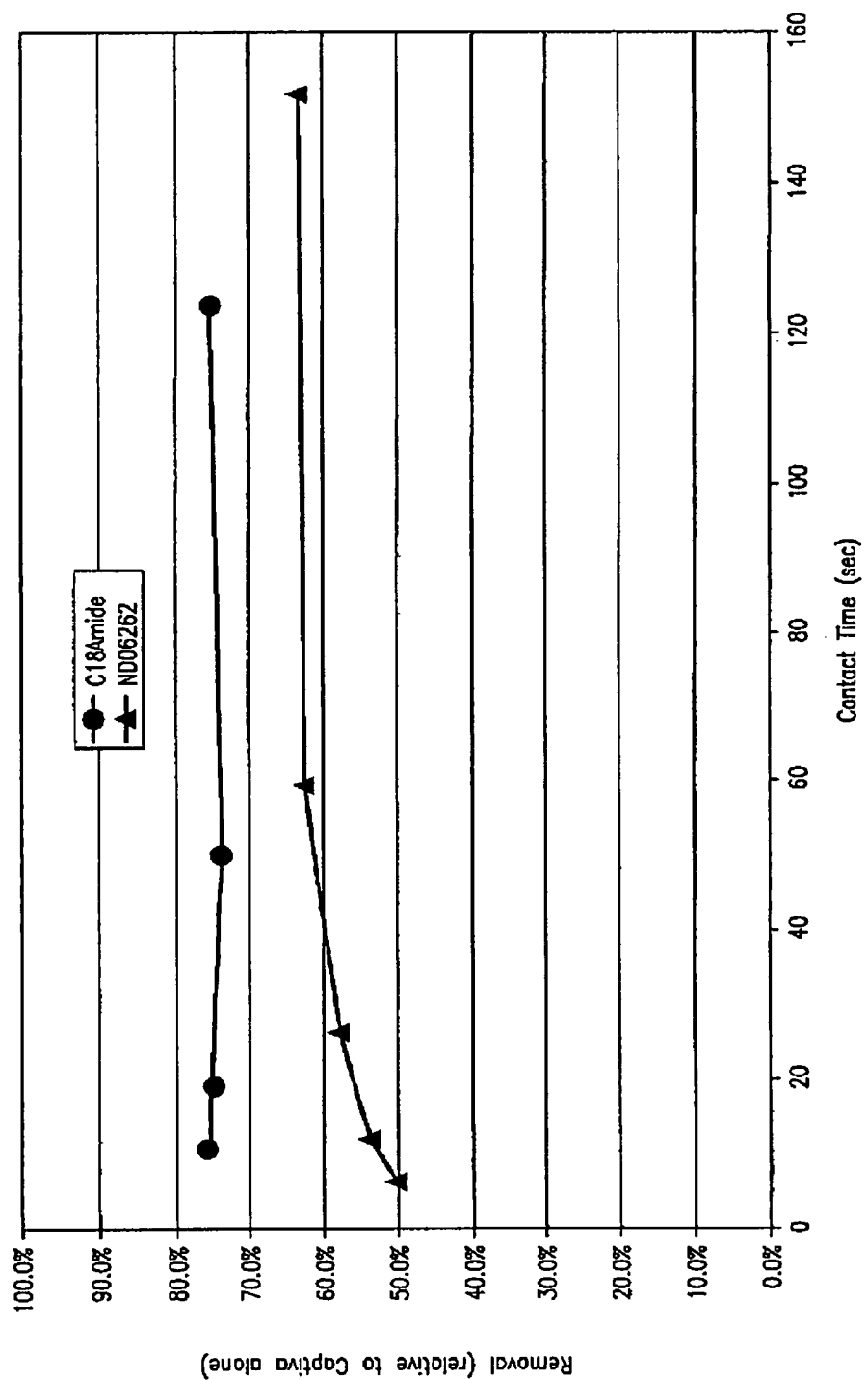
FIG. 23 shows the time dependence for removal of phosphatidylcholine from protein precipitated plasma samples by two sorbents.

FIG. 23 demonstrates that approximately 75% of the phosphatidylcholine was removed from the plasma samples by Polaris® C18 Amide within 10 seconds of exposure to the sorbent, and did not change over the time period tested, and that ND 06262 was able to remove at least 50% of the phosphatidylcholine within 5 seconds, and increased slightly to over 60% by 150 seconds of contact between the sample and the sorbent.

Figure 24:
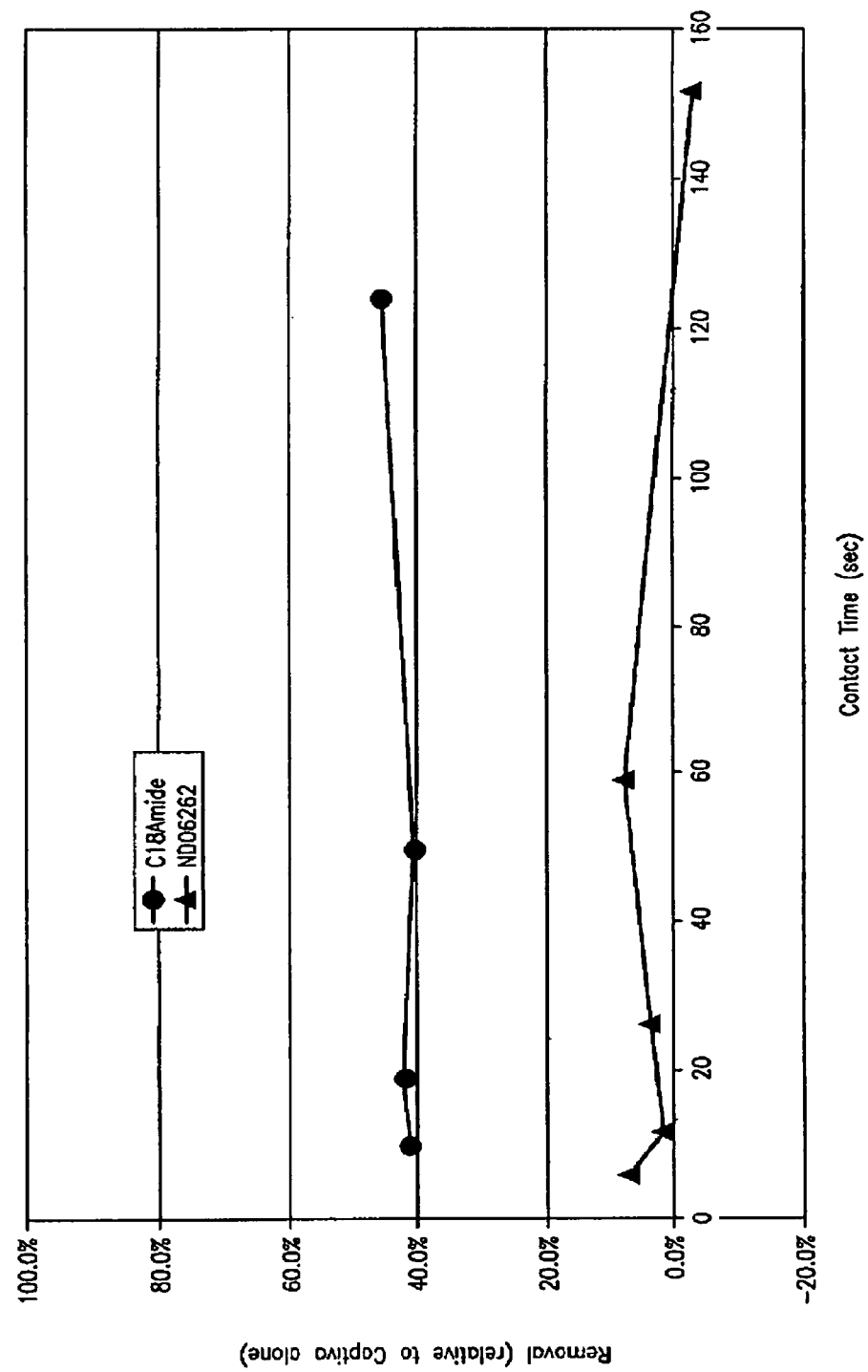
FIG. 24 shows the time dependence for removal of Tween 80 from protein precipitated plasma samples by two sorbents.

FIG. 24 demonstrates that approximately 40% of the Tween 80 was removed from the plasma samples by Polaris® C18 Amide within 10 seconds of exposure to the sorbent, and this amount increased only slightly over the time period tested. ND 06262 was able to remove very little of the Tween 80 over the time period tested.

Analyte detection was dependent on contact time of the plasma samples with Polaris® C18 Amide. Analyte detection was greater than 100% (relative to filtration alone) for all contact times of 20 seconds or longer, indicating that maximal phospholipids and Tween 80 removal had occurred by 20 seconds of exposure time to the sorbent. (data not shown)

Analyte detection was not as clearly dependent on contact time of the plasma samples with ND 06262, indicating that this sorbent was not as effective at removing phosphatidylcholines and Tween 80 as Polaris® C18 Amide under these solvent conditions. (data not shown)

EXAMPLE 9

Optimizing Solvent Conditions to Maximize Removal of Phosphatidylcholines

Human plasma was spiked with the following analytes: pseudoephedrine, carbamazepine, desloratadine, propranolol, and posaconazole to 100 ng/ml (0.1 ppm). Aliquots of spiked plasma (0.1 ml) were removed (n=6) and 0.2 ml or 0.3 ml organic solvent with or without pH modifier was added to each aliquot to precipitate proteins. Denaturing solvents tested were acetone, ACN, MeOH at 2:1 and 3:1 dilution of plasma volumes, with or without 2% formic acid. Each protein precipitated plasma sample was passed through either a well of a Captiva® plate containing 20 mg Polaris® C18-A sorbent, or transferred to another 96 well plate. Water (0.2 ml) was added to dilute each sample prior to HPLC and 10 µl aliquots were analyzed using an API 5000 LC/MS-MS system. Recovery was calculated by dividing the average area count of each analyte which passed through the plate by the average area count of each analyte which did not pass through the plate.

The results are shown in Tables 15-18 below.

TABLE 15

Solvent dilution 2:1 without pH modifier

| Analyte | Log P | Acetone | ACN | MeOH |
|---|---|---|---|---|
| Recovery | | | | |
| pseudoephedrine | 1.51 | 136% | 90% | 88% |
| carbamazepine | 2.69 | 88% | 89% | 90% |
| desloratadine | 3.23 | 76% | 78% | 57% |
| propranolol | 3.59 | 82% | 82% | 70% |
| posaconazole | 5.66 | 65% | 67% | 44% |
| Removal | | | | |
| lysoPC | | 17% | 2% | 94% |
| PC | | 100% | 100% | 100% |

TABLE 16

Solvent dilution 2:1 with pH modifier (2% formic acid)

| Analyte | Log P | Acetone | ACN | MeOH |
|---|---|---|---|---|
| Recovery | | | | |
| pseudoephedrine | 1.51 | 98% | 86% | 93% |
| carbamazepine | 2.69 | 96% | 84% | 90% |
| desloratadine | 3.23 | 96% | 69% | 81% |
| propranolol | 3.59 | 96% | 79% | 87% |
| posaconazole | 5.66 | 82% | 72% | 37% |
| Removal | | | | |
| lysoPC | | 2% | 5% | 100% |
| PC | | 100% | 100% | 100% |

TABLE 17

Solvent dilution 3:1 without pH modifier

| Analyte | Log P | Acetone | ACN | MeOH |
|---|---|---|---|---|
| Recovery | | | | |
| pseudoephedrine | 1.51 | 161% | 93% | 99% |
| carbamazepine | 2.69 | 105% | 94% | 101% |
| desloratadine | 3.23 | 100% | 87% | 80% |
| propranolol | 3.59 | 101% | 88% | 90% |
| posaconazole | 5.66 | 95% | 91% | 71% |
| Removal | | | | |
| lysoPC | | 28% | 5% | 32% |
| PC | | 97% | 100% | 100% |

TABLE 18

Solvent dilution 3:1 with pH modifier (2% formic acid)

| Analyte | Log P | Acetone | ACN | MeOH |
|---|---|---|---|---|
| Recovery | | | | |
| pseudoephedrine | .51 | 100% | 90% | 109% |
| carbamazepine | 2.69 | 97% | 89% | 110% |
| desloratadine | 3.23 | 95% | 79% | 99% |

TABLE 18-continued

Solvent dilution 3:1 with pH modifier (2% formic acid)

| Analyte | Log P | Acetone | ACN | MeOH |
|---|---|---|---|---|
| propranolol | 3.59 | 98% | 88% | 108% |
| posaconazole | 5.66 | 124% | 88% | 66% |
| Removal | | | | |
| lysoPC | | 11% | 10% | 62% |
| PC | | 97% | 100% | 100% |

These results demonstrate the surprisingly complete removal of phosphatidylcholines, including significant amount of lysophosphatidylcholines, while recovering analytes of a wide range of polarities from the sorbent.

EXAMPLE 10

Preparation of a Device for Reducing Matrix Effects

A device was prepared for reducing matrix effects in a bioanalytical sample comprising the following steps: a slurry of 10 mg/ml Polaris® C18-A (10 µm) in MeOH was prepared and 2 ml (20 mg) was added to each well of a Captiva® 96 well plate including a 0.2 µm size exclusion filter (polypropylene). The MeOH was removed by suction through the filters, and a frit was placed on top of each sorbent bed. The device was then ready for use.

EXAMPLE 11

Performance of a Device for Reducing Matrix Effects

Porcine plasma samples were spiked with analytes (Zolpidem, Warfarin, Sulindac, Loratadine, Loperamide, Vardenafil) to 1 ppm each and with Tween 80 to 5 mg/ml and 0.2 ml aliquots were protein precipitated in wells of a modified 96 well Captiva® plate. The plate was modified to contain 20 mg Polarise C18-A (10 µm) on top of the 0.2 µm polypropylene Captiva® filter. MeOH/3% formic acid (0.6 ml) was added to the sample and mixed by pipetting (5 cycles of 0.6 ml) and then filtered through the plate by vacuum filtration. Three different lots of Polaris® C18-A sorbent were tested. Treated samples were analyzed using HPLC as described in Example 3.

The results demonstrated >100% recovery of analytes on average, indicating that matrix effects had been reduced. Approximately 85% of Tween 80, 65% of lysophosphatidylcholines, and 99% of phosphatidylcholines were removed using the device (data not shown). Overall, sample preparation required only a few minutes of time to measure and mix samples plus solvents, then a few seconds to recover the treated samples, now ready for immediate analysis.

What is claimed is:

1. A device for reducing matrix effects in a protein precipitated bioanalytical sample comprising:
   a) a support,
   b) a sorbent associated with the support capable of binding matrix interfering agents present in the bioanalytical sample; and
   c) a filtering means for removing precipitated protein particles, wherein the filtering means is characterized in having pore sizes between about 0.05 µm and about 0.5 µm in diameter.

2. The device of claim 1, wherein the filtering means is selected from a size exclusion filter or a polymeric or inorganic monolith having a maximum pore size less than or equal to the diameter of the particles to be removed from the sample.

3. The device of claim 1, wherein the filtering means is integral with the sorbent or associated with the sorbent.

4. The device of claim 1, wherein the filtering means is a porous monolith having macropores of a diameter sufficiently small so as to exclude particles from the sample, and the sorbent is a reversed phase or polar modified reversed phase bonded to the porous monolith.

5. The device of claim 1, wherein the sorbent is characterized by sufficient selectivity between the matrix interfering agents and analytes of interest to provide retention of the matrix interfering agents while providing elution of the analytes of interest.

6. The device of claim 5, wherein the sorbent is characterized by a selectivity greater than 1 between matrix interfering agents and analytes of interest.

7. The device of claim 1, wherein the sorbent comprises a reversed phase or a polar modified reversed phase.

8. The device of claim 7, wherein the polar modified reversed phase is an amide modified reversed phase.

9. The device of claim 1, wherein the matrix interfering agent is a surfactant, lipid, excipient, or dosing agent.

10. The device of claim 1, adapted for use as a luer syringe filter, individual filter cartridge, a multiwall plate, pipette tip, or an inline column for multiple or single use.

11. The device of claim 1, wherein the support further comprises reservoir means for performing protein precipitation within the device.

12. A method for reducing matrix effects and removing protein precipitates in a bioanalytical sample, said method comprising:
   a) providing the device of claim 1;
   b) contacting the bioanalytical sample with the sorbent; and
   c) eluting analytes from the sorbent while retaining the matrix interfering agents and precipitated proteins,
   wherein the amount of matrix interfering agents and proteins in the resulting treated sample is reduced.

13. The method of claim 12, further comprising precipitating the proteins in the bioanalytical sample in the device prior to or simultaneously with the step of contacting the bioanalytical sample with the sorbent.

14. The method of claim 12, wherein step c) is performed using vacuum, centrifugal or electrokinetic force, gravity or capillary forces, or positive pressure.

15. The method of claim 12, wherein the matrix interfering agents are surfactants, lipids, excipients, or dosing agents.

16. The method of claim 12, wherein the sorbent is characterized by sufficient selectivity between the matrix interfering agents and analytes of interest to provide retention of the matrix interfering agents while providing elution of the analytes of interest.

17. A method for reducing matrix effects and removing precipitated proteins in a protein precipitated bioanalytical sample, the method comprising passing the sample through the device of claim 1.

18. A method for preparing the device of claim 1 comprising the following steps:
   a) providing a support capable of containing a quantity of sorbent and a filtering means;
   b) providing an amount of sorbent effective to retain matrix interfering agents and filtering means effective to remove precipitated proteins; and
   c) assembling the filtering means and the sorbent within the support.

* * * * *

UNITED STATES PATENT AND TRADEMARK OFFICE
CERTIFICATE OF CORRECTION

| | |
|---|---|
| PATENT NO. | : 9,040,672 B2 |
| APPLICATION NO. | : 13/175161 |
| DATED | : May 26, 2015 |
| INVENTOR(S) | : David C. Jones |

It is certified that error appears in the above-identified patent and that said Letters Patent is hereby corrected as shown below:

Title page

On the first page, in item (56), in column 2, under "Other Publications", line 23, delete "Bionanalysis" and insert -- Bioanalysis --, therefor.

On the page 2, in column 1, under "Other Publications", line 6, delete "exhange" and insert -- exchange --, therefor.

On the page 2, in column 2, under "Other Publications", line 2, delete "Anaylsis" and insert -- Analysis --, therefor.

In the Drawings

On sheet 1 of 24, in Figure 1, line 9, delete "Leur" and insert -- Luer --, therefor.

In the Specification

In column 1, lines 24-53, below "spectrometry" delete "(LC/MS/MS)....(2004))." and insert the same on Col. 1, Line 24 as the continuation of the same paragraph.

In column 2, line 24, delete "Empore," and insert -- Empire, --, therefor.

In column 2, line 54, delete "Home," and insert -- Horne, --, therefor.

In column 2, line 57, delete "Home," and insert -- Horne, --, therefor.

In column 6, line 32, delete "conprise" and insert -- comprise --, therefor.

In column 8, line 7, delete "usedherein" and insert -- used herein --, therefor.

Signed and Sealed this
Twenty-fourth Day of November, 2015

Michelle K. Lee
*Director of the United States Patent and Trademark Office*

CERTIFICATE OF CORRECTION (continued)
U.S. Pat. No. 9,040,672 B2

In the Specification

In column 8, line 51, delete "moeities" and insert -- moieties --, therefor.

In column 8, line 58, delete "moeities" and insert -- moieties --, therefor.

In column 9, line 33, delete "spectromertry" and insert -- spectrometry --, therefor.

In column 14, line 46, delete "—O'," and insert -- —O—, --, therefor.

In column 14, line 50, delete "'OPO$_3$—," and insert -- —OPO$_3$—, --, therefor.

In column 15, line 25, delete "—(CH$_2$CH$_2$O)$_n$—" and insert -- —(CH$_2$CH$_2$O)$_s$— --, therefor.

In column 15, lines 61-62, delete "aminosi lanes," and insert -- aminosilanes, --, therefor.

In column 19, line 45, delete "stearine" and insert -- stearin --, therefor.

In column 20, line 27, delete "octooleate," and insert -- octaoleate, --, therefor.

In column 21, line 25, delete "commerically" and insert -- commercially --, therefor.

In column 26, line 14, delete "pipetter." and insert -- pipettor. --, therefor.

In column 38, line 41, delete "Polarise" and insert -- Polaris® --, therefor.